(12) United States Patent
Weiss et al.

(10) Patent No.: US 11,168,306 B2
(45) Date of Patent: Nov. 9, 2021

(54) PHAGE WRAPPING

(71) Applicant: The Regents of the University of California, Oakland, CA (US)

(72) Inventors: Gregory A. Weiss, Irvine, CA (US); Kritika Mohan, Irvine, CA (US); Lindsay Kindra, Irvine, CA (US); Reginald M. Penner, Newport Beach, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 32 days.

(21) Appl. No.: 15/121,153

(22) PCT Filed: Feb. 25, 2015

(86) PCT No.: PCT/US2015/017598
§ 371 (c)(1),
(2) Date: Aug. 24, 2016

(87) PCT Pub. No.: WO2015/130843
PCT Pub. Date: Sep. 3, 2015

(65) Prior Publication Data
US 2017/0067026 A1 Mar. 9, 2017

Related U.S. Application Data

(60) Provisional application No. 61/944,425, filed on Feb. 25, 2014.

(51) Int. Cl.
*C12Q 1/00* (2006.01)
*C12Q 1/70* (2006.01)
(Continued)

(52) U.S. Cl.
CPC ............. *C12N 7/00* (2013.01); *C07D 403/06* (2013.01); *G01N 27/026* (2013.01); *G01N 27/416* (2013.01); *G01N 33/56911* (2013.01); *G01N 33/56916* (2013.01); *G01N 33/574* (2013.01); *G01N 33/57434* (2013.01); *C12N 2795/14131* (2013.01)

(58) Field of Classification Search
None
See application file for complete search history.

(56) References Cited

U.S. PATENT DOCUMENTS

2004/0018203 A1\* 1/2004 Pastan ................ C07K 16/2866
424/178.1
2010/0112072 A1 5/2010 Wang et al.
(Continued)

OTHER PUBLICATIONS

Lamboy et al. Chemical and genetic wrappers for improved phage and RNA display. Chembiochem. Nov. 24, 2008;9(17):2846-52. (Year: 2008).\*
(Continued)

*Primary Examiner* — Michelle S Horning
(74) *Attorney, Agent, or Firm* — Mintz, Levin, Cohn, Ferris, Glovsky and Popeo, P.C.

(57) ABSTRACT

Disclosed herein, inter alia, are compositions and methods useful for improving detection of analytes. The compositions and methods provided include polymer-wrapped viral particles useful, inter alia, for the detection of PSMA.

10 Claims, 25 Drawing Sheets

Specification includes a Sequence Listing.

(51) Int. Cl.
| | |
|---|---|
| C12N 7/00 | (2006.01) |
| G01N 33/574 | (2006.01) |
| C07D 403/06 | (2006.01) |
| G01N 33/569 | (2006.01) |
| G01N 27/02 | (2006.01) |
| G01N 27/416 | (2006.01) |

(56) References Cited

U.S. PATENT DOCUMENTS

| | | |
|---|---|---|
| 2012/0258540 A1 | 10/2012 | Ledoux et al. |
| 2013/0230484 A1 | 9/2013 | Bachmann et al. |
| 2014/0030699 A1 | 1/2014 | Bachmann et al. |

OTHER PUBLICATIONS

Pokorski et al. Cell targeting with hybrid Qβ virus-like particles displaying epidermal growth factor. Chembiochem. Nov. 4, 2011;12(16):2441-7. (Year: 2011).*

Carrico, Z.M. et al. (Aug. 28, 2012, e-published Aug. 6, 2012). "N-Terminal labeling of filamentous phage to create cancer marker imaging agents," *ACS Nano* 6(8):6675-6680.

Chuang, A.Y. et al. (Aug. 2007). "Immunohistochemical differentiation of high-grade prostate carcinoma from urothelial carcinoma," *Am J Surg Pathol* 31(8): 1246-1255.

International Search Report dated Jun. 4, 2015, for PCT Application No. PCT/US2015/017598, filed Feb. 25, 2015, 3 pages.

Ionescu, R.E. et al. (Nov. 15, 2007, e-published Oct. 23, 2007). "Amperometric immunosensor for the detection of anti-West Nile virus IgG," *Anal Chem* 79(22):8662-8668.

Kawakami, M. et al. (Jun. 1997). "Enhanced expression of prostate-specific membrane antigen gene in prostate cancer as revealed by in situ hybridization," *Cancer Res* 57(12):2321-2324.

Lamboy, J.A. et al. (Nov. 18, 2009). "Phage wrapping with cationic polymers eliminates nonspecific binding between M13 phage and high pI target proteins," *J Am Chem Soc* 131(45):16454-16460.

Madu, C.O. et al. (Oct. 6, 2010). "Novel diagnostic biomarkers for prostate cancer," *J Cancer* 1:150-177.

Mehlen, P. et al. (Jun. 2006). "Metastasis: a question of life or death," *Nat Rev Cancer* 6(6):449-458.

Mohan, K. et al. (May 22, 2013, e-published May 13, 2013). "Sub-nanomolar detection of prostate-specific membrane antigen in synthetic urine by synergistic, dual-ligand phage," *J Am Chem Soc* 135(20):7761-7767.

Mohan, K. et al. (May 15, 2014, e-published Mar. 4, 2014). "Dual genetically encoded phage-displayed ligands," *Anal Biochem* 453:1-3.

Moyer, V.A. et al. (Jul. 17, 2012). "Screening for prostate cancer: U.S. Preventive Services Task Force recommendation statement," *Ann Intern Med* 157(2):120-134.

Murphy, G.P. et al. (May 1998). "Measurement of serum prostate-specific membrane antigen, a new prognostic marker for prostate cancer," *Urology* 51 (5A Suppl):89-97.

Nanduri, V. et al. (Jan. 15, 2007, e-published May 30, 2006). "Phage as a molecular recognition element in biosensors immobilized by physical adsorption," *Biosens Bioelectron* 22(6):986-992.

Petrenko, V.A. et al. (Jan. 21, 2014). "Phage protein-targeted cancer nanomedicines," *FEBS Lett* 588(2):341-349.

Sidhu, S.S. et al. (2004). "Constructing Phage Display Libraries by Oligonucleotide-directed Mutagenesis," Chapter 2 in *Phage Display: A Practical Approach*, Oxford University Press, New York, pp. 27-42.

Siegel, R. et al. (Jan.-Feb. 2014, e-published Jan. 7, 2014). "Cancer statistics, 2014," CA Cancer J Clin 64(1):9-29.

Sokoloff, R.L. et al. (May 2000). "A dual-monoclonal sandwich assay for prostate-specific membrane antigen: levels in tissues, seminal fluid and urine," *Prostate* 43(2):150-157.

Su, S.L. et al. (Apr. 1, 1995). "Alternatively spliced variants of prostate-specific membrane antigen RNA: ratio of expression as a potential measurement of progression," *Cancer Res* 55(7):1441-1443.

Written Opinion dated Jun. 4, 2015, for PCT Application No. PCT/US2015/017598, filed Feb. 25, 2015, 7 pages.

Xiao, Z. et al. (Aug. 15, 2001). "Quantitation of serum prostate-specific membrane antigen by a novel protein biochip immunoassay discriminates benign from malignant prostate disease," *Cancer Res* 61(16):6029-6033.

* cited by examiner

FIG. 23
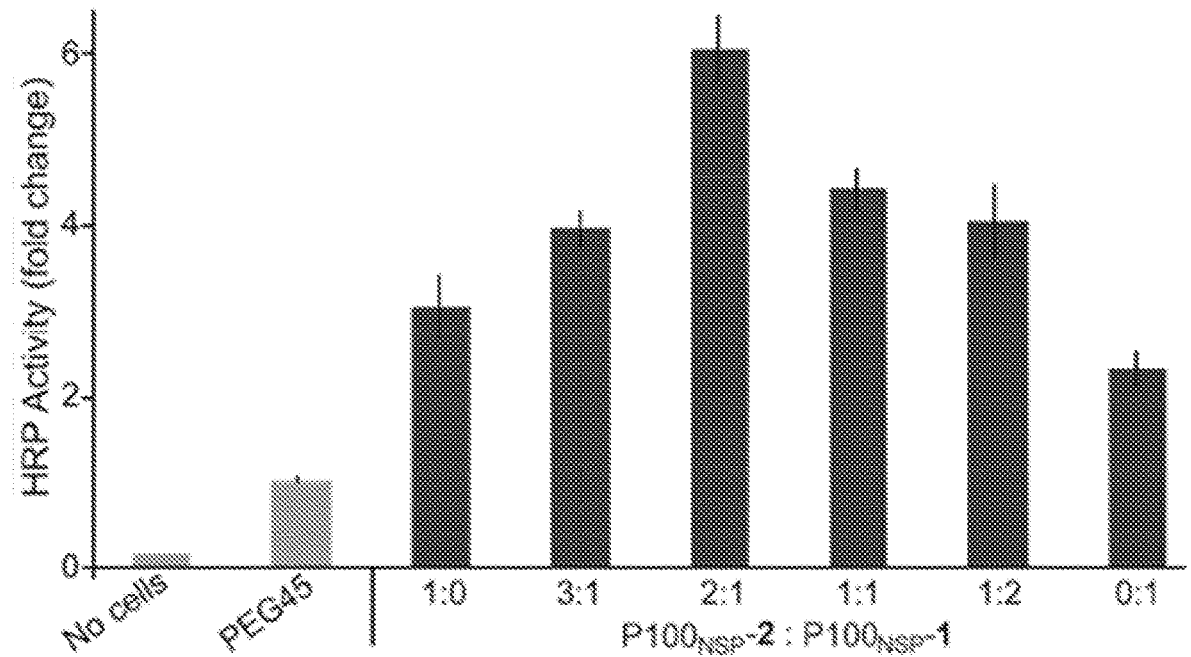
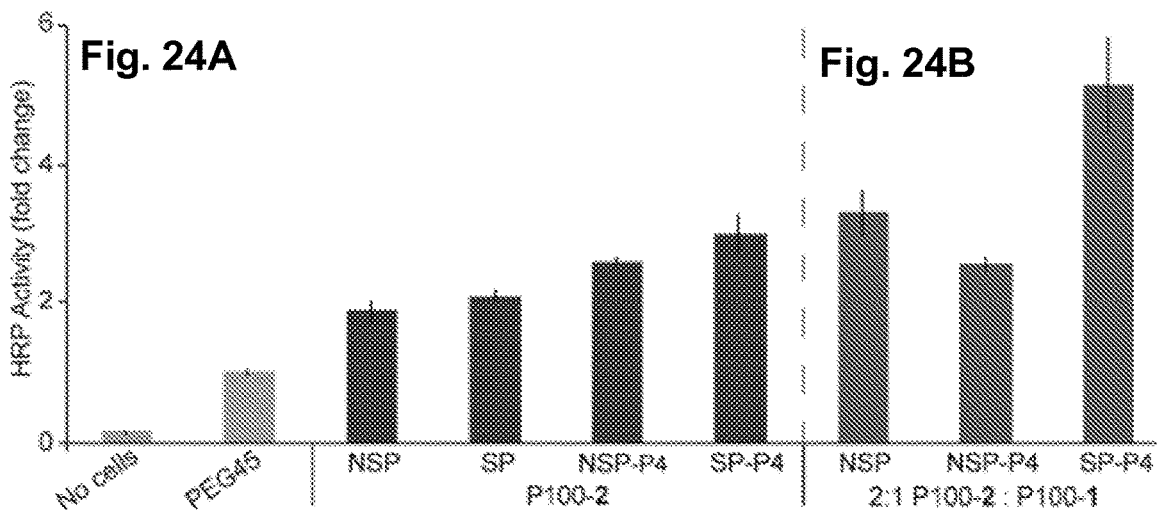

[0001]

PHAGE WRAPPING

CROSS-REFERENCES TO RELATED APPLICATIONS

This application claims the benefit of U.S. Provisional Appl. No. 61/944,425, filed Feb. 25, 2014, the content of which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant no. CA133592, awarded by the National Institutes of Health. The government has certain rights in the invention.

REFERENCE TO A "SEQUENCE LISTING," A TABLE, OR A COMPUTER PROGRAM LISTING APPENDIX SUBMITTED ON A COMPACT DISK

The Sequence Listing written in file 048538-501NO1US_Sequence_Listing_ST25.txt, created on Sep. 9, 2020, 692 bytes, machine format IBM-PC, MS-Windows operating system, is hereby incorporated by reference in its entirety for all purposes.

BACKGROUND

The migration and dissemination of tumor cells, termed metastasis, causes ≈90% of cancer deaths (Joosse, S. A.; Gorges, T. M.; Pantel, K. EMBO Mol. Med. 2014, doi: 10.15252/emmm.201303698; Mehlen, P.; Puisieux, A. Nat. Rev. Cancer 2006, 6, 449-458) Metastasis requires loss of apoptotic regulation, and such cells respond poorly to conventional anti-cancer treatments. With a majority of the estimated 29,000 deaths from prostate cancer (PCa) in the US for 2014 (Siegel, R.; Ma, J.; Zou, Z.; Jemal, A. CA. Cancer J. Clin. 2014, 64, 9-29;) resulting from metastasis (Mehlen, P.; Puisieux, A. Nat. Rev. Cancer 2006, 6, 449-458; (3) Siegel, R.; Ma, J.; Zou, Z.), new methods for efficient detection and characterization of metastatic cells could impact clinical care and patient prognosis. Previously, we reported the sensitive detection of soluble prostate-specific membrane antigen (PSMA), a PCa biomarker, at 100 pM concentrations using viruses incorporated into an electrically conductive polymer. (Mohan, K.; Donavan, K. C.; Arter, J. A.; Penner, R. M.; Weiss, G. A. J. Am. Chem. Soc. 2013, 135, 7761-7767)

PSMA, a 750 residue, 90 kD glycoprotein, is overexpressed on the surface of tumor cells as a non-covalent homodimer in both primary and metastatic cancers. (Schülke, N.; Varlamova, O. A.; Donovan, G. P.; Ma, D.; Gardner, J. P.; Morrissey, D. M.; Arrigale, R. R.; Zhan, C.; Chodera, A. J.; Surowitz, K. G.; Maddon, P. J.; Heston, W. D. W.; Olson, W. C. Proc. Natl. Acad. Sci. USA 2003, 100, 12590-12595; Chuang, A.-Y.; DeMarzo, A. M.; Veltri, R. W.; Sharma, R. B.; Bieberich, C. J.; Epstein, J. I. Am. J. Surg. Pathol. 2007., 31, 1246-1255) Differential splicing during tumorigenesis leads to expression of PSMA as a type II integral membrane protein. (Kawakami, M.; Nakayama, J. Cancer Res. 1997, 57, 2321-2324) Elevated PSMA levels have also been observed in seminal fluid and urine of PCa patients. A(Sokoloff, R. L.; Norton, K. C.; Gasior, C. L.; Marker, K. M.; Grauer, L. S. Prostate 2000, 43, 150-157) To detect the protein in urine, we reported viruses with both genetically displayed and chemically synthesized ligands for the sensitive detection of PSMA. (Mohan, K.; Donavan, K. C.; Arter, J. A.; Penner, R. M.; Weiss, G. A. J. Am. Chem. Soc. 2013, 135, 7761-7767; Mohan, K.; Weiss, G. A. Anal. Biochem. 2014, 453, 1-3) These ligands, selected from with phage-displayed peptide libraries had the following amino acid sequences: ligand-1 (CALCEFLG) and ligand-2 (SECVEVFQNSCDW). Genetically encoded, phage-displayed ligand-2 binds with >100-fold higher affinity to PSMA than ligand-1. (Mohan, K.; Donavan, K. C.; Arter, J. A.; Penner, R. M.; Weiss, G. A. J. Am. Chem. Soc. 2013, 135, 7761-7767; Arter, J. A.; Diaz, J. E.; Donavan, K. C.; Yuan, T.; Penner, R. M.; Weiss, G. A. Anal. Chem. 2012, 84, 2776-2783)

Used ubiquitously for molecular display applications, the M13 filamentous bacteriophage infects E. coli, and can be manipulated to present genetically encoded peptides on the phage surface. (Smith, G. P. Science 1985, 228, 1315-1317; Sidhu, S. S.; Weiss, G. A. In Phage Display: A Practical Approach; Lowman, H. B.; Clackson, T., Eds.; Oxford University Press: New York, 2004; pp. 27-42; Scott, J. K.; Smith, G. P. Science 1990, 249, 386-90) The M13 virus consists of a single-stranded, circular DNA genome surrounded by a protein coat consisting of approximately 2700 copies of the major coat protein, P8, an alpha helical protein of 50 amino acid residues with an unstructured N-terminus. One Glu and two Asp near the N-terminus of P8 impart a high negative charge to the outer surface of the virus at physiological pH. (Welsh, L. C.; Symmons, M. F.; Sturtevant, J. M.; Marvin, D. A.; Perham; R. N. J. Mol. Biol. 1998, 283, 155-177) Selections with phage-displayed libraries of peptides and proteins can target tissue-cultured cells and even organs in living organisms. (Carrico, Z. M.; Farkas, M. E.; Zhou, Y.; Hsiao, S. C.; Marks, J. D.; Chokhawala, H.; Clark, D. S.; Francis, M. B. ACS Nano 2012, 6, 6675-6680; Trepel, M.; Arap, W.; Pasqualini, R. Curr. Opin: Chem. Biol. 2002, 6, 399-404; Abbineni, G.; Modali, S.; Safiejko-Mroczka, B.; Petrenko, V. A.; Mao, C. Mol. Pharm. 2010, 7, 1629-1642) Phage have been incorporated into nanomedicine platforms for targeted drug delivery. (Petrenko, V. A.; Jayanna, P. K. FEBS Lett. 2014, 588, 341-349; Jayanna, P. K.; Torchilin, V. P.; Petrenko, V. A. Nanomedicine. 2009, 5, 83-89; Wang, T.; Yang, S.; Petrenko, V. A.; Torchilin, V. P. Mol. Pharm. 2010, 7, 1149-1158) Francis and co-authors have also reported covalently linking the coat proteins of fd phage with polyethylene glycol (PEG) and also imaging agents through a two step reaction requiring >24 h. (Carrico, Z. M.; Farkas, M. E.; Zhou, Y.; Hsiao, S. C.; Marks, J. D.; Chokhawala, H.; Clark, D. S.; Francis, M. B. ACS Nano 2012, 6, 6675-6680)

Phage typically adhere to cell surfaces with high affinity. Such non-specific adhesion can complicate selections, as every member of the library is equally eligible for selection due to their high affinity for all cell surfaces. A similar problem arises with phage-based sensors for the detection of tumor cells; the non-specific background can reduce signal to noise, and ability to distinguish tumor from non-tumor cells.

More-effective biosensors could address a critical need for detecting cancer-associated biomarkers and other disease-associated markers. An estimated 29 000 men in the United States will succumb to prostate cancer in 2013. (Siegel, R.; Naishadham, D.; Jemal, A. CA-Cancer J. Clin. 2013, 63, 11-30.) The lack of validated clinical diagnostic markers complicates efforts to develop tests for early prostate cancer detection. For example, a recent report concludes that the prostate-specific antigen (PSA) test used for prostate cancer diagnostics is more harmful than beneficial. (Moyer, V. A. Ann. Int. Med. 2012, 157, 120-134.) Despite this caveat, PSA remains an important biomarker for detecting recurrent prostate cancer. However, early detection of the disease could enable more-effective treatment and prognosis (Madu, C. O.; Lu, Y. L. J. Cancer 2010, 1, 150-177.) Thus, issues addressable by bioanalytical chemistry include the development of more-sensitive measurements of protein concentration and then applying such measurements to identify and validate more-effective biomarkers.

Unlike PSA, prostate-specific membrane antigen (PSMA) concentrations in biological fluids appear to offer a more-useful metric for prostate cancer diagnosis and prognosis. (Murphy, G. P.; Kenny, G. M.; Ragde, H.; Wolfert, R. L.; Boynton, A. L.; Holmes, E. H.; Misrock, S. L.; Bartsch, G.; Klocker, H.; Pointner, J.; Reissigl, A.; McLeod, D. G.; Douglas, T.; Morgan, T.; Gilbaugh, J. Urology 1998, 51, 89-97.) For example, elevated PSMA levels have been observed in prostate cancer patients' urine. (Sokoloff, R. L.; Norton, K. C.; Gasior, C. L.; Marker, K. M.; Grauer, L. S. Prostate 2000, 43, 150-157.) The PSMA concentration increases from 0.25 nM to approximately 3.5 nM in prostate cancer patients' biological fluids, including urine. (Xiao, Z.; Adam, B.-L.; Cazares, L. H.; Clements, M. A.; Davis, J. W.; Schellhammer, P. F.; Dalmasso, E. A.; Wright, G. L. Cancer Res. 2001, 61, 6029-6033.) PSMA, a 750-residue, 90-kDa glycoprotein, is overexpressed on the surface of tumor cells as a non-covalent homodimer in >94.3 and >57.7% of primary and metastatic prostate cancers respectively. (Schülke, N.; Varlamova, 0. A.; Donovan, G. P.; Ma, D.; Gardner, J. P.; Morrissey, D. M.; Arrigale, R. R.; Zhan, C.; Chodera, A. J.; Surowitz, K. G.; Maddon, P. J.; Heston, W. D. W.; Olson, W. C. Proc. Natl. Acad. Sci. U.S.A. 2003, 100, 12590-12595. Chuang, A.-Y.; DeMarzo, A. M.; Veltri, R. W.; Sharma, R. B.; Bieberich, C. J.; Epstein, J. I. Am. J. Surg. Pathol. 2007, 31, 1246-1255.) Elevated PSMA levels also correlate with the aggressiveness of tumor growth. (Su, S. L.; Huang, I. P.; Fair, W. R.; Powell, C. T.; Heston, W. D. Cancer Res. 1995, 55, 1441-1443.) Thus, PSMA offers an important biomarker for the development of biosensor-based diagnostic devices. Described herein is the development of a biosensor capable of detecting clinically relevant concentrations of PSMA (<0.25 nM) in synthetic urine.

In 2003, Petrenko and Vodyanoy demonstrated the use of whole virus particles as a bioaffinity matrix for biosensors. (Petrenko, V. A.; Vodyanoy, V. J. J. Microbiol. Methods 2003, 53, 253-262. Nanduri, V.; Sorokulova, I. B.; Samoylov, A. M.; Simonian, A. L.; Petrenko, V. A.; Vodyanoy, V. Biosens. Bioelectron. 2007, 22, 986-992.) In an improved generation of biosensors, T7 virus particles with a peptide antigen from the West Nile virus on their surfaces have been incorporated into conducting polymers by Cosnier and co-workers to allow detection of antibodies to the West Nile virus. (Ionescu, R. E.; Cosnier, S.; Herrmann, S.; Marks, R. S. Anal. Chem. 2007, 79, 8662-8668.) This strategy can offer higher density ligands for biomarker binding, as T7 phage have a high density of peptides displayed on their surface.

The sensitive detection of cancer biomarkers in urine could revolutionize cancer diagnosis and treatment. Such detectors must be inexpensive, easy to interpret, and sensitive. Disclosed herein, inter alia, are solutions to these and other problems in the art.

BRIEF SUMMARY

In an aspect is provided a whole viral particle including a charged protein coat, the charged protein coat comprising a charged coat protein electrostatically bound to a functionalized charged polymer or a charged polymer conjugate, wherein the functionalized charged polymer includes a charged polymer covalently bound to a chemically reactive functional group, and wherein the charged polymer conjugate includes a charged polymer covalently bound to a hydrophilic organic polymer.

In an aspect is provided a cationic electronically conductive polymer electrostatically bound to a first whole viral particle, the first whole viral particle including a negatively charged protein coat wherein the negatively charged protein coat comprises a coat protein electrostatically bound to a cationic polymer or a cationic polymer conjugate. In embodiments, the cationic polymer or cationic polymer conjugate includes oligolysine.

In an aspect is provided a method of reducing non-specific binding of whole viral particles to cells including the step of electrostatically binding a functionalized charged polymer or a charged polymer conjugate to the whole virus particle; wherein the functionalized charged polymer includes a charged polymer covalently bound to a chemically reactive functional group, and wherein the charged polymer conjugate includes a charged polymer covalently bound to a hydrophilic organic polymer.

In an aspect is provided a method of improving the sensitivity of a bacterial biosensor, wherein the bacterial biosensor includes a cationic electronically conductive polymer electrostatically bound to a first whole viral particle, and the method includes electrostatically binding a negatively charged coat protein of the whole viral particle to a cationic polymer. In an embodiment, the cationic polymer is polyethylene imine.

In an aspect is provided a method of detecting a biological molecule, the method including: (i) combining a whole viral particle described herein or a cationic electronically conductive polymer described herein and a biological molecule to a reaction vessel; (ii) allowing the whole viral particle or the cationic electronically conductive polymer to specifically bind to the biological molecule; and (iii) detecting the bound biological molecule.

In one aspect, a whole viral particle is provided. The whole viral particle includes a charged protein coat, the charged protein coat includes a charged coat protein electrostatically bound to a functionalized charged polymer, wherein the functionalized charged polymer includes a charged polymer covalently bound to a chemically reactive functional group.

In one aspect, a whole viral particle is provided. The whole viral particle includes a charged protein coat, the charged protein coat includes a charged coat protein electrostatically bound to a charged polymer conjugate, wherein the charged polymer conjugate includes a charged polymer covalently bound to a hydrophilic organic polymer.

In another aspect, a method of forming a virus particle polymer ligand conjugate is provided. The method includes contacting a first functionalized charged polymer with a charged virus coat protein, wherein the first functionalized charged polymer is covalently bound to a first chemically reactive functional group, thereby forming a virus particle polymer conjugate. The first chemically reactive functional group of the virus particle polymer conjugate is contacted with a second chemically reactive functional group covalently bound to a second polymer, wherein the second polymer is covalently linked to a ligand domain, thereby forming a virus particle polymer ligand conjugate.

BRIEF DESCRIPTION OF THE DRAWINGS

(FIG. 3A) Phage with chemically and genetically encoded ligands bind with much higher apparent affinity to the targeted PSMA. (FIG. 3B) The chemically synthesized $K_{CS}$-2 wrapper converts helper phage KO7, lacking a genetically encoded PSMA ligand, into a high-affinity binding partner to PSMA. The decrease in apparent binding affinity at the highest phage concentration could be attributed to steric effects. (FIG. 3C) ELISA comparing different ligand wrappers. The wrapper combination of $K_{CS}$-2 and $K_{CS}$-1 indicates a 1:1 (w/w) ratio of ligand wrappers.

(FIG. 4A) Cyclic voltammogram for depositing virus-PEDOT films on gold electrodes. (FIG. 4B) SEM image of a PEDOT film. (FIG. 4C) SEM image of a virus-PEDOT film prepared under the same conditions. (FIG. 4D) Relative change in resistance, $\Delta R/R_o$, versus frequency for phage-displayed ligands targeting PSMA. Data collected at 1 kHz (highlighted) were used for the analysis of PSMA binding. (FIG. 4E) Schematic diagram of the biosensing experiment. (FIG. 4F) $\Delta R/R_o$ of the film increases with the PSMA concentration. Throughout this report, error bars for the biosensing data represent standard error (n=5). Data were fit to the indicated lines using the Hill equation, resulting in an $R^2$ value of >0.99.

(FIG. 5A) $\Delta R/R_o$ versus frequency for the detection, in synthetic urine, of PSMA. (FIG. 5B) $\Delta R/R_o$ versus PSMA concentration. The inset expands the low PSMA concentration region. Data were fit to the indicated lines using the Hill equation, resulting in an R2 value of >0.99.

FIG. 23. shows a histogram depicting phage-based ELISA demonstrating the effectiveness of the bidentate binding mode for the two PSMA binding ligands on the phage surface. A 1:1 ratio of the two ligands indicates the assay of equimolar amounts of each ligand.

FIGS. 24A-24B. (FIG. 24A) Phage-based ELISA comparing the different attachment modes with the incorporation of a PEG4 linker for PEGylated ligand-2 targeting PSMA on LNCaP cells. (FIG. 24B) The combination of ligand-1 and -2 leads to increased affinity due to the chelate-based avidity effect.

DETAILED DESCRIPTION

Definitions

Figure 1:
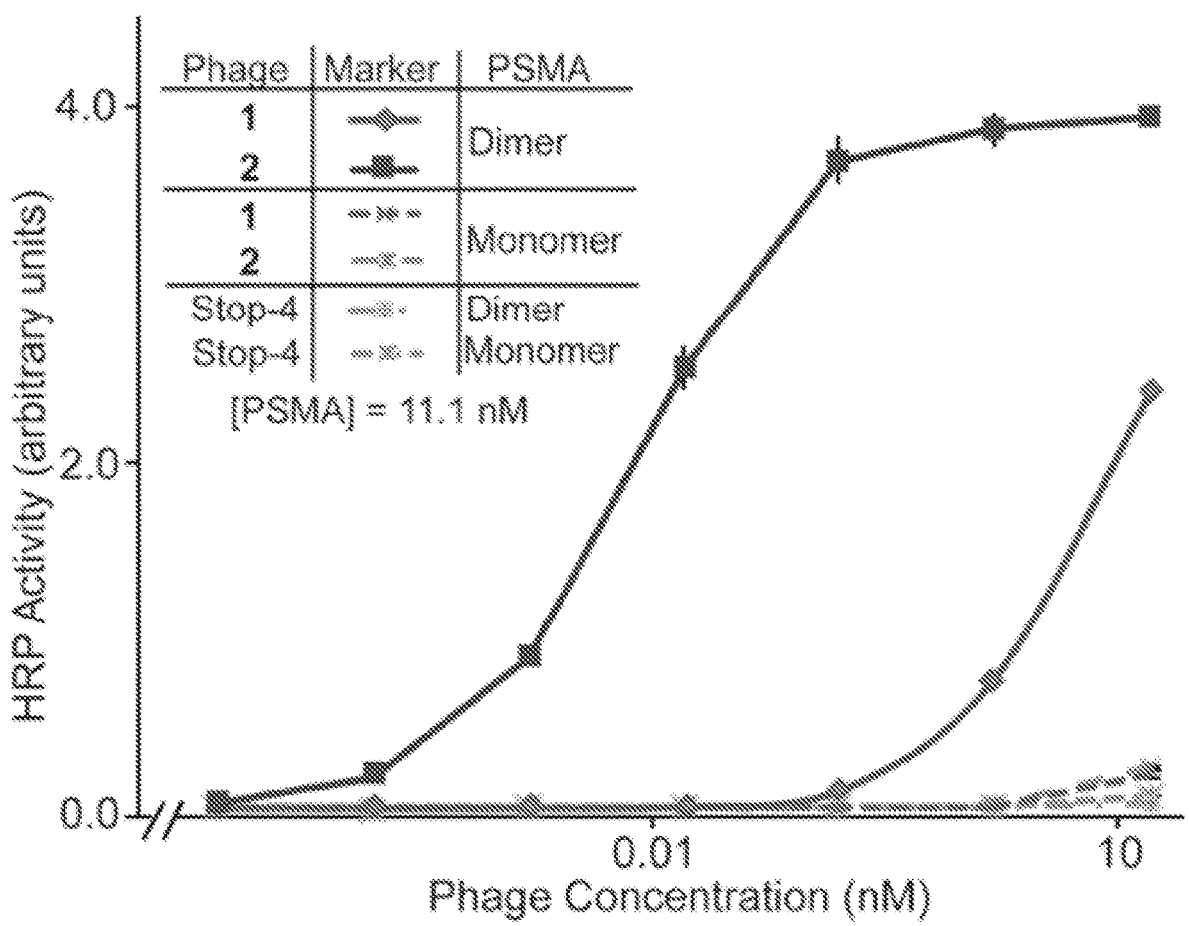
FIG. 1. Phage-based ELISA comparing ligand binding to monomeric and dimeric forms of PSMA. This ELISA includes PSMA monomer; all other experiments with PSMA described herein apply the cancer-relevant PSMA dimer. Stop-4 provides a negative control with helper phage packaging the phagemid DNA. Included herein, error bars for ELISA data represent standard error (n=3). All experimental data points with the exception of the negative controls (n=1) include such error bars, though often these are quite small.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—$N(CH_3)$—$CH_3$, —$CH_2$—S—$CH_2$—$CH_3$, —$CH_2$—$CH_2$, —$S(O)$—$CH_3$, —$CH_2$—$CH_2$—$S(O)_2$—$CH_3$, —CH=CH—O—$CH_3$, —$Si(CH_3)_3$, —$CH_2$—CH=N—$OCH_3$, —CH=CH—$N(CH_3)$—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—$Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$C(O)_2$R'— represents both —$C(O)_2$R'— and —R'$C(O)_2$—. As described above, heteroalkyl groups, as used herein, include those groups that are attached to the remainder of the molecule through a heteroatom, such as —C(O)R', —C(O)NR', —NR'R", —OR', —SR', and/or —$SO_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$N(R)(R"—NRSO$_2$R'), —CN, and —$NO_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R, —C(O)R', —$CO_2$R', —CONR'R", —OC(O)NR'R", —NR"C(O)R', —NR'—C(O)NR"R'", NR"C(O)$_2$R', —NR—C(NR'R")=NR'", —S(O)R', —S(O)$_2$R', —S(O)$_2$N(R')(R", —NRSO$_2$R'), —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{14}$-substituted or unsubstituted alkyl, a plurality of $R^{14}$ substituents may be attached to the alkyl moiety wherein each $R^{14}$ substituent is optionally different. Where an R-substituted moiety is substituted with a plurality R substituents, each of the R-substituents may be differentiated herein using a prime symbol (') such as R', R", etc. For example, where a moiety is $R^{14}$-substituted or unsubstituted alkyl, and the moiety is substituted with a plurality of $R^{14}$ substituents, the plurality of $R^{14}$ substituents may be differentiated as $R^{14'}$, $R^{14''}$, $R^{14'''}$, etc. In some embodiments, the plurality of R substituents is 3. In some embodiments, the plurality of R substituents is 2.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula —T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where variables s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O) NHNH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted, with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single-, double- or multiple-stranded form, or complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including nucleic acids with a phosphothioate backbone can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphodiester derivatives including, e.g., phosphoramidate, phosphorodiamidate, phosphorothioate (also known as phosphothioate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism. An "inhibitory nucleic acid" is a nucleic acid (e.g. DNA, RNA, polymer of nucleotide analogs) that is capable of binding to a target nucleic acid (e.g. an mRNA translatable into a protein) and reducing transcription of the target nucleic acid (e.g. mRNA from DNA) or reducing the translation of the target nucleic acid (e.g. mRNA) or altering transcript splicing (e.g. single stranded morpholino oligo).

A "labeled nucleic acid or oligonucleotide" is one that is bound, either covalently, through a linker or a chemical bond, or noncovalently, through ionic, van der Waals, electrostatic, or hydrogen bonds to a label such that the presence of the nucleic acid may be detected by detecting the presence of the detectable label bound to the nucleic acid. Alternatively, a method using high affinity interactions may achieve the same results where one of a pair of binding partners binds to the other, e.g., biotin, streptavidin. In embodiments, the phosphorothioate nucleic acid or phosphorothioate polymer backbone includes a detectable label, as disclosed herein and generally known in the art.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854).

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The term "isolated", when applied to a nucleic acid or protein, denotes that the nucleic acid or protein is essentially free of other cellular components with which it is associated in the natural state. It can be, for example, in a homogeneous state and may be in either a thy or aqueous solution. Purity and homogeneity are typically determined using analytical chemistry techniques such as polyacrylamide gel electrophoresis or high performance liquid chromatography. A protein that is the predominant species present in a preparation is substantially purified.

The term "purified" denotes that a nucleic acid or protein gives rise to essentially one band in an electrophoretic gel. In some embodiments, the nucleic acid or protein is at least 50% pure, optionally at least 65% pure, optionally at least 75% pure, optionally at least 85% pure, optionally at least 95% pure, and optionally at least 99% pure.

The term "isolated" may also refer to a cell or sample cells. An isolated cell or sample cells are a single cell type that is substantially free of many of the components which normally accompany the cells when they are in their native state or when they are initially removed from their native state. In certain embodiments, an isolated cell sample retains those components from its natural state that are required to maintain the cell in a desired state. In some embodiments, an isolated (e.g. purified, separated) cell or isolated cells, are cells that are substantially the only cell type in a sample. A purified cell sample may contain at least 60%, 70%, 75%, 80%, 85%, 90%, 95%, 96%, 97%, 98%, 99%, or 100% of one type of cell. An isolated cell sample may be obtained through the use of a cell marker or a combination of cell markers, either of which is unique to one cell type in an unpurified cell sample. In some embodiments, the cells are isolated through the use of a cell sorter. In some embodiments, antibodies against cell proteins are used to isolate cells.

As used herein, the term "conjugate" refers to the association between atoms or molecules. The association can be direct or indirect. For example, a conjugate between a polymer and a ligand provided herein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the polymer is non-covalently attached to the ligand through a non-covalent chemical reaction between a component of the polymer and a component of the ligand. In other embodiments, the polymer includes one or more reactive moieties, e.g., a covalent reactive moiety, as described herein (e.g., alkyne, azide, maleimide or thiol reactive moiety). In other embodiments, the polymer includes a linker with one or more reactive moieties, e.g., a covalent reactive moiety, as described herein (e.g., alkyne, azide, maleimide or thiol reactive moiety).

Useful reactive moieties or functional groups (chemical reactive functional groups) used for conjugate chemistries (click chemistries) herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Chemical synthesis of compositions by joining small modular units using conjugate (click) chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stöckmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the proteins described herein. By way of example, the polymer or ligand can include a vinyl sulfone or other reactive moiety (e.g., maleimide). Optionally, the polymer or ligand can include a reactive moiety having the formula S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "polypeptide," "peptide" and "protein" are used interchangeably herein to refer to a polymer of amino acid residues, wherein the polymer may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. The terms apply to macrocyclic peptides, peptides that have been modified with non-peptide functionality, peptidomimetics, polyamides, and macrolactams. A "fusion protein" refers to a chimeric protein encoding two or more separate protein sequences that are recombinantly expressed as a single moiety.

The term "peptidyl" and "peptidyl moiety" means a monovalent peptide.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (www.ncbi.nlm.nih.gov). This algorithm involves first identifying high scoring sequence pairs (HSPs)

by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a ligand as described herein and a polymer. In embodiments contacting includes, for example, allowing a ligand as described herein to interact with a polymer.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells.

The term "polymer" or "polymers" as provided herein refers to synthetic or natural molecules, or macromolecules, composed of multiple repeated subunits (monomers). Synthetic polymers (e.g., synthetic plastics such as polystyrene) and natural biopolymers (e.g., DNA, proteins) may be distinguished. Polymers, both natural and synthetic, are created via polymerization of many small molecules, known as monomers. In embodiments, polymers have a large molecular mass relative to small molecule compounds and, therefore, produce unique physical properties (e.g., toughness, viscoelasticity, tendency to form glasses and semicrystalline structures). In embodiments, the polymers are charged (charged polymers). The charged polymers provided herein may include a positive charge or a negative charge. Thus, in embodiments, the charged polymer is an anionic polymer. In embodiments, the charged polymer is a cationic polymer. Non-limiting examples of polymers useful for the compositions and methods provided herein include gum arabic, gum acacia, gum tragacanth, locust bean gum, guar gum, hydroxypropyl guar, xanthan gum, talc, cellulose gum, *sclerotium* gum, carageenan gum, karaya gum, cellulose gum, rosin, methylcellulose, hydroxyethylcellulose, hydroxypropylcellulose, hydroxymethylcellulose, hydroxypropylmethylcellulose, methylhydroxyethylcellulose, cetyl hydroxyethylcellulose, carboxymethylcellulose, corn starch, hydroxypropyl starch phosphate, distarch phosphate, distarch dimethylene urea, aluminum starch octenyl succinate, maltodextrin, dextran, poly(acrylamide), PEG-150 distearate, PEG-150/decyl alcohol/SMDI copolymer, PEG-150/stearyl alcohol/SMDI copolymer, PEG-180/Laureth-50/TMMG copolymer, Polyether 1, acrylic acid/acrylamidomethyl propane sulfonic acid copolymer, acrylate/C10-30 alkyl acrylate cross polymer, acrylate/beheneth-25 methacrylate copolymer, acrylate/steareth-20 methacrylate copolymer, acrylate/steareth-20 copolymer, acrylate/VA cross polymer, acrylic acid/acrylonitrogen copolymer, ammonium acryloyldimethyltaurate/beheneth-25 methacrylate copolymer, ammonium acryloyldimethyltaurate/VP copolymer, sodium acrylate copolymer, PVM/MA decadiene cross polymer, alginic acid, propylene glycol alginate, dimethicone, silica dimethyl silylate, a dimethylacrylamide/acrylic acid/polystyrene ethyl methacrylate copolymer, PLGA polymer, polylactide, polyethylene glycol, carbomer, trolamine, derivatives thereof, and mixtures thereof. In embodiments, the polyethylene glycol is PEG3380. PEG3380 refers, in the customary sense, to CAS Registry No. 71767-64-1. In embodiments, the carbomer is Carbopol® 980. The term "carbomer" refers to cross linked polyacrylate polymers as known in the art and, for example, to Carbopol® 980 or Carbopol® 980 polymer, which are defined by CAS Registry Nos. 9063-87-0, 9003-01-4, or 600-07-7, respectively. The polyacrylate polymer may be, but is not limited to, poly-2-methylbutanoic acid, poly-prop-2-enoic acid, polyacrylic acid.

In embodiments, the polymer is a block polymer. In embodiments, the block polymer is a $Lysine_{14}$ block polymer. A $Lysine_{14}$ block polymer as provided herein refers to a polymer derived from two lysine homopolymer subunits (monomers), which are linked by covalent bonds.

A "solid support" as provided herein refers to any appropriate material that can be modified to contain discrete individual sites for the attachment or association of an electronically conductive polymer as provided herein including embodiments thereof and is amenable to the methods provided herein including embodiments thereof. Examples of solid supports include without limitation, glass and modified or functionalized glass (e.g., carboxymethyldextran functionalized glass), plastics (including acrylics, polystyrene and copolymers of styrene and other materials, polypropylene, polyethylene, polybutylene, polyurethanes, Teflon™, etc.), polysaccharides, nylon or nitrocellulose, composite materials, ceramics, and plastic resins, silica or silica-based materials including silicon and modified silicon (e.g., patterned silicon), carbon, metals, quartz (e.g., patterned quartz), inorganic glasses, plastics, optical fiber bundles, and a variety of other polymers (e.g., electronically conductive polymers such as poly-3,4-ethylenedioxythiophene, PEDOT). In general, the solid support allows optical detection and do not appreciably fluoresce. The solid support may be planar (e.g., flat planar substrates such as glass, polystyrene and other plastics and acrylics). Although it will be appreciated by a person of ordinary skill in the art that other configurations of solid supports may be used as well; for example, three dimensional configurations can be used. The solid support may be modified to contain discrete, individual sites (also referred to herein as "wells") for polymer binding. These sites generally include physically altered sites, i.e. physical configurations such as wells or small depressions in the substrate that can retain the polymers. The wells may be formed using a variety of techniques well known in the art, including, but not limited to, photolithography, stamping techniques, molding techniques and microetching techniques. It will be appreciated by a person of ordinary skill in the art that the technique used will depend on the composition and shape of the solid support. In embodiments, physical alterations are made in a surface of the solid support to produce wells.

The term "ligand" (also referred to herein as a ligand domain) refers to a composition (e.g., atom, molecule, ion, molecular ion, compound, particle, protein, peptide, nucleic acid) capable of binding (e.g. specifically binding) to a second ligand-binding composition (e.g., analyte, polymer, protein, marker) to form a complex. In embodiments, the ligand domain is included in a phage wrapper as described herein or may be included in a fusion protein also including a virus (e.g., phage) coat protein (e.g., a virus particle polymer ligand conjugate). A ligand as provided herein may without limitation bind to biomolecules (e.g., hormones, cytokines, proteins, nucleic acids, lipids, carbohydrates, cellular membrane antigens and receptors (neural, hormonal, nutrient, and cell surface receptors or their ligands)); whole cells or lysates thereof (e.g., prokaryotic (e.g., pathogenic bacteria), eukaryotic cells (e.g., mammalian tumor cells); viruses (e.g., retroviruses, herpesviruses, adenoviruses, lentiviruses and spores); chemicals (e.g., solvents, polymers, organic materials, small molecules); therapeutic molecules (e.g., therapeutic drugs, abused drugs, antibiotics); environmental pollutants (e.g., pesticides, insecticides, toxins).

As used herein, the terms "specific binding" or "specifically binds" refer to two molecules forming a complex (e.g., phage with ligand expressed by phage or included in phage wrapping specifically binding a protein that binds the ligand) that is relatively stable under physiologic conditions.

Methods for determining whether a ligand binds to a protein and/or the affinity for a ligand to a protein are known in the art. For example, the binding of a ligand to a protein can be detected and/or quantified using a variety of techniques such as, but not limited to, Western blot, dot blot, surface plasmon resonance method (e.g., BIAcore system; Pharmacia Biosensor AB, Uppsala, Sweden and Piscataway, N.J.), isothermal titration calorimetry (ITC), or enzyme-linked immunosorbent assays (ELISA).

Immunoassays which can be used to analyze immuno-specific binding and cross-reactivity of the ligand include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, and fluorescent immunoassays. Such assays are routine and well known in the art.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms "variable heavy chain," "$V_H$," or "VH" refer to the variable region of an immunoglobulin heavy chain, including an Fv, scFv, dsFv or Fab; while the terms "variable light chain," "$V_L$" or "VL" refer to the variable region of an immunoglobulin light chain, including of an Fv, scFv, dsFv or Fab.

Examples of antibody functional fragments include, but are not limited to, complete antibody molecules, antibody fragments, such as Fv, single chain Fv (scFv), complementarity determining regions (CDRs), VL (light chain variable region), VH (heavy chain variable region), Fab, F(ab)2' and any combination of those or any other functional portion of an immunoglobulin peptide capable of binding to target antigen (see, e.g., FUNDAMENTAL IMMUNOLOGY (Paul ed., 4th ed. 2001). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., (1990) *Nature* 348:552). The term "antibody" also includes bivalent or bispecific molecules, diabodies, triabodies, and tetrabodies. Bivalent and bispecific molecules are described in, e.g., Kostelny et al. (1992) *J. Immunol.* 148:1547, Pack and Pluckthun (1992) *Biochemistry* 31:1579, Hollinger et al. (1993); *PNAS. USA* 90:6444, Gruber et al. (1994) *J Immunol.* 152:5368, Zhu et al. (1997) *Protein Sci.* 6:781, Hu et al. (1996) *Cancer Res.* 56:3055, Adams et al. (1993) *Cancer Res.* 53:4026, and McCartney, et al. (1995) *Protein Eng.* 8:301.

In another embodiment, provided herein are articles of manufacture or kits containing diagnostic compositions including an effective amount of any of the compositions described herein (e.g. viral particle, phage, phage wrappers, ligands, constructs for expressing ligands fused to coat proteins) and instructions for their use in the methods described herein. In another aspect, the disclosure features a diagnostic or monitoring kit including: (i) any of the compositions described herein or (ii) any of the constructs (e.g. coat protein ligand fusions) described herein.

The term "diagnosis" refers to a relative probability that a disease (e.g. cancer, urinary tract infection, infection, or other disease) is present in the subject. Similarly, the term "prognosis" refers to a relative probability that a certain future outcome may occur in the subject with respect to a disease state. For example, in the context of the present invention, prognosis can refer to the likelihood that an individual will develop a disease (e.g. cancer, urinary tract infection, infection, or other disease), or the likely severity of the disease (e.g., duration of disease). The terms are not intended to be absolute, as will be appreciated by any one of skill in the field of medical diagnostics.

As used herein, an "effective amount" or "diagnostically effective amount" of a composition described herein is an amount sufficient to produce a clinically useful characterization or measurement of a disease state, such as an infection or cancer, (e.g. in an individual, patient, human, mammal, clinical sample, tissue, biopsy). A clinically useful characterization or measurement of a disease state, such as an infection or cancer, (e.g. in an individual, patient, human, mammal, clinical sample, tissue, biopsy) is one containing sufficient detail to enable an experienced clinician to assess the degree and/or extent of disease for purposes of diagnosis, monitoring the efficacy of a therapeutic intervention, and the like.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g. hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer. In embodiments, the cancer is prostate cancer.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

Compositions

M13 bacteriophage, or more commonly "phage", serve as receptors and platforms to present receptors for the biosensors described herein. Viruses that infect only bacteria, the M13 bacteriophage have a readily customized protein coat, which can be tailored to bind to cancer biomarkers.[13] The M13 viruses have ssDNA encapsulated by approximately 2700 copies of the major coat protein (P8) and five copies each of the four minor coat proteins. Manipulating the encapsulated DNA can provide peptides and proteins fused to the phage coat proteins, which are displayed on the phage surface.' Combinatorial engineering of such polypeptides allows molecular evolution to obtain displayed ligands with specific binding affinities and specificities.[14,15]

For direct electrical detection of biomarkers, M13 bacteriophage have been incorporated into films of an electronically conductive polymer, poly-3,4-ethylenedioxythiophene (PEDOT).[16-20] Synthesis of the biosensor film is accomplished by electropolymerizing EDOT on the surface of a planar gold electrode from a solution that contains virus particles. For biosensing studies, phage-displayed ligands are incorporated into a bioaffinity matrix composed of a synthetic organic polymer PEDOT. The change in resistance observed upon analyte binding is directly proportional to the analyte concentration.

During biosensor measurements, the electrochemical impedance of the virus-PEDOT film increases upon exposure to the biomarker, providing a quantifiable readout for analyte binding.[21] Modifications to the biosensing films could further improve the device's limit of detection (LOD) for translational relevance. Conventional phage display results in a low density of genetically encoded ligands displayed on the surface of the phage. Described herein are methods of increasing the density of ligands, as a strategy for more-sensitive measurements with higher signal-to-noise ratios. The concept of "phage wrapping" to improve ligand density and/or prevent nonspecific binding to the phage are described herein.[23,24] The approach takes advantage of the presence of negatively charged residues, one Glu and two Asp, on the N-terminus of each P8. Since each phage includes 2700 copies of P8, such carboxylate-bearing residues result in a high negative charge on the outer surface of the virus particle.[25] As described herein, additional ligands wrapped onto the phage surface due to this electrostatic interaction lead to enhanced affinity and selectivity for PSMA.

Described herein is a bioaffinity matrix of viruses integrated into PEDOT films for electrochemical sensing of markers (e.g. PSMA, a prostate cancer biomarker). High sensitivity to PSMA resulted from synergistic action by two different ligands to PSMA on the same phage particle. One ligand was genetically encoded, and the secondary recognition ligand was chemically synthesized to wrap around the phage. The dual ligands result in a bidentate binder with high-copy, dense ligand display for enhanced PSMA detection through a chelate-based avidity effect. Biosensing with virus-PEDOT films provides a 100 pM limit of detection for PSMA in synthetic urine without requiring enzymatic or other amplification.

The wrapping technique described herein maximizes the density of ligands present on the surface of the phage. As a result, higher sensitivity can be obtained without modifying the architecture of the device, or compromising any other aspect to achieve the same. The technique is easy to perform, and the reaction is performed in aqueous media, which does not disrupt the function of the biological molecules present on the phage.

In the case of phage wrapping performed with oligolysine-alkyne, the new approach allows the linkage of molecules of much bigger sizes (such as PEG) as compared to oligolysine (e.g., 3 to 20 lysine, 4 to 19 lysine, 5 to 18 lysine, 6 to 17 lysine, 7 to 17 lysine, 8 to 16 lysine, 9 to 16 lysine, 10 to 15 lysine, 11 to 14 lysine, 12 to 14 lysine, 13 to 14 lysine, 14 lysine). Wrapping the phage surface first with the oligolysine half allows the attachment of any sized molecule to the alkyne or otherwise functionalized oligolysine. It also opens up ways to wrap the phage surface with a pre-defined ratio of mixed wrappers by modifying the linking chemistry, from example alkyne-azide cycloaddition or thiol-maleimide addition. The latter can be easily achieved by synthesizing oligolysine-cysteine. In embodiments, PEG is attached non-covalently to the surface of viruses in <1 h, and the resultant non-specific adhesion is explored for phage versus cell applications.

An important usage of this technique is maximization of ligand density on the surface of the phage, which in turn leads to enhancement in the sensitivity of measurement. A similar approach could be applied to prevent non-specific binding of viruses to any surface, such as in the case of targeting mammalian cells. The approach could be used for targeting any protein (e.g. as long as the sequence of the ligands is known).

The phage-PEDOT film with PEI wrapper is a novel interface for an *E. coli* biosensor. The electrochemical impedance of the film is measured before and after exposure to *E. coli*. The signal is calculated as the change in the impedance after binding of *E. coli* to the surface of the film. This biosensor has applications in the medical field (e.g. for the purpose of detection of urinary tract infections as well as detecting bacterial contamination in the food and pharmaceutical industries).

In an aspect is provided a whole viral particle including a charged protein coat, the charged protein coat comprising a charged coat protein electrostatically bound to a functionalized charged polymer or a charged polymer conjugate, wherein the functionalized charged polymer includes a charged polymer covalently bound to a chemically reactive functional group, and wherein the charged polymer conjugate includes a charged polymer covalently bound to a hydrophilic organic polymer.

In another aspect, a whole viral particle is provided. The whole viral particle includes a charged protein coat, the charged protein coat includes a charged coat protein electrostatically bound to a functionalized charged polymer, wherein the functionalized charged polymer includes a charged polymer covalently bound to a chemically reactive functional group.

In one aspect, a whole viral particle is provided. The whole viral particle includes a charged protein coat, the charged protein coat includes a charged coat protein electrostatically bound to a charged polymer conjugate, wherein the charged polymer conjugate includes a charged polymer covalently bound to a hydrophilic organic polymer. In embodiments, the hydrophilic organic polymer is a polyethylene glycol.

In embodiments, the charged coat protein is a negatively charged coat protein. In embodiments, the charged coat protein is a positively charged coat protein. In embodiments, the charged coat protein includes one or more negatively charged amino acid residues. In embodiments, the charged coat protein includes one or more Glu or one or more Asp residues.

In embodiments, the charged coat protein includes one or more Glu and one or more Asp residues. In embodiments, the one or more Glu or one or more Asp residues form part of the N-terminus of the charged coat protein. In embodiments, the charged coat protein is P8.

The term "P8" or "P8 protein" as provided herein includes any of the recombinant or naturally-occurring forms of the viral coat protein P8 or variants or homologs thereof that maintain P8 protein activity (e.g. within at least 50%, 80%, 90%, 95%, 96%, 97%, 98%, 99% or 100% activity compared to P8). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring P8 polypeptide. In embodiments, P8 is the protein as identified by the NCBI sequence reference GI:402239556, homolog or functional fragment thereof.

In embodiments, the charged polymer is a cationic polymer. In embodiments, the charged polymer is an anionic polymer. Where the charged coat protein is electrostatically bound to a functionalized charged polymer, the charged coat protein and the functionalized charged polymer are connected through an ionic bond.

In embodiments, the chemically reactive functional group is a click chemistry reactive functional group. In embodiments, the click chemistry reactive functional group is an alkyne or an azide. In embodiments, the click chemistry reactive functional group is a thiol or a maleimide. In embodiments, the chemically reactive functional group is a bioorthogonal chemically reactive functional group. A "bioorthogonal chemically reactive functional group" refers to any chemically reactive functional group that can react inside of living systems without interfering with native biochemical processes.

In embodiments, the whole viral particle is a whole bacteriophage viral particle. In embodiments, the whole viral particle is an M13 virus particle. In embodiments, the charged coat protein includes a genetically encoded ligand. In embodiments, the charged polymer is oligolysine (e.g. 3 to 20 lysine, 4 to 19 lysine, 5 to 18 lysine, 6 to 17 lysine, 7 to 17 lysine, 8 to 16 lysine, 9 to 16 lysine, 10 to 15 lysine, 11 to 14 lysine, 12 to 14 lysine, 13 to 14 lysine, 14 lysine). In embodiments, polyethylene glycol ("PEG") may have a molecular weight ranging from PEG100 to PEG5000, from PEG 500 to PEG5000, from PEG1000 to PEG5000, or from PEG2000 to PEG4000. In embodiments, the PEG is PEG100, PEG200, PEG300, PEG400, PEG500, PEG600, PEG700, PEG800, PEG900, PEG1000, PEG1500, PEG2000, PEG2500, PEG3000, PEG3500, PEG4000, PEG4500, or PEG5000.

In an aspect is provided a cationic electronically conductive polymer electrostatically bound to a first whole viral particle, the first whole viral particle including a negatively charged protein coat wherein the negatively charged protein coat comprises a coat protein electrostatically bound to a cationic polymer or a cationic polymer conjugate.

In embodiments, the negatively charged protein coat comprises a coat protein electrostatically bound to a cationic polymer. In embodiments, the negatively charged protein coat includes a mixture of wild-type coat protein and coat protein fused to a genetically encoded ligand. In embodiments, the cationic polymer is electrostatically bound to a second whole viral particle. In embodiments, the cationic polymer is polyethylene imine. In embodiments, the second whole viral particle includes a second genetically encoded ligand. In embodiments, the second genetically encoded ligand is different from the first genetically encoded ligand. In embodiments, the second genetically encoded ligand is identical to the first genetically encoded ligand. In embodiments, the cationic electronically conductive polymer is PEDOT. In embodiments, the cationic electronically conductive polymer is bound to a solid support. In embodiments, the solid support is gold. In embodiments, the cationic electronically conductive polymer is part of a biosensor device. In embodiments, the cationic polymer conjugate includes a functionalized charged polymer covalently bound to a functionalized ligand. In embodiments, the cationic polymer is oligolysine. In embodiments, the cationic polymer conjugate includes oligolysine.

In embodiments, the whole viral particle is a whole viral particle described herein, including in embodiments and examples. In embodiments, the cationic electronically conductive polymer is a cationic electronically conductive polymer described herein, including in embodiments and examples.

Methods

Disclosed herein is the use of a technique termed 'phage wrapping' to modulate binding by phage-displayed ligands. Additional ligands can be wrapped onto the phage surface through charge-charge interactions between positively charged peptides or polymers and the negatively charged phage coat. This principle is applied to control phage binding, either by increasing it through avidity effects from additional ligands or phage, or through decreasing surface non-specificity.

In one embodiment, enhanced binding results from ligands linked to an oligolysine peptide that wraps around the phage surface due to electrostatic interactions. This principle is demonstrated by targeting with phage-displayed ligands prostate-specific membrane antigen (PSMA), a cancer biomarker. Incorporating viruses into the bioaffinity matrix, virus-PEDOT, polymeric film of biosensors for targeting PSMA previously displayed low copy number of the genetically displayed ligands on the surface of the phage and served as a limitation to the detection PSMA. The low copy number lead to a limit of detection which was not sufficient for the detection of PSMA. Wrapping phage with additional ligands provided the solution, and a 100 pM limit of detection was achieved for PSMA. For biosensing with virus-PEDOT films, the films can be incubated with a solution of the wrapper to provide additional ligands to wrap the phage surface.

Figure 9:
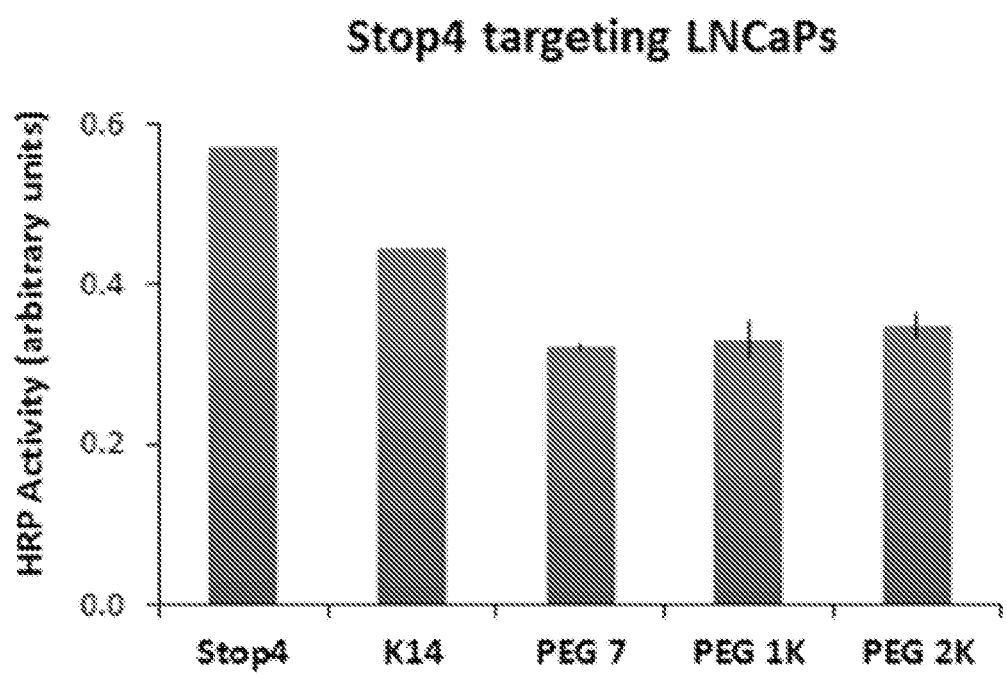
FIG. 9. Phage-based ELISA. Phage-based ELISA demonstrates the effectiveness of ligand wrapping to reduce non-specific binding affinity through blocking with PEG (polyethylene glycol). K14/PEG 7/PEG 1K/PEG 2K represents Stop4 phage wrapped with neat oligolysine, or oligolysine linked to PEG 7, or PEG 1000 ($M_n$), or PEG 2000 ($M_n$) respectively, used to prevent non-specific binding to LNCaP cells.
Figure 10:
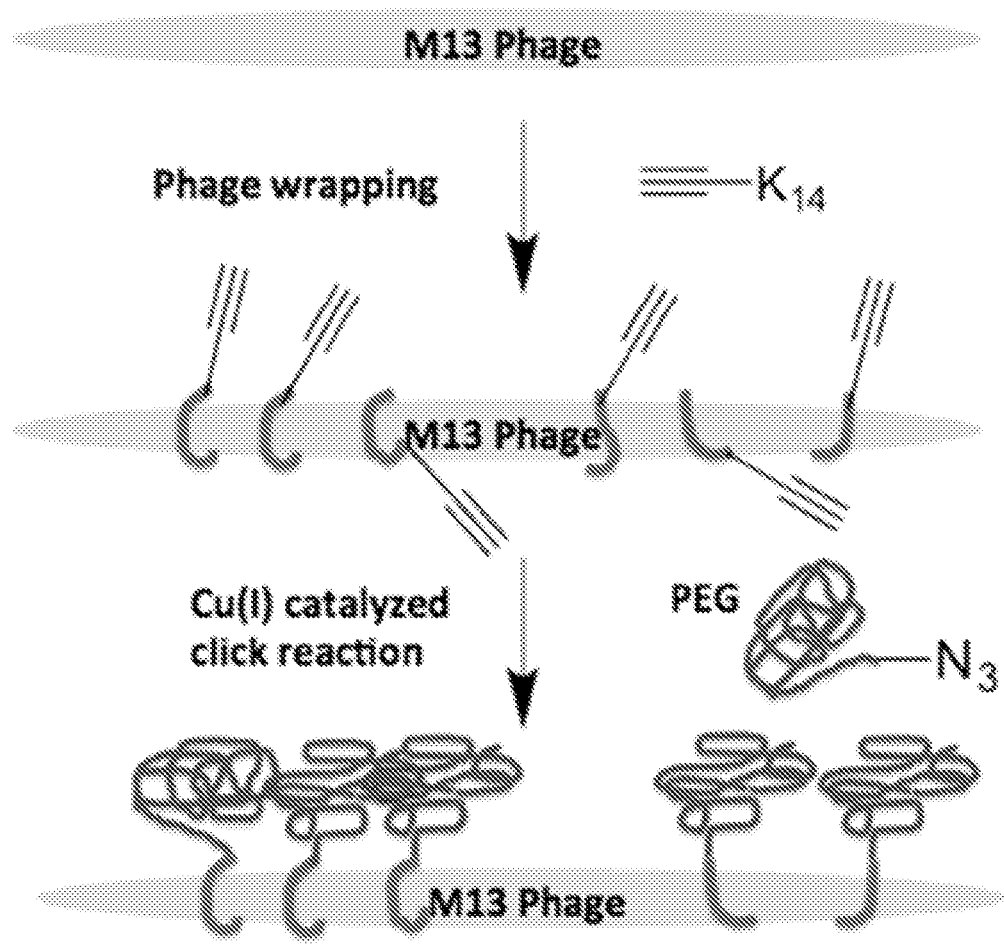
FIG. 10. depicts cartoon of wrapping phage with oligolysine-alkyne to avoid encapsulation of oligolysine by larger groups forming the full wrapper. Subsequently, click reaction on the phage surface provides the wrappers with PEG covering the surface to prevent non-specific binding to cells.

In another embodiment, the approach was applied to decrease non-specific binding to the phage surface. To achieve this, the phage surface can be covered with polyethylene glycol (PEG) or other polymer known to disrupt non-specific binding interactions. For example, PEG functionalized with an azide group is linked to an oligolysine peptide using a click chemistry reaction, as described herein. Subsequently, the PEG-oligolysine conjugate is used for wrapping the phage. To overcome problems associated with blocking of the oligolysine wrapper, phage particles can first be wrapped with the oligolysine-alkyne before the click reaction with the PEG-azides (FIG. 10). This approach results in an almost 50% reduction in non-specific binding of phage to LNCaP cells, a prostate cancer cell line (FIG. 9). Non-specific binding to cells is a commonly observed problem in the field of cell sensing. PEG wrappers of varying lengths were used to prevent the non-specific binding affinity. But the large size of PEG in comparison to oligolysine prevented wrapping on the phage surface by the oligolysine half. The problem could be interpreted as PEG completely encapsulating the oligolysine half, thus rendering it unavailable for wrapping the phage surface. The problem was solved by first wrapping the phage surface with oligolysine peptide functionalized with an alkyne group. Copper (I) catalyzed cycloaddition (click) was subsequently used to link the oligolysine to PEG functionalized with an azide group. Three different lengths of PEG were used. The decrease in non-specific binding was almost in the same range irrespective of the length of PEG used. Additional lengths of PEG may be used.

Figure 11:
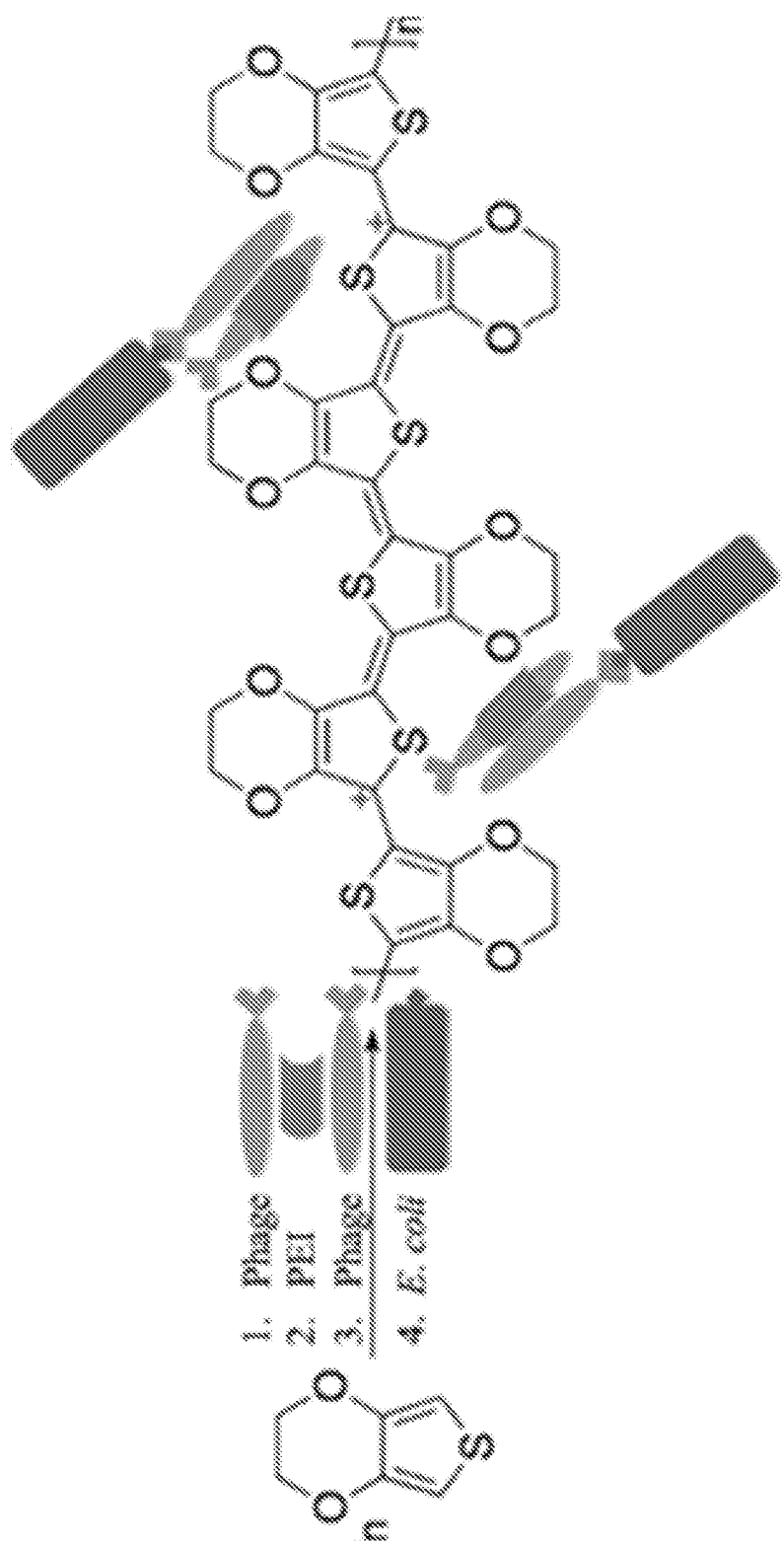
FIG. 11. Schematic demonstrating the incorporation of phage into a PEDOT film via electro-polymerization. The concentration of phage particles incorporated in the film are increased by using PEI as wrappers. The process allows for increased *E. coli* capture.
Figure 12:
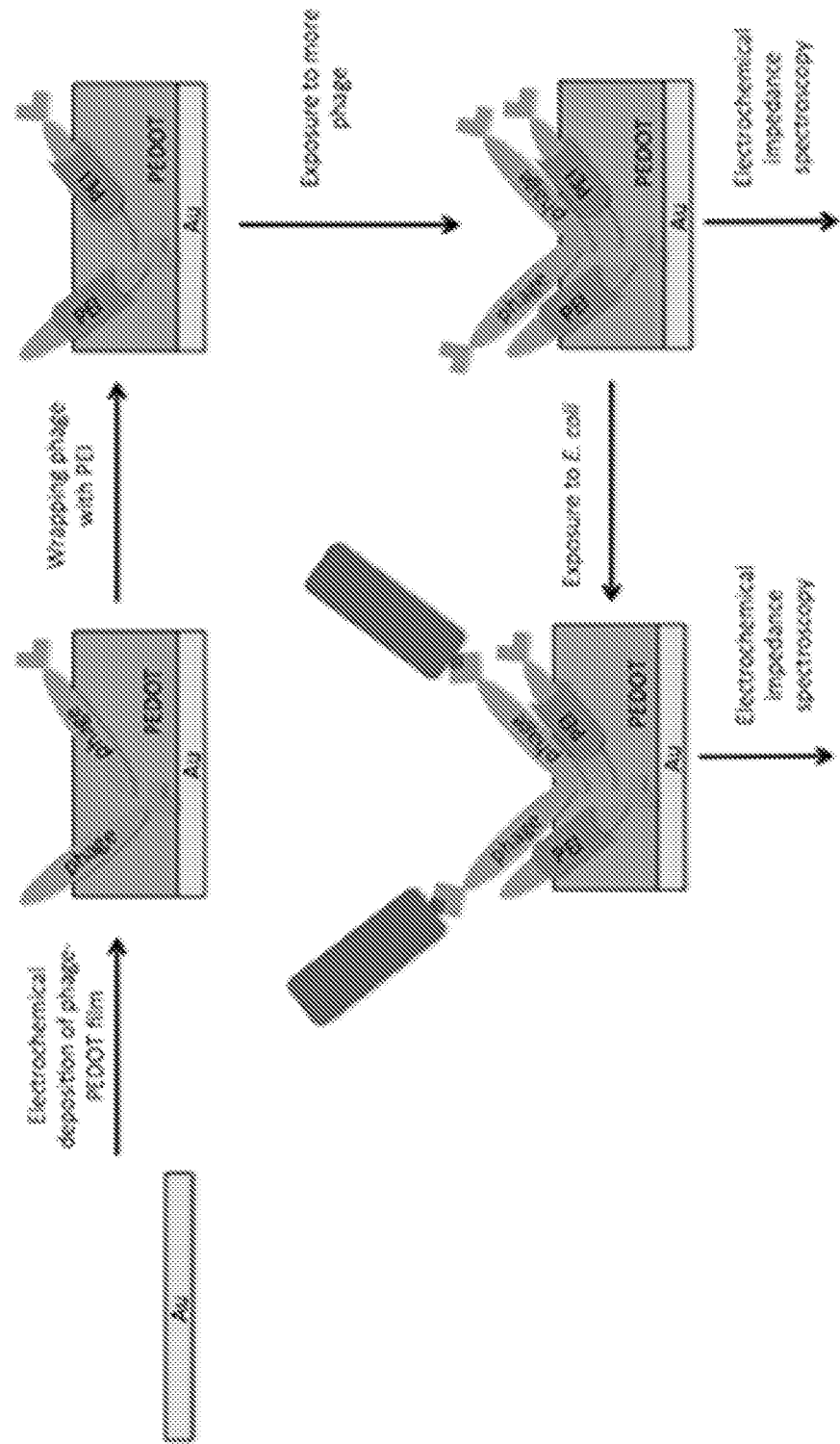
FIG. 12. Schematic illustrating the process of *E. coli* detection using PEI wrappers.
Figure 13:
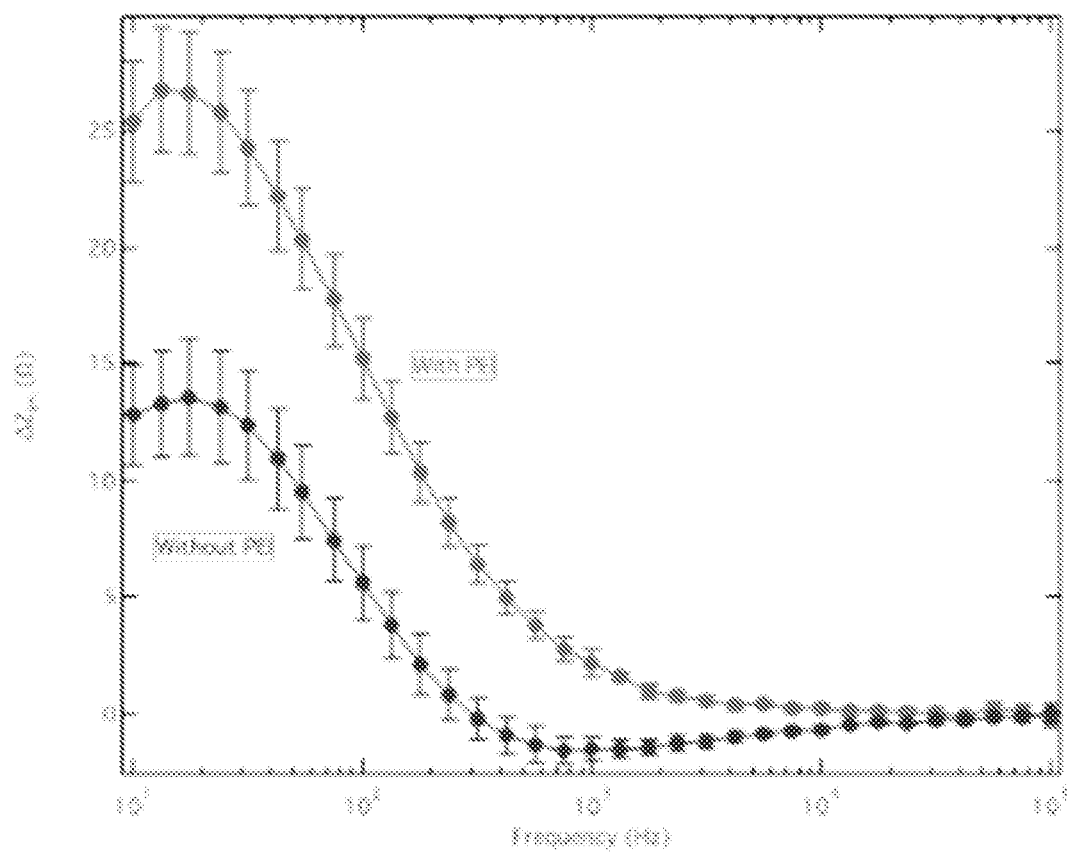
FIG. 13. Plot of $\Delta Z_{im}$ vs. frequency for virus-PEDOT films. Both films were electropolymerized on the surface of a gold electrode using 3 nM phage in a solution of 2.5 mM EDOT and 12.5 mM LiClO$_4$. The film with PEI was exposed to 50 µM PEI for one hour, followed by exposure to 32 nM phage for 30 min. The two films were exposed to 7×10$^3$ CFU/mL XL1 *E. coli* cells in LB media for 30 minutes. The impedance measurements were made in LB media. Five impedance measurements were averaged to obtain the error bars, which indicate ±1σ.

Another embodiment increases the density of phage and potentially phage-displayed ligands by linking phage particles using polyethylene imine (PEI). In a further embodiment, improving the sensitivity of biosensors for $E.$ $coli$, was obtained by wrapping M13 bacteriophage (phage) with polyethyleneimine (PEI) to enhance binding to the target $E.$ $coli$, for early detection of urinary tract infection. This is performed by exposing phage containing films of 3, 4-polyethylenedioxythiophene (PEDOT) prepared on the surface of a planar gold electrode, with PEI, followed by exposure to high phage concentration. This protocol results in a double layer of phage sandwiched by PEI (FIGS. 11, 12). In this embodiment, the positive charges of PEI cause the material to adhere to the phage. Further incubation of the PEI-virus film with additional phage can then allow more phage to bind to the film surface due to electrostatic interactions. The resultant higher density phage film has greater affinity for $E.$ $coli$, resulting in a more sensitive biosensor response to detect the bacteria (FIG. 13).

Using PEI as a wrapper allows for increased capture of $E.$ $coli$ cells, leading to increased signal from the virus-PEDOT films. Use of these techniques may include biosensor based detection devices for prostate cancer, urinary tract infection, or other diagnostic uses.

In an aspect is provided a method of reducing non-specific binding of whole viral particles to cells including the step of electrostatically binding a functionalized charged polymer or a charged polymer conjugate to the whole virus particle; wherein the functionalized charged polymer includes a charged polymer covalently bound to a chemically reactive functional group, and wherein the charged polymer conjugate includes a charged polymer covalently bound to a hydrophilic organic polymer.

In an aspect is provided a method of improving the sensitivity of a sensor, wherein the method includes increasing the ligand density of the sensor through phage wrapping. In embodiments, the method includes electrostatically binding a functionalized charged polymer or a charged polymer conjugate to a charged coat protein of a whole viral particle of the sensor, wherein the functionalized charged polymer includes a charged polymer covalently bound to a chemically reactive functional group or the functionalized charged polymer includes ligand.

In an aspect is provided a method of improving the sensitivity of a bacterial biosensor, wherein the bacterial biosensor includes a cationic electronically conductive polymer electrostatically bound to a first whole viral particle, and the method includes electrostatically binding a negatively charged coat protein of the whole viral particle to a cationic polymer. In an embodiment, the cationic polymer is polyethylene imine.

In an aspect is provided a method of detecting a biological molecule, the method including: (i) combining a whole viral particle described herein or a cationic electronically conductive polymer described herein and a biological molecule to a reaction vessel; (ii) allowing the whole viral particle or the cationic electronically conductive polymer to specifically bind to the biological molecule; and (iii) detecting the bound biological molecule.

In embodiments, the whole viral particle or the cationic electronically conductive polymer specifically binds to the biological molecule to form a bound cell surface protein. In embodiments, the biological molecule is a cell surface protein, a soluble protein, or a proteolytically released ectodomain of a protein. In embodiments, the cell surface protein forms part of a cell. In embodiments, the cell is a bacterial cell. In embodiments, the bacterial cell is an $E.$ $coli$ cell. In embodiments, the whole viral particle and the cationic electronically conductive polymer are capable of binding to the cell surface protein at least 50% (e.g. at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%) more specifically than a whole viral particle without a functionalized cationic or anionic polymer, charged polymer conjugate, or cationic electronically conductive polymer, respectively. In embodiments, the reaction vessel forms part of a biosensing device. In embodiments, the combining is performed in aqueous media. In embodiments, the detecting is accomplished by measuring electrochemical impedance. In embodiments, the biological molecule is obtained from a patient sample. In embodiments, the patient sample is obtained from a patient suspected of having cancer. In embodiments, the patient sample is obtained from a patient suspected of having a carcinoma. In embodiments, the patient sample is obtained from a patient suspected of having a sarcoma. In embodiments, the patient sample is obtained from a patient suspected of having lymphoma. In embodiments, the patient sample is obtained from a patient suspected of having leukemia. In embodiments, the patient sample is obtained from a patient suspected of having a solid tumor. In embodiments, the patient sample is obtained from a patient suspected of having myeloma. In embodiments, the patient sample is obtained from a patient suspected of having a hematological cancer. In embodiments, the patient sample is obtained from a patient suspected of having prostate cancer. In embodiments, the patient sample is obtained from a patient suspected of having a urinary tract infection. In embodiments, the detecting indicates the presence or absence of a urinary tract infection in said patient.

In embodiments, the method of detecting a biological molecule is a method described herein, including in embodiments or examples.

In another aspect, a method of forming a virus particle polymer ligand conjugate is provided. The method includes contacting a first functionalized charged polymer with a charged virus coat protein, wherein the first functionalized charged polymer is covalently bound to a first chemically reactive functional group, thereby forming a virus particle polymer conjugate. The first chemically reactive functional group of the virus particle polymer conjugate is contacted with a second chemically reactive functional group covalently bound to a second polymer, wherein the second polymer is covalently linked to a ligand domain, thereby forming a virus particle polymer ligand conjugate.

In embodiments, the contacting of step (i) includes electrostatically binding the first functionalized charged polymer to the charged virus coat protein. Where the charged coat protein is electrostatically bound to the functionalized charged polymer, the charged coat protein and the functionalized charged polymer may be connected through an ionic bond. The charged virus coat protein may be a P8 protein. The charged virus coat protein may be positively charged. The charged virus coat protein may be negatively charged.

In embodiments, the first functionalized charged polymer is a cationic polymer. In embodiments, the first functionalized charged polymer is an anionic polymer. In embodiments, the first functionalized charged polymer is positively charged and the charged virus coat protein is negatively charged. In embodiments, the first functionalized charged polymer is negatively charged and the charged virus coat protein is positively charged. In embodiments, the first functionalized charged polymer is oligolysine. In embodiments, the first functionalized charged polymer is oligolysine-cysteine. A oligolysine-cysteine is an oligolysine covalently bound to a cysteine. In embodiments, the first chemically reactive functional group is a click chemistry reactive functional group. In embodiments, the click chemistry reactive functional group is an alkyne or an azide. In embodiments, the click chemistry reactive functional group is a thiol or a maleimide. In embodiments, the chemically reactive functional group is a bioorthogonal chemically reactive functional group. In embodiments, the first chemically reactive functional group forms part of a first linker.

The virus particle polymer conjugate formed in step (i) of the method provided herein is connected to a second polymer covalently attached to a ligand domain by reacting the first chemically reactive functional group (e.g., thiol) with a second chemically reactive functional group of the second polymer. In embodiments, the second functionalized charged polymer is a cationic polymer. In embodiments, the second functionalized charged polymer is an anionic polymer. In embodiments, the second polymer is polyethylene glycol. In embodiments, the second chemically reactive functional group is a click chemistry reactive functional group that is complementary to the first chemically reactive functional group. In embodiments, the click chemistry reactive functional group is an alkyne or an azide. In embodiments, the click chemistry reactive functional group is a thiol or a maleimide. The second chemically reactive functional group may be maleimide. In embodiments, the chemically reactive functional group is a bioorthogonal chemically reactive functional group. In embodiments, the second chemically reactive functional group forms part of a second linker.

The second polymer may include a third chemically reactive functional group covalently attaching the second polymer to the ligand domain. In embodiments, the third chemically reactive functional group is an amine. In embodiments, the third chemically reactive functional group is an alkyne. In embodiments, the third chemically reactive functional group forms part of a third linker. In embodiments, the ligand domain includes a forth chemically reactive functional group covalently binding the third chemically reactive functional group of the second polymer. In embodiments, the forth chemically reactive functional group forms part of a forth linker. In embodiments, the forth chemically reactive functional group is an azide.

In embodiments, the chemically reactive functional groups provided herein (e.g., first, second and third chemically reactive functional group) react to form part of a covalent linker (e.g., first, second and third linker). A linker as referred to herein may include the resulting linker formed by reacting two reactive groups (moieties), e.g., a covalent reactive group, as described herein (e.g., alkyne, thiol, azide, maleimide). In embodiments, the covalent linker is a 1,3 triazole linker (i.e. a linker comprising a 1,3-triazolene linker moiety, e.g. in combination with alkyl (substituted or unsubstituted), amide, ester, sulfonamide and the like including combinations thereof)). The linkers provided herein may be covalently attached to the charged polymer provided herein applying methods well known in the art and compatible with the composition of the linker and the polymer. The linkers provided herein may include the conjugated product of reactive groups at the point of attachment to the polymer. Thus, the linkers provided herein may be polyvalent and may be formed by conjugate chemistry techniques. Non-limiting examples of linkers useful for the compositions and methods provided herein are linkers that include alkyl groups (including substituted alkyl groups and alkyl groups containing heteroatom moieties and short alkyl groups), ester, amide, amine, epoxy groups and ethylene glycol or derivatives thereof. The linkers provided herein may include a sulfone group, forming sulfonamide, an ester group or an ether group (e.g., triethyl ether).

In one embodiment, the first functionalized charged polymer is oligolysine-cysteine and the first chemically reactive functional group is thiol. In a further embodiment, the second chemically reactive functional group is maleimide and the second polymer is PEG. In a further embodiment, the third chemically reactive functional group is alkyne and the forth chemically reactive functional group is azide.

In one embodiment, the first functionalized charged polymer is oligolysine-cysteine and the first chemically reactive functional group is thiol. In a further embodiment, the second chemically reactive functional group is maleimide and the second polymer is PEG. In a further embodiment, the third chemically reactive functional group is amine and the forth chemically reactive functional group is carboxylate.

EXAMPLES

1. Genetically Encoded, Phage-Displayed Ligands Targeting PSMA.

The two forms of PSMA, monomeric and dimeric, offer different targets for ligand binding; the dimeric form is overexpressed by prostate cancer cells, and the monomeric form offers a closely matched negative control for nonspecificity, as a protein only found in healthy prostate cells.[9] The relative binding affinities of two previously reported phage displayed ligands,[22] phage-1 and phage-2 (sequences and nomenclature in Table 1), for the PSMA isoforms were first examined by ELISA (FIG. 1). Phage-2 binds with higher affinity to the PSMA dimer than phage-1. Neither phage displayed ligand binds with significant affinity to the PSMA monomer. Thus, the peptide ligands selectively bind the dimeric form of PSMA. The specificity of phage-displayed ligands for the dimeric PSMA is critical for potential clinical applications. Additional negative controls include phage displayed peptides targeting the blocking agent (bovine serum albumin, BSA) and Stop-4 phage targeting PSMA; the latter phage includes an analogous phagemid packaged into phage without ligands displayed on their surfaces. The negative controls failed to show any significant binding. The two PSMA ligands, 1 and 2; provide a starting point for the development of biosensors. For translational relevance, the LOD of the resultant biosensor must be <0.25 nM, and a high signal-to-noise ratio is essential for definitive diagnosis. In theory, the affinity of the ligands for their target analyte should correlate with their usefulness in biosensor applications. For example, a higher affinity ligand could enhance sensitivity for the analyte.

Nature applies evolution-guided affinity maturation but also relies on another approach for more-rapid affinity maturation. The immune system, for example, applies the principle of avidity to boost the apparent affinity of a weaker initial lead. During the initial immune response, the IgM protein presents receptors in a decavalent format, allowing weak initial binders to attain higher apparent affinity through proximity- and chelate-based avidity.[26] The large phage surface with repetitive structural motifs appears well-suited to this approach, and, indeed, avidity effects are often present during phage-based selections and screens.' This concept could provide a generalized method for expedient improvement of ligand affinity and biosensor sensitivity.

2. Cycloaddition to Generate the Secondary Recognition Ligand.

To exploit this avidity effect, phage wrapping was used to boost ligand density, subsequent affinity, the resultant sensitivity, and the signal-to-noise ratio of phage-based biosensors. Each "wrapper" consists of two parts linked together by the $Cu^I$-catalyzed azide-alkyne cycloaddition ("click") reaction (Scheme 1).[28] The first component, an oligolysine (e.g. $K_{14}$) peptide, provides affinity to the phage surface. For the click reaction, an alkyne (e.g. 4-pentynoic acid) was coupled to the N-terminus of the $K_{14}$ peptide. The second component of the wrapper is the peptide ligand to PSMA. In previous studies, the PSMA-binding peptides, 1 and 2, exhibited limited solubility in water. The peptides were therefore synthesized as fusions to the solubilizing peptide sequence $K_3$ on their N-termini. For the click reaction, the N-termini of the peptide ligands were coupled to an azide (e.g. 4-azidobutanoic acid).

Figure 2:
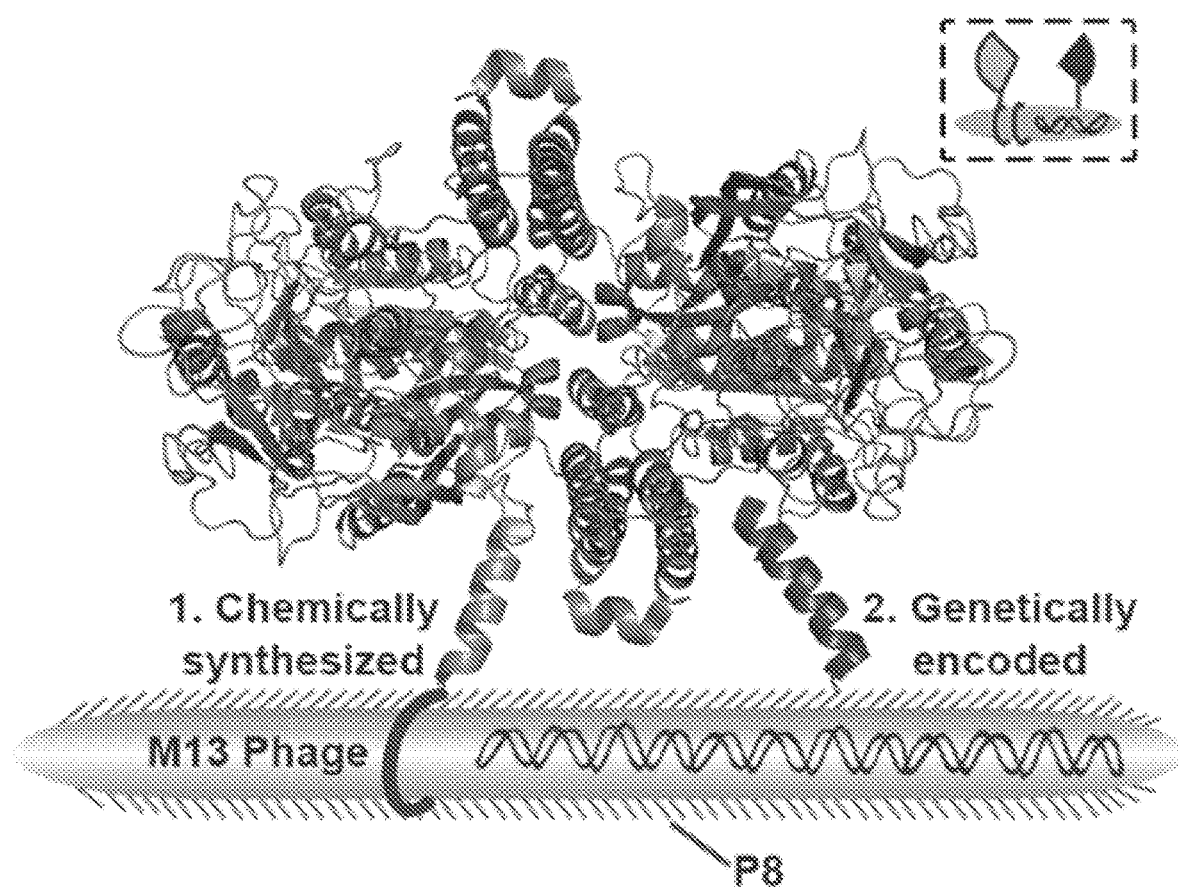
FIG. 2. Schematic cartoon diagram of bidentate binding to PSMA by chemically synthesized ($k_{CS}$-1, left) and genetically encoded (peptide 2, right) ligands to psma (pdb: 1Z8L). The former ligand wraps non-covalently onto the negatively charged P8 proteins found on the phage surface due to interactions with the positively charged $K_{14}$ peptide (depicted as a loop wrapped around M13 Phage). Simultaneous binding by the two ligands provides higher apparent affinity to PSMA. The inset depicts a simplified version of the schematic appearing in the subsequent figures shown here.

The two parts of each wrapper were chemically synthesized using solid-phase peptide synthesis and purified by reverse-phase HPLC before the cycloaddition reaction. Here, click chemistry offers a convergent synthesis, and the reaction takes place at room temperature and in aqueous solution.[28] The resultant secondary recognition ligands thus provide an oligolysine half to wrap the phage (termed $K_{CS}$ for "lysine, chemically synthesized") and a second component, the PSMA ligand (1 or 2), to bind to the analyte (FIG. 2). The products formed by the click reaction ($K_{CS}$-1 or $K_{CS}$-2) were characterized by MALDI-TOF MS and purified by reverse-phase HPLC to an estimated 90% purity.

TABLE 1

PSMA Ligands, Sequence, and Nomenclature

| X | Amino acid sequence | Genetically encoded | Chemically synthesized | Structure of the chemically synthesized peptide |
|---|---|---|---|---|
| 1 | CALCEFLG (SEQ ID NO: 1) | phage-1 | $K_{cs}$-1 | |
| 2 | SECVEVFQNSCDW (SEQ ID NO: 2) | phage-2 | $K_{cs}$-2 | |

Scheme 1.

CuI-Catalyzed Azide-Alkyne Cycloaddition Reaction To Provide the Secondary Recognition Ligand, $K_{CS}$-2

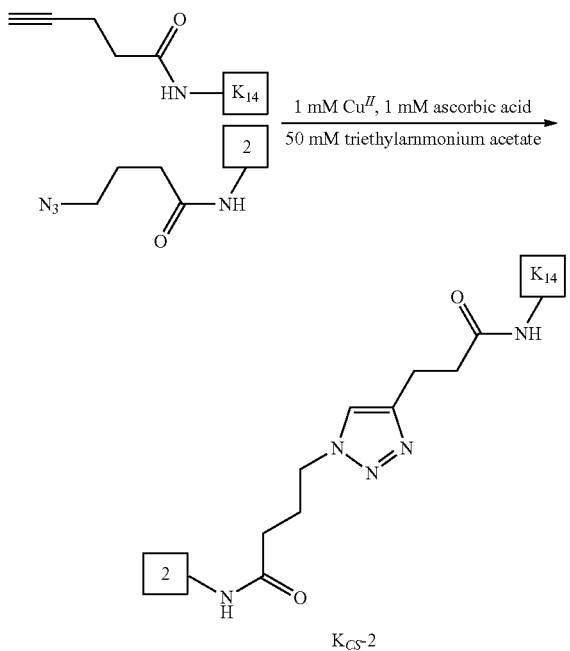

$K_{CS}$-2

3. Phage Wrapping to Maximize Ligand Density.

Figure 3A:
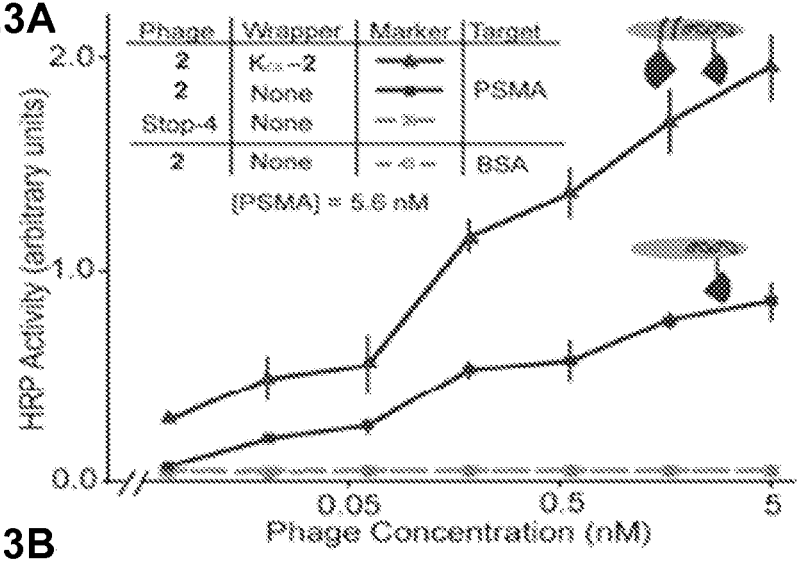
FIGS. 3A-3C. Phage-based ELISAs demonstrating the effectiveness of ligand wrapping.
Figure 3B:
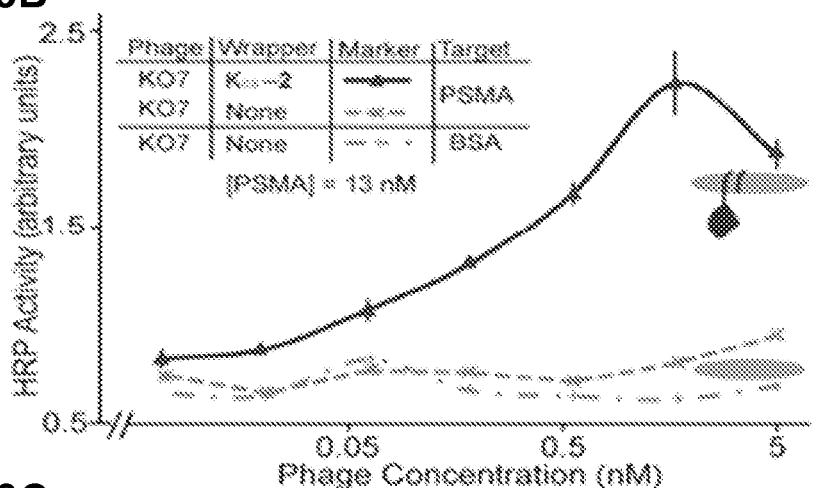
Figure 7:
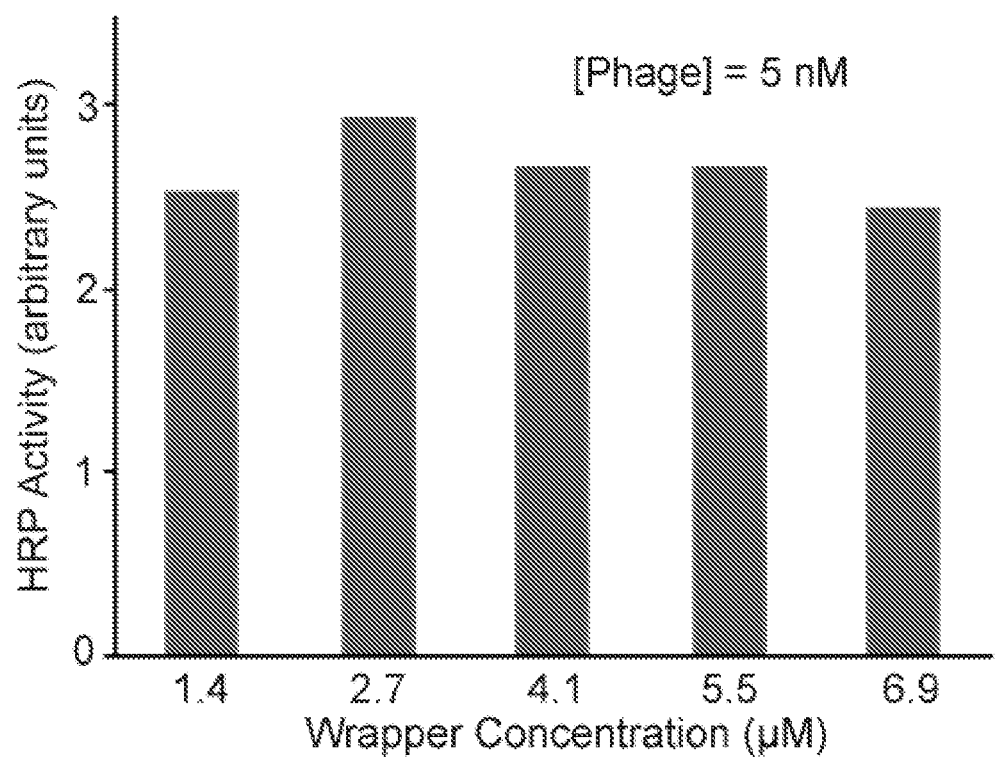
FIG. 7. Phage-based ELISA illustrating optimization of $K_{is}$-1 levels. A concentration of 2.7 µM for $K_{CS}$-1, offers an approximate 15% increase in apparent affinity to PSMA, versus other concentrations.
Figure 8:
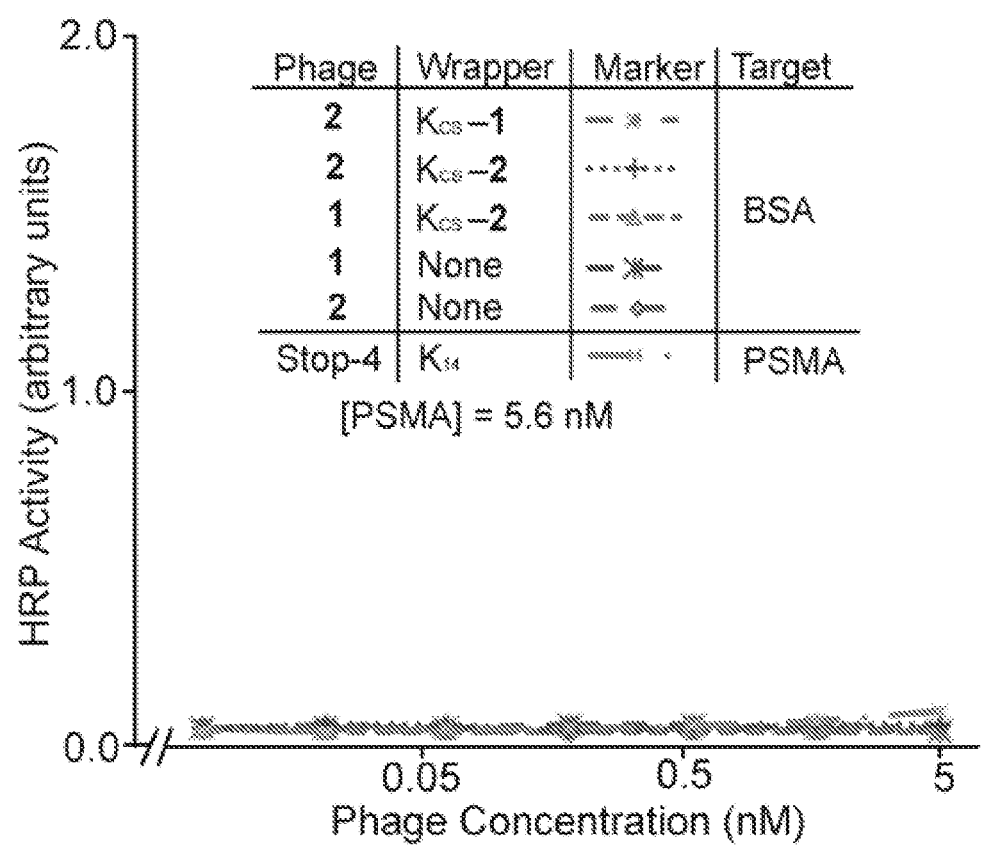
FIG. 8. Phage-based ELISA illustrating additional negative controls, the PSMA binding ligands targeting BSA and Stop-4 phage wrapped with $K_{14}$ targeting PSMA.

Wrapping the phage with chemically synthesized PSMA ligands described above clearly enhances binding affinity to PSMA (FIG. 3). The phage-displayed ligand (phage-2) was wrapped with the secondary recognition ligands ($K_{CS}$-1, $K_{CS}$-2, or a mixture of the two) to generate a phage surface displaying two PSMA ligands. The wrapped phage were then assayed for binding to the PSMA dimer. Negative controls, which resulted in no detectable binding, included the PSMA ligands targeting BSA and Stop-4 targeting PSMA. Phage-2 wrapped with $K_{CS}$-2 exhibits ~50 times higher affinity for PSMA than phage-2 without the ligand wrapper (FIG. 3A). Additional optimization examined the concentration of the wrapper (FIG. 7). As a result, the wrapper concentration can maximize the ligand density on the phage surface. The effectiveness of wrapping for improved binding affinity is dramatically demonstrated by comparing the binding affinities of the helper phage (KO7) versus KO7 wrapped with $K_{CS}$-2 (FIGS. 3B and 8). Lacking a displayed ligand, KO7 phage displays no significant binding to PSMA, but KO7 phage wrapped with $K_{CS}$-2 binds with significant affinity to PSMA. Taken together, the results demonstrate that the wrapping strategy achieves much higher affinity for the target, and the wrapped ligands remain functional.

4. Primary and Secondary Recognition Ligands on Phage for Bidentate Binding.

Figure 3C:
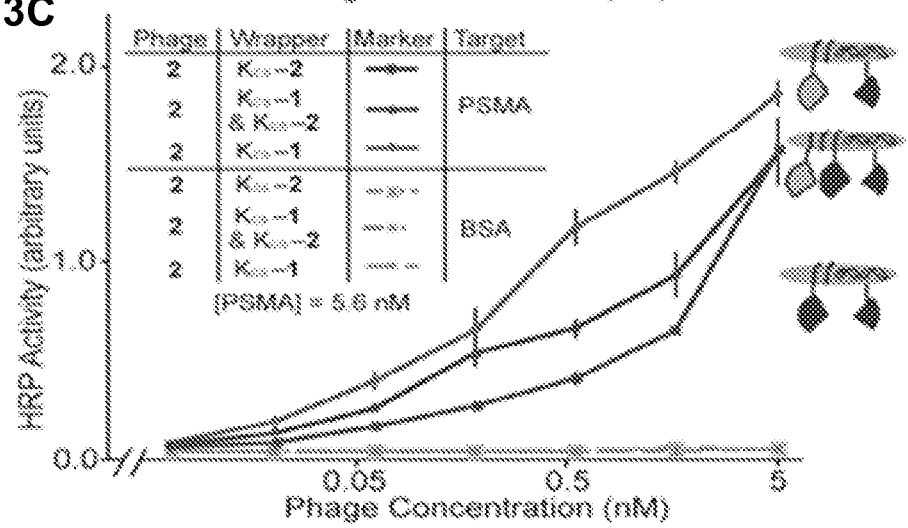

The arrangement and density of the primary, genetically encoded ligand and the secondary, chemically synthesized ligand determine the affinity of the wrapped phage for PSMA. For example, wrapping phage-2 with $K_{CS}$-1 results in phage with an apparent 4-fold higher affinity for PSMA than phage-2 wrapped with $K_{CS}$-2 (FIG. 3C). Peptide 1, however, has a much lower apparent affinity for PSMA than peptide 2, as shown in FIG. 1. Thus, the increased binding affinity of phage-2 wrapped with $K_{CS}$-1 suggests that the two ligands target different sites on the surface of PSMA. Furthermore, a 1:1 mixture of $K_{CS}$-1 and $K_{CS}$-2 wrapped on the surface of phage-2 offers intermediate affinity between neat $K_{CS}$-1 and neat $K_{CS}$-2. The results demonstrate that phage-2 wrapped with $K_{CS}$-1 results in improved affinity due to a bidentate binding interaction. Conversely, phage-2 wrapped with $K_{CS}$-2 fails to access this bidentate binding mode. Thus, the two ligands displayed on phage, for phage-2 wrapped with $K_{CS}$-1, can result in a chelate-based avidity effect, which enhances binding affinity beyond the gains achieved purely by maximization of ligand density.

In practice, chelate-based avidity effects can be challenging to design, as geometry and sterics must be satisfied to allow both ligands to reach an optimal interaction with the receptor. In fragment-based drug discovery efforts, for example, development of linkers with appropriate configuration is a non-trivial problem.[29] Phage wrapping provides a more-expedient solution to this problem. The second ligand, presented by a noncovalently bound wrapper, can equilibrate on the phage surface until finding a satisfactory geometry to allow simultaneous binding for synergistic effect.

Figure 4A:
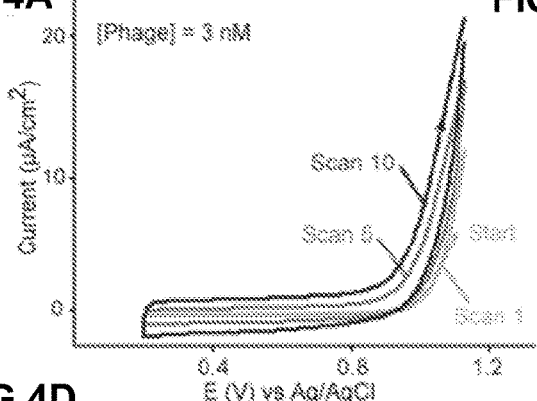
FIGS. 4A-4F. Biosensing with virus-PEDOT films.
Figure 4B:
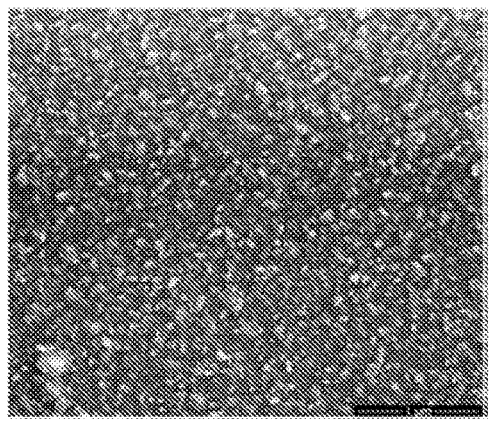

Biosensing with Virus-PEDOT Films. To explore whether these wrapped virus particles could be exploited to create virus-electrode biosensors with a higher sensitivity for PSMA, films of PEDOT were prepared on gold electrodes by electropolymerization in the presence of phage-2 (FIG. 2B). The PEDOT films formed in solution during electropolymerization associate with the negatively charged perchlorate ions from the electrolyte solution as it is deposited onto the gold electrode.[30] Polymerization of EDOT in the presence of negatively charged phage particles leads to incorporation of virus particles into the polymeric film as counterion dopants due to electrostatic interactions.[21] The cyclic voltammogram acquired during electrodeposition of the virus-PEDOT bioaffinity matrix indicates that the maximum current increases with every deposition cycle, consistent with the increase in the surface area of the film during growth (FIG. 4A). SEM imaging confirms incorporation of phage into the bioaffinity matrix; both filament-like and less extended features having dimensions consistent with phage integrated as rope-like bundles into the polymer at various angles to the film (FIGS. 4B-4C) were observed. The $K_{CS}$-1 wrapper was then applied in vitro simply by exposing the resultant phage-2 film for a short time to an aqueous solution of the wrapper. For the biosensing measurements, only the highest affinity ligand combination of phage-2 wrapped with $K_{CS}$-1 was used, and it was studied in comparison to phage-2 films.

Figure 4D:
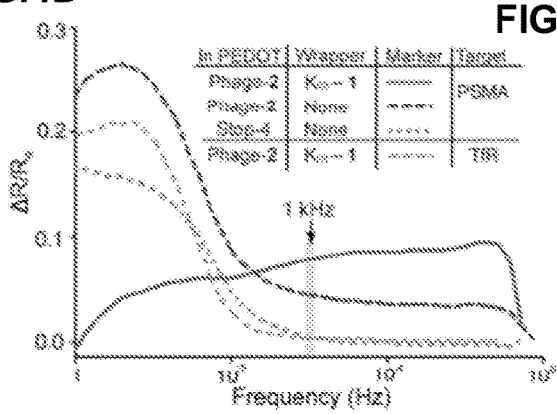
Figure 4C:
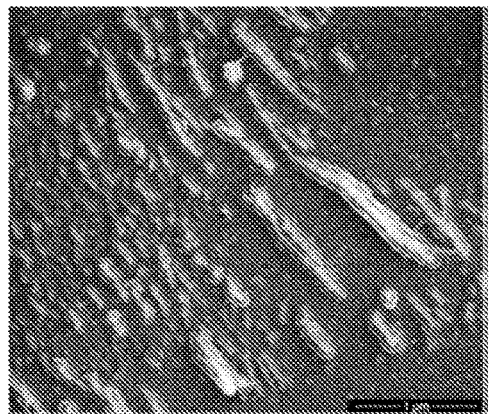
Figure 4E:
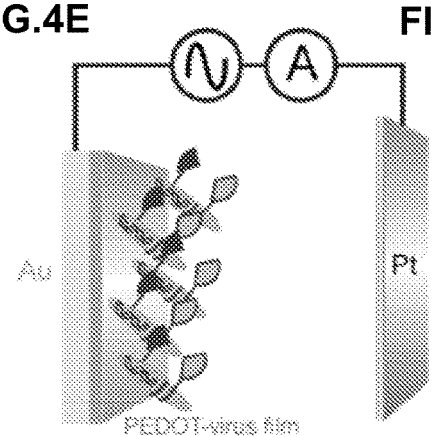
Figure 4F:
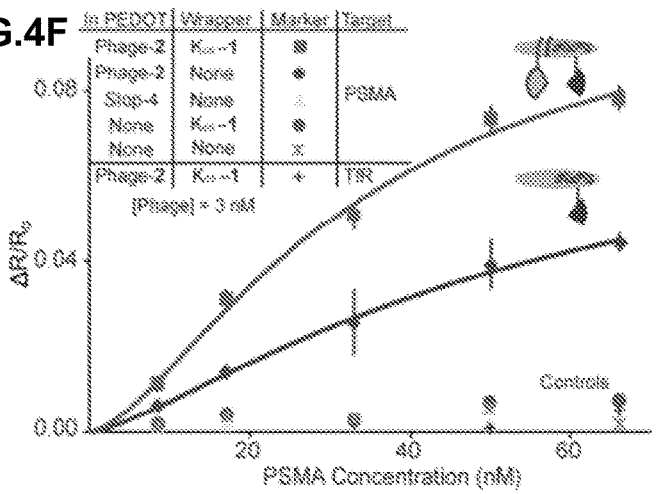

EIS To Quantify PSMA Binding. The electrochemical impedance of the virus-PEDOT film increases as PSMA selectively binds to the phage displayed peptide ligands (FIG. 4D). The real component of the impedance, R, in particular, increases upon PSMA binding. It has been demonstrated that the increase in R, ΔR, normalized by the initial resistance, $R_o$, ($\Delta R/R_o$), can be correlated with the concentration of a target molecule.[21] Here, impedance data were acquired in phosphate-buffered fluoride (PBF)-TWEEN buffer, spanning a frequency range from 0.1 Hz to 1 MHz in an electrochemical cell with a Pt counter electrode and virus-PEDOT film electroplated on a planar gold working electrode (FIG. 4E). The films incorporating phage-2 wrapped with $K_{CS}$-1 provide higher sensitivity for PSMA detection than films incorporating unwrapped phage-2 (FIG. 4F). For example, the relative impedance change, $\Delta R/R_o$, at each concentration of PSMA is 3-fold higher. The noise present in this measurement (estimated as the standard deviation for five impedance measurements) is unchanged, resulting in a much higher signal-to-noise ratio for phage-2 wrapped with $K_{CS}$-1 relative to unwrapped phage-2. A series of negative controls validate the data obtained. The PEDOT films incorporating Stop-4 phage, PEDOT films lacking PSMA binding ligands, and PEDOT films incubated with $K_{CS}$-1 result in no significant binding to PSMA. The specificity of PSMA binding was investigated by using an alternative target, transferrin receptor (TfR), which has 54% sequence similarity to PSMA. No significant binding affinity to TfR was observed. This experiment illustrates the negligible change in impedance caused by the wrapper due to its small size.

Calculating the Hill Coefficient. The biosensing data acquired for phage-2 and phage-2 wrapped with $K_{CS}$-1 targeting PSMA follow a Langmurian adsorption model. The acquired data were fit to the following Hill equation:

$$Y = \frac{Y_{max} * [L]^n}{[K_d]^n * [L]^n}$$

where $Y=\Delta R/R_o$, [L] is the ligand concentration, and n is the Hill coefficient.[31] Consequently, the dissociation constant, $K_d$, and n were determined for phage-2 ($K_d$=54 nM, n=1.3, LOD=6 nM) and phage-2 wrapped with $K_{CS}$-1 ($K_d$=33 nM, n=1.5, LOD=3.1 nM). Here, the two LODs, defined as 3× over background signal, were calculated from line fits to the data shown in FIG. 4F. The response obtained for phage-2 wrapped with $K_{CS}$-1 displays a much higher signal-to-noise ratio compared to that obtained for films incorporating only phage-2. Such sensitivity can play a crucial role in low-concentration analyte detection. The n-values obtained are >1, indicating the presence of multiple binding sites and a cooperative binding effect. Phage-2 can access cooperative binding due to the avidity effect of multicopy phage-displayed ligands. Wrapping phage with additional ligands leads to a further increase in cooperativity for phage-2 wrapped with $K_{CS}$-1. Again, the synergism of the two ligands leads to higher PSMA binding affinity for phage-2 wrapped with $K_{CS}$-1.

Figure 5A:
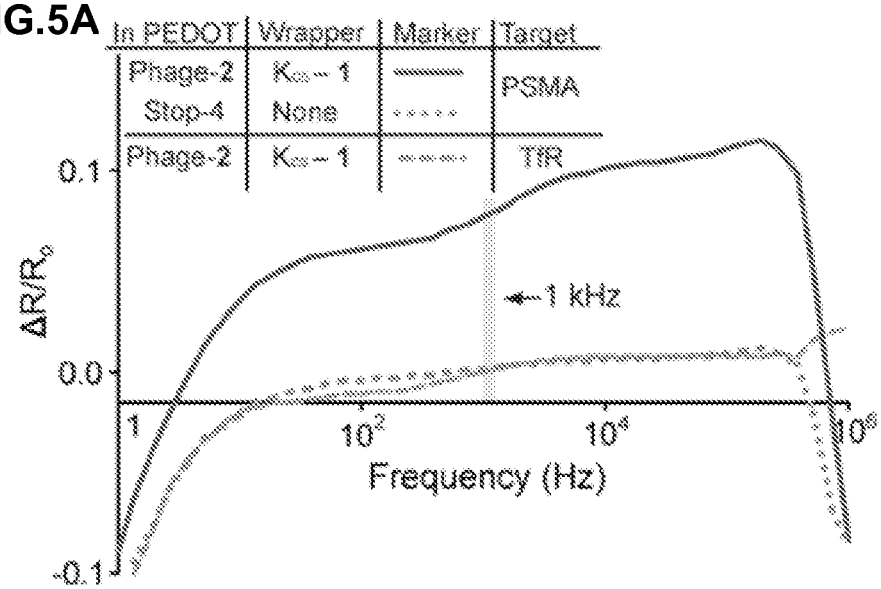
FIGS. 5A-5B. Detection of PSMA in synthetic urine using virus-PEDOT film biosensors.
Figure 5B:
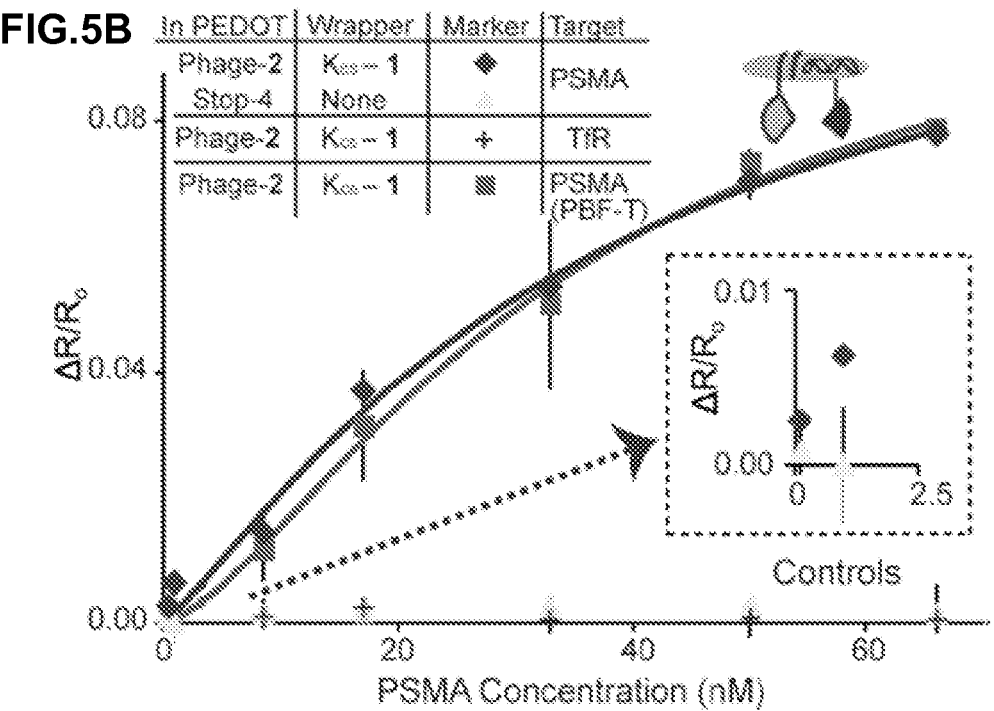
Figure 6:
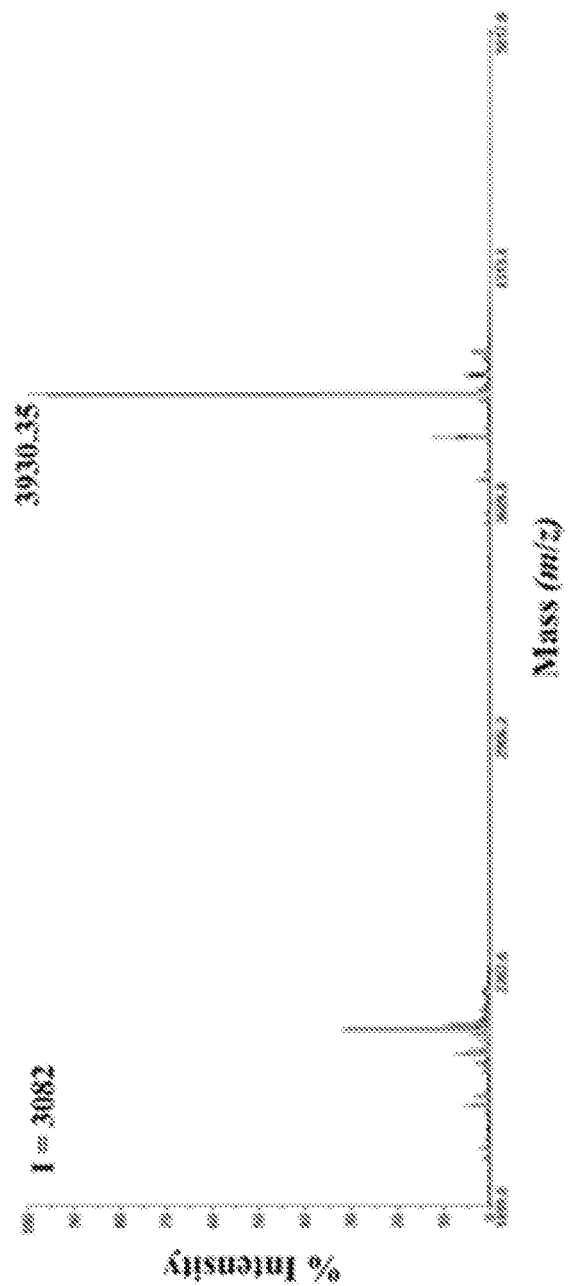
FIG. 6. A representative MALDI-TOF of the purified product from the azide-alkyne cycloaddition reaction. The azide-functionalized peptide-2 and alkyne-functionalized oligolysine yields $K_{CS}$-2. The calculated m/z for $K_{CS}$-2 [M$^+$] 3930.31, found 3930.35.

PSMA Detection in Synthetic Urine. To further demonstrate the usefulness of the approach for potential clinical applications, biosensing data were next acquired in synthetic urine. This complex solution includes water, nitric acid, urea, sodium sulfate, potassium chloride, sodium dihydrogen phosphate, sodium chloride, ammonium chloride, and 10 other components; the resultant solution has a high salt concentration (a calculated osmolality of 516.2 mOsm/kg and a pH of 5.8).[32,33] The solution provides a good model for the clinical challenge of identifying cancer biomarkers found in urine samples. Substituting synthetic urine for PBF, impedance measurements with virus-PEDOT films were acquired as before (FIG. 5A). Having already established phage-2 wrapped with $K_{CS}$-1 as the most effective ligand combination for detecting PSMA in terms of sensitivity, specificity, and signal-to-noise ratio, experiments focused on this ligand combination for synthetic urine-based biosensing. In the presence of PSMA, the impedance scans for virus-PEDOT films of phage-2 wrapped with $K_{CS}$-1 follow similar trends in both PBF and synthetic urine. However, the lower frequency ranges differ dramatically for the negative controls. For example, the negative control with Stop-4 phage in PBF displayed a much higher $\Delta R/R_o$; this response at low frequencies was suppressed in synthetic urine. Thus, the measurements in synthetic urine resulted in higher specificity for the PSMA-ligand interaction. Turning next to the measurement of PSMA concentration, the synthetic urine solution also appeared to enhance measurement sensitivity. The calibration curves in PBF and synthetic urine were overlaid for comparison (FIG. 5B, plot with squares and plot with diamonds, respectively). At high analyte concentrations, measurements in PBF and synthetic urine are superimposable. Both conditions reach saturation at high PSMA concentrations, hence the overlap in device response. At the lowest PSMA concentrations, the higher $\Delta R/R_o$ response in synthetic urine can be attributed to higher sensitivity and selectivity for PSMA under the high-salt conditions. Phage-2 film wrapped with $K_{CS}$-1 targeting PSMA in synthetic urine yields a 100 pM experimentally observed LOD. Applying the calculation to determine LOD described above yields a 10 pM LOD for the detection of PSMA in synthetic urine. Furthermore, this sensitivity requires no signal or enzymatic amplification. As before, no significant change in impedance was observed for the negative controls. The high salt concentration in synthetic urine appears to prevent nonspecific charge-charge interactions. Binding of the biomarker to the virus-PEDOT film generates a positive $\Delta R/R_o$, whereas a negligible $\Delta R/R_o$ for the negative controls indicates a nonsignificant extent of nonspecific binding by the analyte. The resultant specificity increase in synthetic urine boosts the apparent sensitivity of the device by decreasing background binding. This effect also enhances the sensitivity by unmasking a higher concentration of ligands for analyte detection, which would otherwise be occluded through nonspecific binding. Thus, a dramatic improvement in specificity and sensitivity can be obtained through the decreased nonspecific interactions. The results suggest a general strategy for improving biosensor performance through focusing on decreased nonspecific binding.

The 100 pM experimentally measured LOD obtained for phage-2 wrapped with $K_{CS}$-1 is a significant improvement over our previous effort, which had a >66 nM LOD[22] for PSMA. This detection sensitivity satisfies a key requirement for clinical applications. The chelate-based avidity effect and high specificity obtained due to the bidentate binding mode distinguish this work from previous efforts and also account for the greatly improved signal-to-noise ratio and LOD obtained without enzymatic amplification. Furthermore, inclusion of synthetic urine as an analyte solution expands the applicability of the technique. In conclusion, wrapping phage with additional ligands can increase the target affinity due to a chelate-based synergistic effect. Phage-2 wrapped with $K_{CS}$-1 binds to PSMA with $K_d$=33 nM and LOD=3.1 nM in PBF, and a 100 pM experimentally measured LOD in synthetic urine.

5. PEG Wrappers to Prevent Non-Specific Binding to Cells

In a cell-based ELISA, specific wells of a 96-well microtiter plate (Nunc Maxisorp) were coated with 100 µL/well of a solution of LNCaP cells ($4.5 \times 10^6$ cells/mL) in phosphate buffer (PBS). The plate was centrifuged for 10 min at 1200 rpm at 4° C. Next, 50 µL/well of a solution of glutaraldehyde was added to a final concentration of 0.05%. The microtiter plate was next incubated overnight at 4° C. The plate was centrifuged for 10 min at 1200 rpm at 4° C. The coating solution was removed, and the wells were blocked overnight at room temperature with 200 µL/well of the blocking solution (1.12 g glycine, 1 g gelatin in a 100 mL 0.1% w/v solution of bovine serum albumin in PBS). The wells were washed two times with 300 µL/well of PBS. Separately, 10 nM Stop-4 phage, phage with helper phage packaging the phagemid DNA, is wrapped with oligolysine-alkyne for 15 mins, as described above. Next, click reaction was performed for 30 mins with azide functionalized PEG 7, or PEG 1000 ($M_n$) or PEG 2000 ($M_n$). The wells on the ELISA plate were then incubated with the phage samples for 35 min. The wells were washed three times with wash buffer PT, and once with PBS, and then incubated with horseradish-peroxidase-conjugated anti-M13 antibody (100 µL/well, 1:5000 dilution in PBS) for 35 min. The wells were washed three times with PT, and once with PBS. The plate was then developed by incubating with HRP substrate solution (100 µL/well; 1 mg/mL o-phenylenediamine dihydrochloride and 0.02% w/v $H_2O_2$) in citric acid buffer (50 mM citric acid, 50 mM $Na_2HPO_4$, pH 5.0). Following an appropriate incubation time, HRP activity was measured spectrophotometrically at 450 nm using a microtiter plate reader (Bio-Tek).

6. PEI Wrappers for Increasing the Concentration of Phage Incorporated into Virus-PEDOT Films Virus particles are incorporated into a highly conductive, organic polymeric film PEDOT via electropolymerization from a solution of EDOT and phage, on the surface of a gold electrode. Cyclic voltametry is used for the synthesis of the virus-PEDOT film. A planar gold electrode serves as the working electrode, a platinum electrode is used for the counter electrode, and a saturated calomel electrode (SCE) is used as the reference electrode. The electrodes are placed in a solution containing 12.5 mM $LiClO_4$, 2.5 mM EDOT, and 3 nM phage, and potential is varied between 0.4 and 1.1 V vs. SCE for 9.5 cycles at a scan rate of 20 mV/s. Next, the films are incubated with 50 µM PEI for one hour, followed by exposure to 32 nM Stop-4 phage for 30 min. The surface of the phage is covered in many negative charges from the P8 coat protein. PEI contains many positive charges, which causes the PEI to stick to the phage. Upon addition of more phage to the surface of this film, the additional phage sticks to the PEI, resulting in a higher density phage film. The electrochemical impedance of the film is measured before and after exposure to E. coli by applying a small amplitude perturbation (10 mV vs. 0 V open circuit potential) over a wide range of frequencies (from 10 Hz to 100 kHz). The device response is calculated as the change in the impedance after binding of E. coli to the surface of the film.

7. Non-Specific Adhesion of Viruses to Cells

Figure 14:
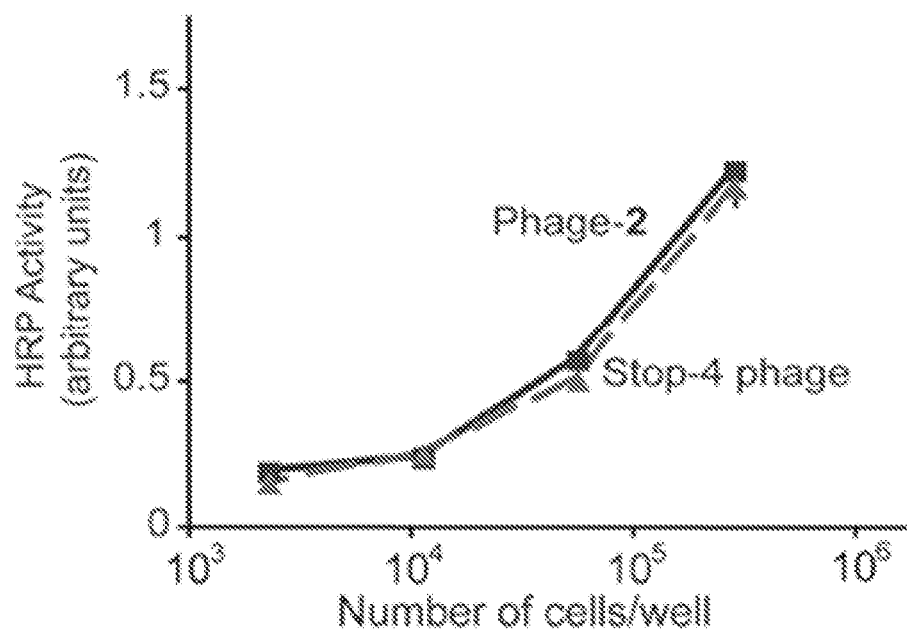
FIG. 14. Phage-based ELISA demonstrating high non-specific adhesion of phage to the surface of LNCaP cells. Phage-2 display the PSMA ligand 2. Stop-4 phage provides a negative control with no ligand displayed on the phage. Throughout this report, error bars for ELISA data represent standard error (n=3). All experimental data points include such error bars, though often these are quite small.

Among prostate cancer cell lines, LNCaP cells provide the most commonly used in vitro model for early stage PCas.[23,24] Derived from the lymph node adenocarcinoma of the human prostate, LNCaP expresses most of the important PCa biomarkers including PSMA, PSA and AR.[25] Attempts to recognize cell surfaces with conventional phage-displayed ligands resulted in unacceptably high non-specific adhesion by control phage. As shown by ELISA, phage-displayed, PSMA ligand 2 and control phage lacking a displayed peptide produced similar, high levels of binding to LNCaP cells (FIG. 14). Control phage package the phagemid genome in the wild-type phage capsid, but do not have an ORF encoding a ligand for display. Thus, the high levels of adhesion by both ligand-displayed and control phage were due to non-specific adhesion between phage coat proteins and abundant cell surface receptors, glycans and other molecules. To overcome this non-specific adhesion, we focused on eliminating such binding by control phage.

8. Wrapping Phage with PEG to Prevent Non-Specific Adhesion

The water soluble polymer PEG is commonly bioconjugated to proteins to reduce non-specific adhesion to cells and other surfaces.' In addition, PEG can increase the solubility of attached therapeutic proteins, prolong circulation times, decrease proteolysis, and other effects.[30] Furthermore, the activity of proteins conjugated to PEG typically remains unperturbed.[31,32] PEG broadly adopts two distinct conformations—mushroom and brush.[26,33] The transition from mushroom, a more random orientation, to the brush configuration is dependent upon the polymer length and packing densities. This transition can result in a significant drop in non-specific adsorption. In many systems, a mole fraction of 0.15 PEG-modified to -unmodified sites yields significantly reduced non-specific adhesion.[26] High packing density can force the polymer to adopt a more stretched, and extended brush configuration to more effectively suppress non-specific adhesion.

Figure 15:
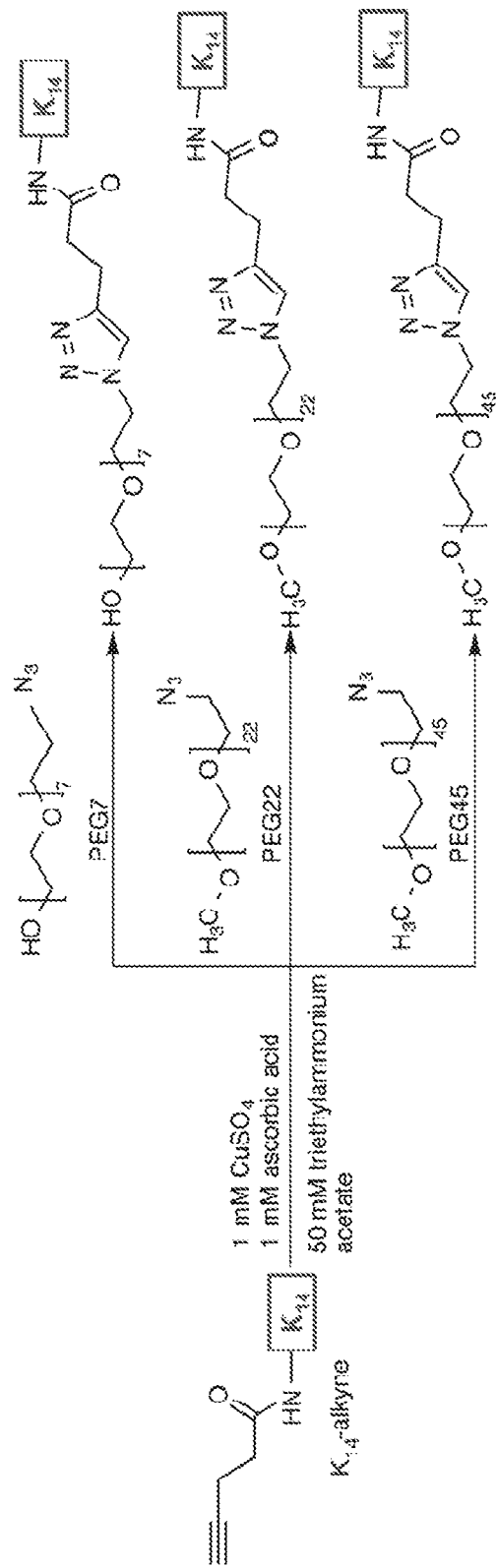
FIG. 15. depicts Cu$^I$-catalyzed azide-alkyne cycloaddition reaction for the generation of oligolysine-PEG wrappers.
Figure 16:
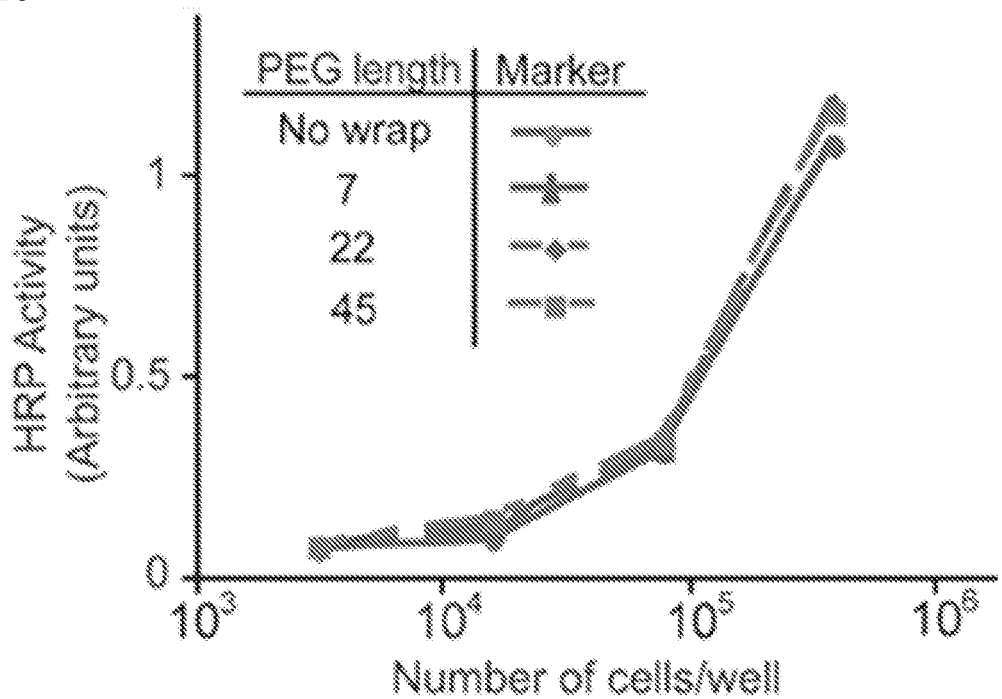
FIG. 16. Phage-based ELISA demonstrating the ineffectiveness of wrapping phage with PEG polymers due to the encapsulation of oligolysine side chains. Phage without wrapper and phage wrapped with PEG7, 22 or 45 at 5 µM concentrations were compared.

Initial attempts to block non-specific cell adhesion applied PEG variants with different MWs as phage wrappers. Azide-functionalized, polydisperse PEGS with average MWs of 300, 1K or 2K (a distribution of polymers centered around 7, 22 or 45 ethylene glycol units, respectively) were conjugated to $K_{14}$-alkyne using the $Cu^I$-catalyzed cycloaddition ('click') reaction, FIG. 15. The conjugated peptides were then purified by reverse-phase HPLC and characterized by MALDI-TOF mass spectrometry. The relative binding affinities of unwrapped and PEG-wrapped phage targeting immobilized LNCaP cells were compared by phage-based ELISA, FIG. 16. Phage lacking a displayed ligand were used; thus, non-specific adhesion could only result from binding by the phage coat proteins and not from a displayed ligand with poor specificity.

In theory, phage wrapped with PEG should bind to LNCaP cells with much lower affinity due to decreased non-specific adhesion. However, no such reduction was observed for the different MW PEGs used, FIG. 16. The ineffectiveness of this initial approach likely resulted from interaction between the PEG and the oligolysine sidechains used to wrap the phage. A crown ether-like encapsulation can form between the primary amine of the Lys side chains and ethylene glycols of PEG,[34] thereby rendering $K_{14}$ incapable of wrapping the phage surface.

9. On-Phage Cycloaddition Reaction to Generate PEGylated Phage

Figure 21:
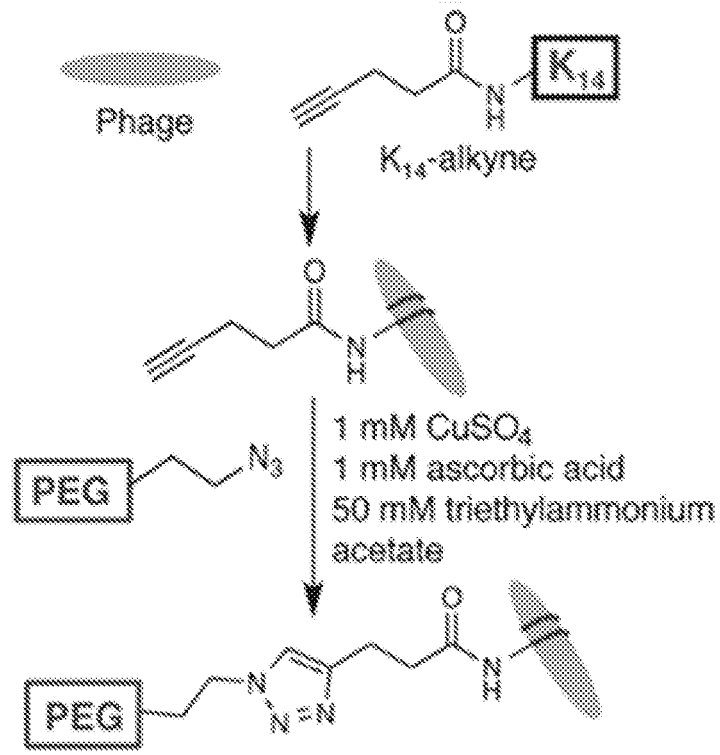
FIG. 21. Schematic illustration of the on-phage cycloaddition reaction to bioconjugate PEG polymers to the phage surface. Phage are first wrapped with $K_{14}$-alkyne, and then conjugated to different lengths of azide-functionalized PEG polymers.
Figure 22:
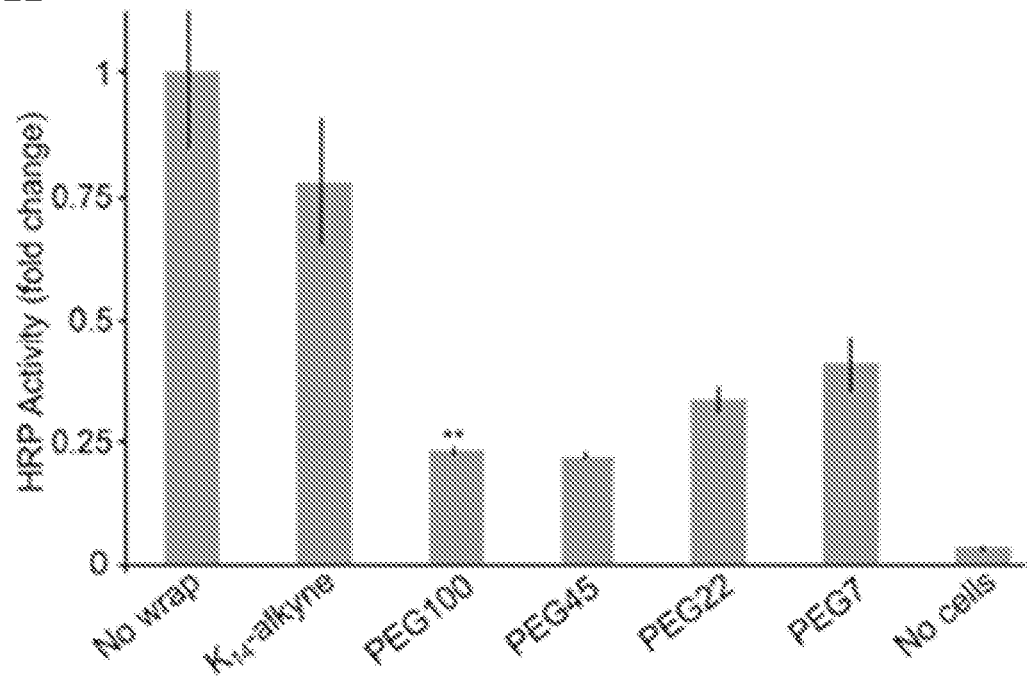
FIG. 22. shows a histogram depicting phage-based ELISA demonstrating the effectiveness of wrapping phage with PEG polymers to reduce non-specific adhesion to cellular surfaces. A >75% reduction in non-specific adhesion to LNCaP cells is observed for PEG45 compared to unwrapped phage. Throughout this report, LNCaP cells are targeted at $4.5 \times 10^6$ cells/mL, and error bars for ELISA data represent standard error (n=3). All experimental data points include such error bars, though often these are quite small. (**p<0.01 for all data sets included in this report).

To overcome $K_{14}$ encapsulation by PEG, phage with PEG wrappers were generated in two steps, as depict in FIG. 21. First, phage were wrapped with $K_{14}$-alkyne for 15 min. Thus, the oligolysine can wrap the phage prior to PEG conjugation. Next, PEG azide was added, and the cycloaddition reaction with the $K_{14}$-alkyne took place on the phage surface for 30 min. The non-specific adhesion of phage wrapped with different MW PEGS was then compared by ELISA, FIG. 22. Phage wrapped with PEG45 and PEG100 (average MW 2K and 5K, respectively) demonstrate a >75% reduction in non-specific binding to LNCaP cells. The reduction in non-specificity increases with larger MW PEG, and saturates at around 45 ethylene glycol units.

PEG reduces non-specific binding largely by surrounding the attached surface with a hydration sphere.[35] Direct contact to the phage surface, termed primary adsorption, requires smaller non-specific binding partners to penetrate the PEG layer. Alternatively, the non-specific binding partners could adhere to the outer surface of the PEG layer, termed secondary adsorption. For the larger surfaces of cells, such secondary adsorption is likely a more pronounced effect. To minimize secondary adsorption, the wrappers were applied at a 0.15 mole fraction.[26] Here, we estimate the mole fraction as the stoichiometry of PEG molecules added to P8 coat proteins; this analysis is analogous to the calculations for PEG grafted in lipid membranes.[36] Additionally, at the concentration used, PEG22, 45 and 100 adopt brush conformations due to their high packing densities[26,33], which was fixed by maximization of oligolysine wrappers as previously described.[4]

PEG7 largely adopts a mushroom conformation, and fails to suppress non-specific adhesion to the same levels. The brush conformation of the larger PEGs can more efficiently reduce non-specific secondary adsorption due to the hydration sphere extending further from the virus surface. Beyond a certain height of the polymer brush, the effect of secondary adsorption remains constant as shown by the nominal difference obtained between PEG45 and 100. Hereafter, phage wrapped with PEG45 was used as the negative control phage, lacking a displayed ligand, for further experiments aimed at specific recognition of PSMA on the surface of LNCaP cells.

10. Synthesis of PEGylated Ligands

Figure 29:
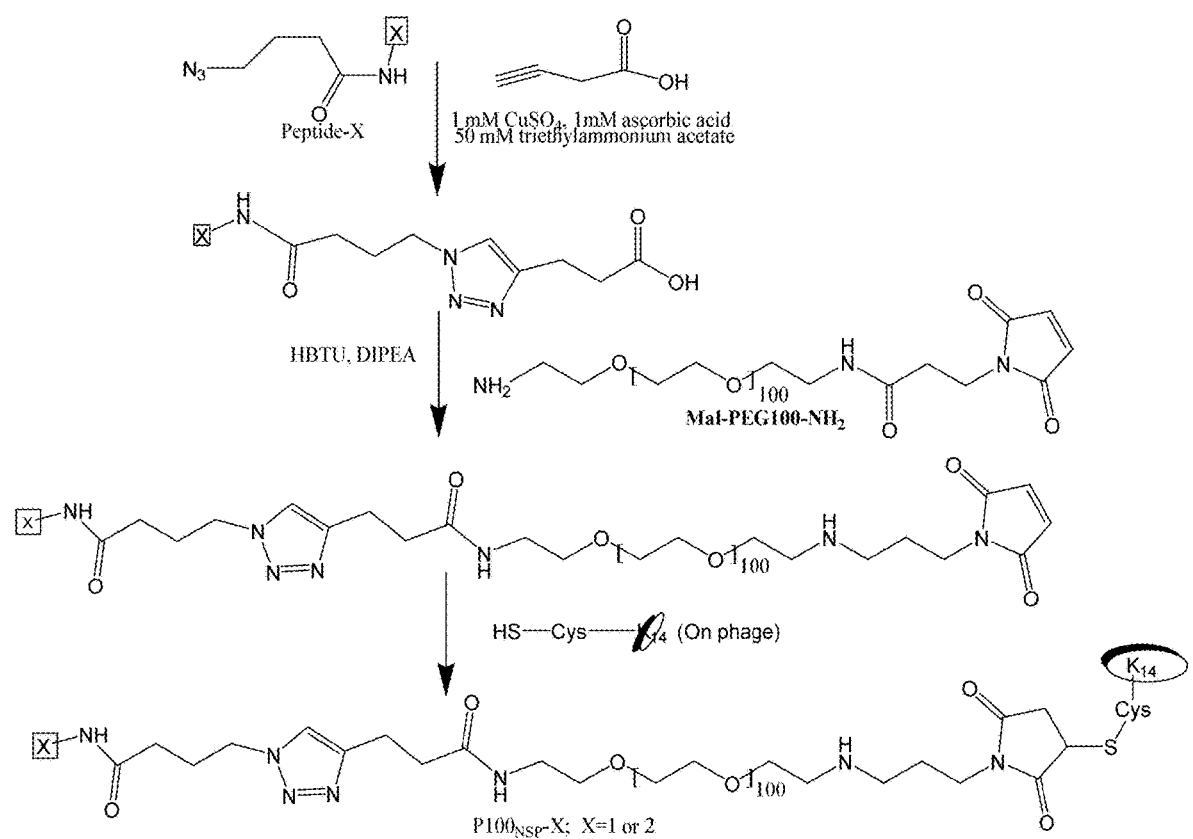
FIG. 29. shows scheme 3, synthesis scheme for the generation of PEGylated ligands on phage for the selective detection of PSMA on LNCaP cells.

Towards the goal of specific recognition of a cell surface receptor, different scaffolds for the display of ligands on phage were explored. First, heterobifunctional PEG, Mal-PEG-NH$_2$, provided reactive groups for selective attachment of oligolysine at the maleimide end and PSMA binding ligands to the amine end (FIG. 29). As the scaffold, PEG100 was chosen to provide a longer polymer brush to reduce non-specific secondary adsorption. PSMA ligands 1 and 2 were synthesized by conventional solid-phase peptide synthesis (SPPS), and coupled to pentynoic acid via click reaction. The resultant N-terminal carboxylic acid group was then coupled to Mal-PEG100-NH$_2$ using HBTU as an amide bond forming agent in water. Since this reaction non-specifically couples amine and carboxylate functionalities, the attachment sites could vary as both ligands have side chain carboxylic acids. The resultant ligand is termed P100$_{NSP}$-1/2 for 'PEG100, non-specific attachment to ligand 1 or 2,' Table 2.

TABLE 2

Nomenclature of PEGylated PSMA ligands. All ligands were bioconjugated to phage wrapped with K$_{14}$-Cys.

| PEG length | Attachment SP: specfic NSP: Non-specific | PEG4 linker | Nomenclature |
|---|---|---|---|
| P100 | NSP | — | P100$_{NSP}$-X |
| P100 | SP | — | P100$_{SP}$-X |
| P100 | NSP | ✓ | P100$_{NSP}$-P4-X |
| P100 | SP | ✓ | P100$_{SP}$-P4-X |

X = ligand 1 (CALCEFLG) (SEQ ID NO: 1) or 2 (SECVEVFONSCOW) (SEQ ID NO: 2)

Figure 17:
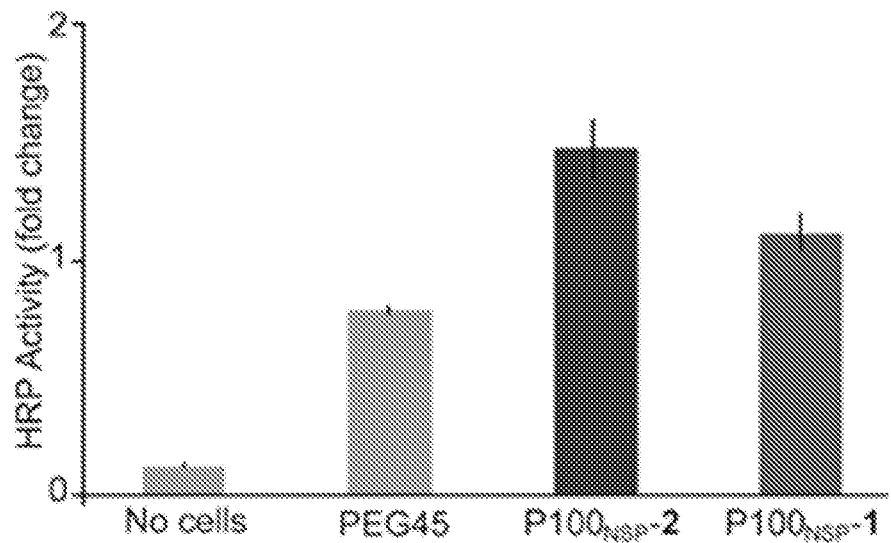
FIG. 17. Phage-based ELISA illustrates a modest increase in binding affinity using PEGylated ligands on phage targeting LNCaP cells. PEGylated ligands on phage were further engineered for higher affinity of recognition.

Subsequently, phage wrapped with K$_{14}$-Cys were coupled to the maleimide terminus of P100$_{NSP}$-1/2. Preliminary validation of binding to cell surface PSMA by the PEGylated ligand wrappers was performed by phage ELISA as before, FIG. 17. Compared to the non-specific binding observed in FIG. 14, a slight improvement in binding affinity resulted from wrapping with the PEGylated ligands. This modest result provided a starting point for further engineering. Phage wrapped with P100$_{NSP}$-2 displayed a higher affinity for LNCaP cells compared to P100$_{NSP}$-1.

11. Bidentate Binding Mode of PEGylated Ligands

Dual display of ligands 1 and 2 enables synergistic binding to PSMA due to a bidentate binding mode and a "VELCRO®-like" (i.e., hook and loop) avidity effect.[4] Unlike the previous study with one genetically encoded and one chemically synthesized ligand, the two synthetic ligands used here can allow more rapid optimization of the bidentate binding mode. A phage ELISA targeting LNCaP cells with different ratios of the two PEGylated, phage-wrapped ligands examined their relative binding affinities. First, the effectiveness of the bidentate binding mode was compared to binding by individual ligands, FIG. 23. Having two ligands on the phage surface consistently improved binding affinity. Next, a 2:1 mixture of P100$_{NSP}$-2 and P100$_{NSP}$-1 respectively, was found to maximize the recognition of PSMA on LNCaP cells. The 2:1 ratio stems from the higher binding affinity of ligand-2 compared to ligand-1. Altering this ratio in either direction drops the apparent affinity, likely due to loss of bidentate binding. Hereafter, phage were wrapped with a 2:1 mixture of the PEGylated ligands 2 and 1, respectively.

12. Optimizing the Attachment Site for PEGylated Ligands

Figure 18:
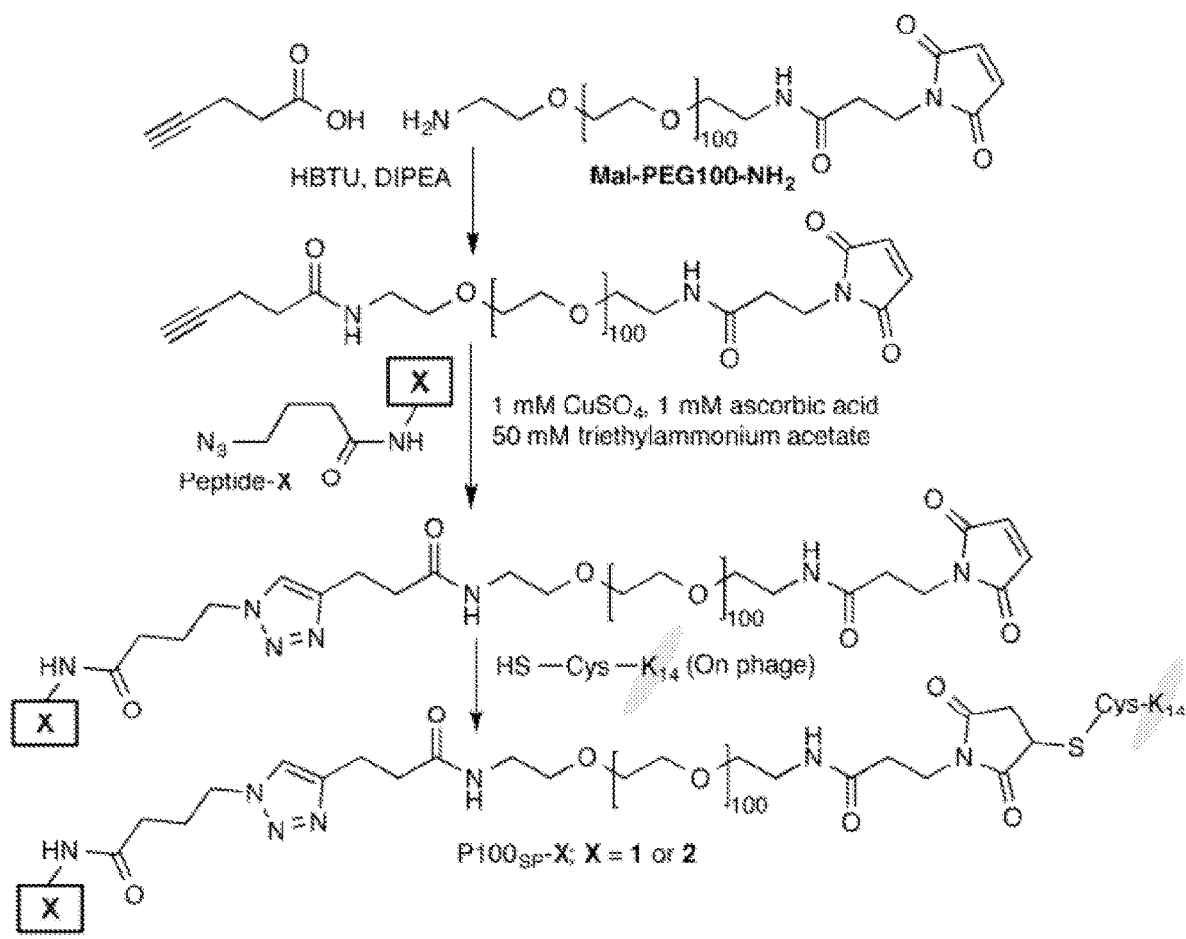
FIG. 18. Synthesis scheme for the generation of PEGylated ligands on phage through the specific attachment mode.

Further optimization explored the size, geometry and attachment site of PEG. Such variables can be crucial to the pharmacokinetic properties of PEGylated drugs, which demonstrates the sensitivity of biological recognition to such factors.[37] For example, the attachment sites of the peptide ligand to PEG100 dictates the ligand orientation and the potential availability of peptide side chains. An alternative synthesis scheme was designed to control ligand orientation. Mal-PEG100-NH$_2$ was first coupled to pentynoic acid, FIG. 18. The resultant Mal-PEG100-alkyne was then coupled to the azide-functionalized peptide ligands using click chemistry, providing a specific site of attachment. The resulting PEGylated ligand is termed P100$_{SP}$-1/2 for 'PEG100, specific attachment to ligand 1 or 2,' Table 2.

Figure 19:
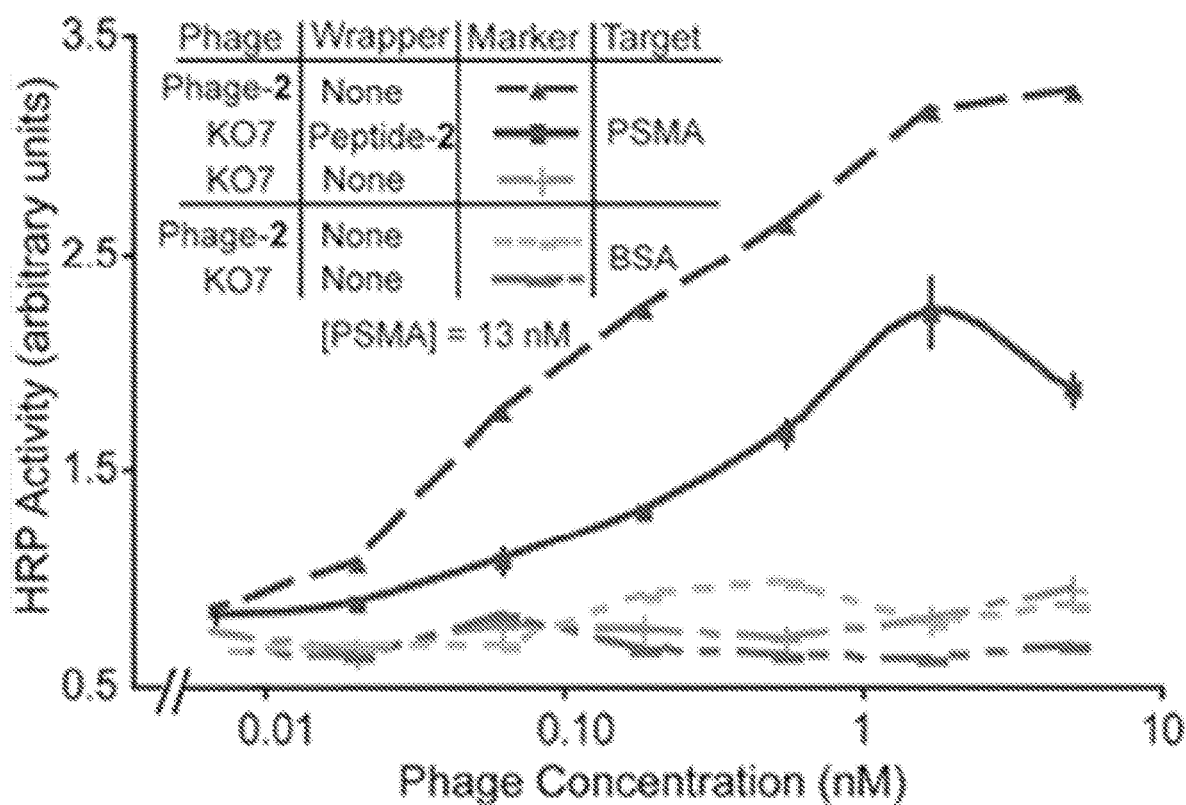
FIG. 19. Phage-based ELISA demonstrating the significance of the free N-terminus of peptide-2 for PSMA binding as shown by the higher affinity of phage-displayed peptide-2. Synthesis and wrapping of oligolysine-peptide-2 leads to the inversion of geometry providing a free C-terminus. The solid line and two of the controls are being reprinted with permission from Mohan, K., Donavan, K. C., Arter, J. A., Penner, R. M., and Weiss, G. A. 2013. Sub-nanomolar Detection of Prostate-Specific Membrane Antigen in Synthetic Urine by Synergistic, Dual-Ligand Phage. J. Am. Chem. Soc. 135:7761-7767. Copyright (2013) American Chemical Society.
Figure 20:
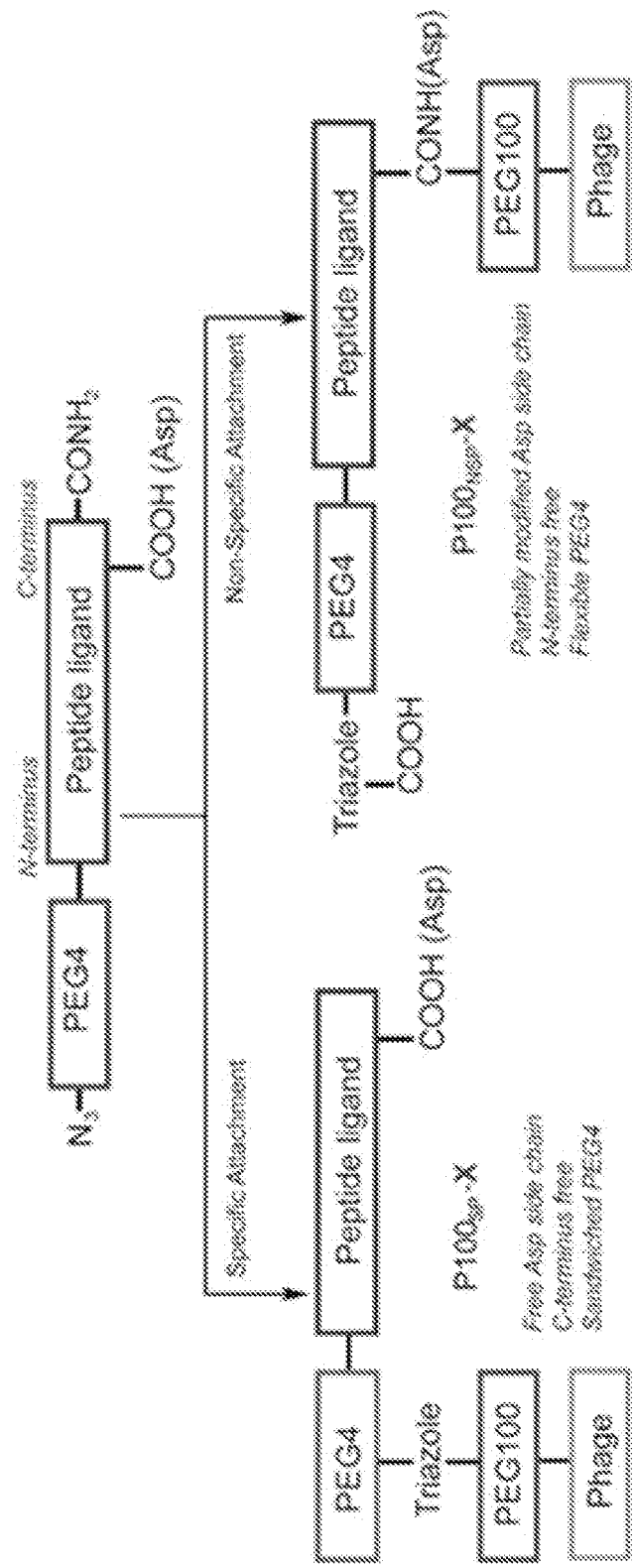
FIG. 20. Schematic representation of the two constitutional isomers of P100-P4-X. The differences between the products obtained through the specific attachment mode and the non-specific attachment mode are illustrated and enlisted. The partial product formed through the Asp side chain in the non-specific attachment mode, which significantly affects the binding affinity of ligands is illustrated here. The insertion and role of the PEG4 linker is also explained.

Specific attachment of PEG to the wrapped ligands could improve binding affinity by removing attachment through the ligands' side chains and also altering their orientation on the phage surface. The significance of ligand orientation is apparent through the higher binding affinity observed for genetically encoded, phage-displayed ligand 2 relative to phage wrapped with chemically synthesized ligand 2, FIG. 19. When displayed on the phage as a fusion to P8, ligand 2 has a free N-terminus, but the synthesis of P100$_{SP}$-2 inverts this orientation, leaving a free C-terminus, and an N-terminus conjugated to PEG100, FIG. 20. The C-terminal Asp residue of ligand 2 requires an unmodified carboxylate side chain, as shown by homolog shotgun scanning.[10] The side chain of Asp12 could be partially modified in P100$_{NSP}$-2 due to non-specific attachment through the Asp side chain. Subsequent experiments compared bioconjugation to either the N-terminal amine or C-terminal Asp side chain through incorporation of an additional linker.

13. Insertion of a PEG4 Linker to Reduce Steric Effects on Ligands

Heterobifunctional linkers between PEG and a molecule of interest can enhance activity through flexible additional spacing.[35] We envisioned the incorporation of an average 175 MW PEG4 linker between the peptide ligand and the triazole generated by click reaction could enhance the binding affinity of the peptide ligands. With only four ethylene glycol units, this highly flexible linker can disconnect the peptide ligand from any steric constraints dictated by PEG100 or the triazole, FIG. 20. Thus, the peptide ligands were resynthesized via SPPS, and coupled to azido-PEG4-carboxylic acid (15-Azido-4,7,10,13-tetraoxapentadecanoic acid), thereby inserting a PEG4 linker before the azide functionality. Azido-PEG4-ligands were further linked to PEG100 following the two synthesis routes described above, specific and non-specific addition. The resultant PEGylated ligands are termed P100$_{SP}$-P4-1/2 and P100$_{NSP}$-P4-1/2, P4 to indicate the insertion of the PEG4 linker, Table 1.

An ELISA compared the relative binding affinities of the four PEGylated ligand-2 variants—specific and non-specific attachment with and without the PEG4 linker, FIG. 24A. $P100_{SP}$-2 demonstrates a higher binding affinity for cell surface PSMA than $P100_{NSP}$-2, illustrating the significance of the unmodified C-terminal Asp side chain obtained through specific attachment. Furthermore, inclusion of the PEG4 linker further enhances the binding affinity for both $P100_{SP}$-2 and $P100_{NSP}$-2. As a result, the PEGylated ligand $P100_{SP}$-P4-2 incorporating the PEG4 linker with specific attachment site provided the most effective PEGylated ligand for recognition of PSMA on the cell surface.

The dual ligand combinations of peptide 1 and 2 showed modest improvement for the combination $P100_{NSP}$-2+$P100_{NSP}$-1 versus the best individual ligand, $P100_{SP}$-P4-2, FIGS. 24A-24B. The slightly greater binding affinity can be attributed to the bidentate binding mode of the dual ligand system. Furthermore, the architecture of the PEG4 linker also required optimization. The geometry of the PEG4 linker clearly affects the availability of the two Lys side chains in the 8-mer peptide 1, as shown by the drop in affinity for $P100_{NSP}$-P4-2+$P100_{NSP}$-P4-1. This reduction in apparent binding affinity could be due to the formation of a crown ether-like cavity by PEG4, which naturally adopts a mushroom-like conformation.[26] Furthermore, the combination has affinity equivalent to $P100_{NSP}$-P4-2, which indicates complete loss of ligand 1 by the PEG4 masking; this effect renders the dual ligand combination of $P100_{NSP}$-P4-2+$P100_{NSP}$-P4-1 equivalent to the single ligand, $P100_{NSP}$-P4-2. Notably, ligand 2 lacks Lys residues, and is therefore not susceptible to such masking effects.

Controlling the PEG4 linker geometry could unmask the Lys side chains of ligand 1. After non-specific conjugation, the PEG4 linker adopts a mushroom-like conformation; such geometry could place ethylene glycol units in close proximity to the primary amines of the Lys side chains. Sandwiching PEG4 between PEG100 and the peptide ligand through the specific attachment mode, eliminates such debilitating effects, as shown by a significant increase in binding affinity for the dual ligand system $P100_{SP}$-P4-2+$P100_{SP}$-P4-1. This specific attachment incorporating the PEG4 linker evidently stretches the PEG4 providing higher apparent affinity from a constitutional isomer with different geometry, FIG. 20. Thus, in the next experiments, phage was wrapped with the dual ligand combination of $P100_{SP}$-P4-2+$P100_{SP}$-P4-1 in a 2:1 ratio.

14. PEG Spacers to Control Relative Ligand Spacing

The relative spacing between ligands governs the synergy of the chelate-based avidity effect. To achieve optimal geometry of the two ligands, the relative spacing was systematically engineered by interspersing long PEGylated ligands with smaller PEG wrappers on the phage surface. The smaller PEG wrappers could provide spacers to push apart the PEG-fused ligands on the phage surface. Generating ligands and spacers required the two wrapping modes described above—click chemistry and cysteine-maleimide reaction, on the same phage. $K_{14}$-alkyne and $K_{14}$-Cys were pre-mixed to an estimated mole fraction of 0.19, and then used to wrap the phage surface. $K_{14}$-alkyne was linked to short. PEG polymers to provide spacers. Different concentrations of the PEG polymers were explored. The ratio of ligands to spacers was empirically optimized, and a ratio of 1.5:1 provided the best levels of PSMA recognition (data. not shown). The concentration of the PEGylated ligands remained unchanged, and a 2:1 molar mixture of the two ligands was reacted with the $K_{14}$-Cys wrapped on the phage surface. A. higher net concentration of wrappers could be accommodated by the phage as the spacers allowed higher packing density.

Figure 25:
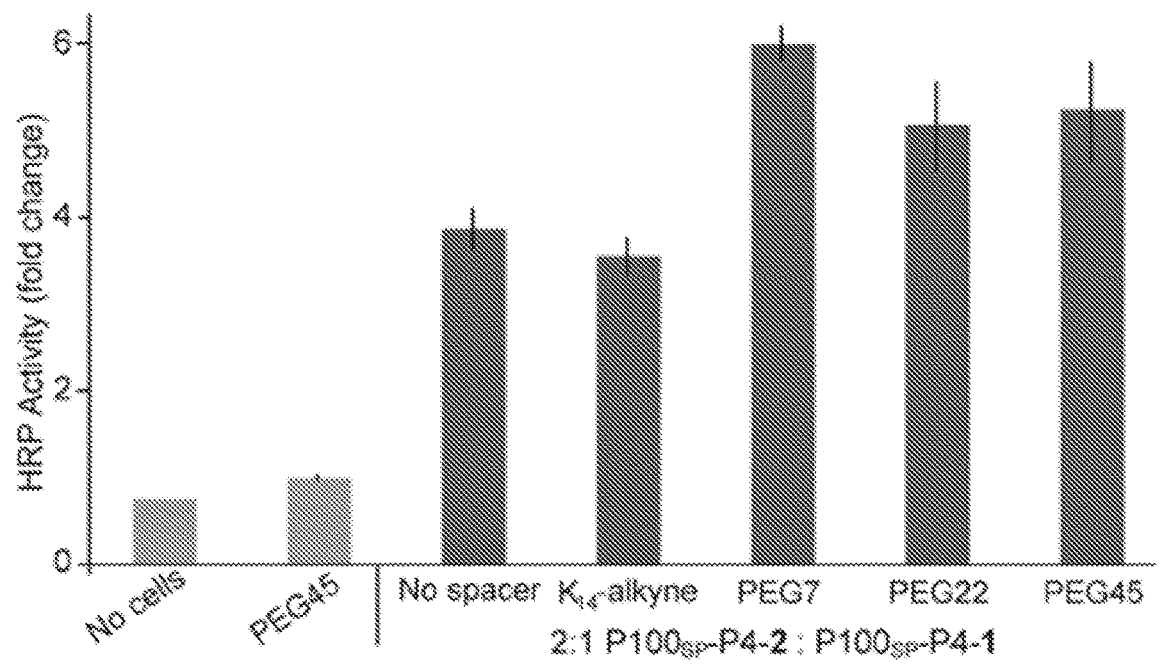
FIG. 25. shows a histogram which depicts that phage-based ELISA demonstrates the effect of smaller PEG polymers applied as spacers to optimize the geometry of the PEGylated dual ligand combination of $P100_{SP}$-P4-2+ $P100_{SP}$-P4-1. The dual ligand combination on phage was assayed with (columns 1, 2 and 5-7) and without (columns 3 and 4) PEG spacers.

The dual PSMA ligand combination described above, $P100_{SP}$-P4-2+$P100_{SP}$-P4-1, plus spacers of either PEG 7, 22 or 45, wrapped around the phage were assayed for binding to LNCaP cells, FIG. 25. All spacers significantly enhanced PSMA recognition by the displayed ligands. However, the PEG7 spacer proved most effective. The much smaller PEG7 spacer can force the ligands into adopting a more optimal geometry for effective bidentate binding, and the height of this polymer brush does not interfere with ligand binding. Longer spacers failed to boost binding affinity to the same levels. At the mole fraction of PEG used, the PEG polymers can adopt the brush conformation with the height of the polymer brush dependent on the PEG length. Interdigitation of PEG spacers with PEGylated ligands could interfere with the bidentate binding mode of the dual ligands, as shown with the longer brushes of PEG22 and 45. The addition of $K_{14}$-alkyne without conjugated PEG spacers has no effect on binding affinity. Thus, the increased packing of wrappers is also not a contributing factor, as enhanced binding results from the improved geometry through addition of spacers.

15. Selective Recognition of PSMA Positive Cells

To demonstrate specificity for PCa cells by these chemically modified phage, binding to different cell lines was compared. LNCaP cells can model early or late stage cancer cells, through variation in their culture conditions. The majority of PCa cases gain resistance to therapies based on androgen ablation.[38] The LNCaP cell line, a model for early stage PCa, is androgen sensitive but gradually loses the androgen requirement, providing a model for late stage PCa, which also mimics androgen ablation.[38,39] The latter can be simulated by culturing LNCaP cells in androgen-depleted media, referred to as LNCaP CSS (for charcoal-stripped serum).[40,41] Increased levels of PSMA are associated with androgen independent PCa.[39] Thus, both LNCaP and LNCaP CSS cell lines were assayed. The third cell line, PC3 cells, do not express PSMA, and were used as the negative control.[25,42] The following assays validate the dual ligand system for cell line discrimination and quantification of cell surface receptors.

Figure 26:
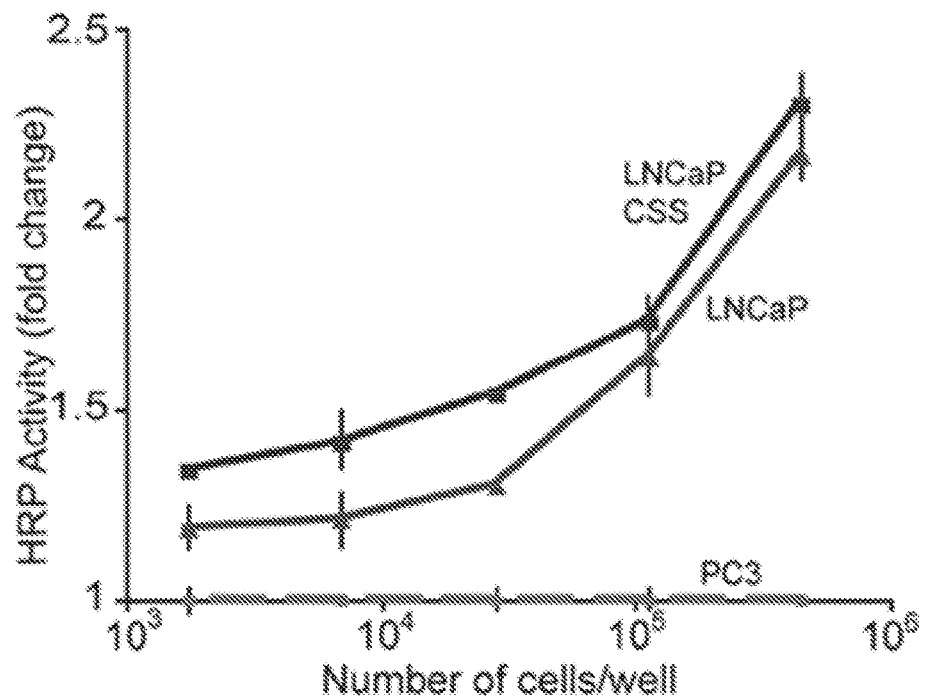
FIG. 26. A dose response curve demonstrates the specificity of PSMA detection on LNCaP cells relative to the PSMA-negative PC3 cells, as shown by cell-based ELISA. The dual ligand combination of $P100_{SP}$-P4-2+$P100_{SP}$-P4-1 and the PEG7 spacer on phage was used for specific detection of PSMA on the cell surface.

The dual ligand combination of $P100_{SP}$-P4-2+$P100_{SP}$-P4-1 and the PEG7 spacer was assayed for binding to LNCaP, LNCaP CSS, and PC3 cell lines, FIG. 26. The results demonstrate high specificity for PSMA positive LNCaP cells in a dose-dependent manner with higher apparent affinity to LNCaP CSS cells. This higher sensitivity to LNCaP CSS cells is consistent with the increase in PSMA expression resulting from the progression of the cancer cells to an androgen independent state in the LNCaP CSS model.[39]

16. Detecting PSMA on Suspended Cells and in Culture Media

Figure 27:
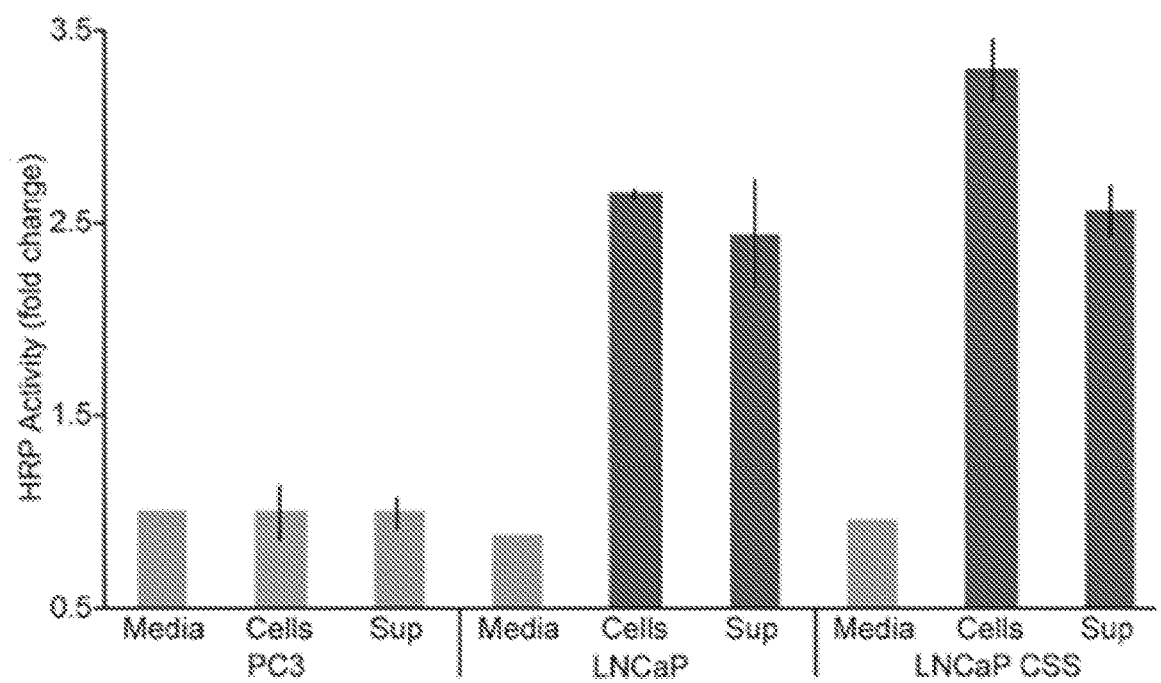
FIG. 27. shows a sandwich ELISA demonstrating capture of PSMA positive cells by the dual ligand combination of $P100_{SP}$-P4-2+$P100_{SP}$-P4-1 and the PEG7 spacer on phage. Controls are shown in a lighter color.
Figure 28:
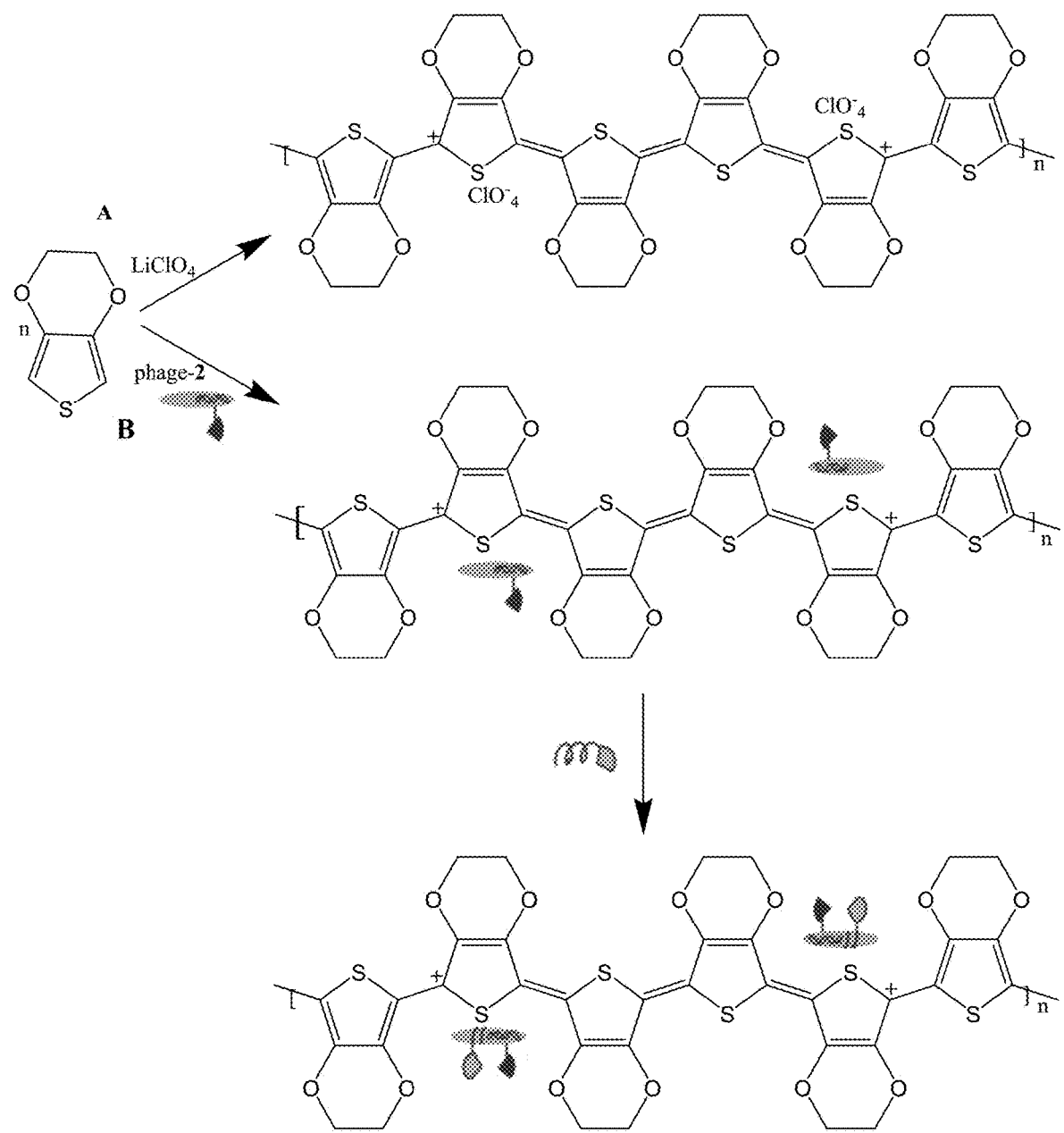
FIG. 28. shows scheme 2, polymerization of EDOT in the presence of (A) $LiClO_4$ or (B) Phage-2, followed by wrapping with KCS-1.

The tailored phage could also capture cells from solution, which is critical for future analytical applications in circulating tumor cell counting and characterization. In this experiment, a sandwich ELISA with phage bound to the microtiter plate and cells in solution was applied, FIG. 27. Again, phage wrapped with the dual ligand combination of $P100_{SP}$-P4-2+$P100_{SP}$-P4-1 and the PEG7 spacer were used. In this experiment, the capture of PSMA positive cells is detected by and proportional to cell surface PSMA concentration. PC3 cells, lacking PSMA, do not generate a significant response.

PSMA levels are elevated in the urine samples of PCa patients, and levels of this biomarker correlate with the aggressiveness of the disease.[8,43] Cultured PCa cells should release PSMA into their culture media. Thus, PSMA detection was also performed with cell culture supernatant, normalized to the volume and the number of cells. The PEGylated dual ligand combination on phage provides a significant readout for PSMA detection in the supernatant of both LNCaP and LNCaP CSS cell cultures from just 100 µL of the sample. Cell culture media from PC3 cells and fresh culture media for LNCaP, LNCaP CSS and PC3 cells serve as the negative controls. The negative controls failed to show any significant binding. The effective detection of PSMA shed by LNCaP cells, in androgen sensitive and androgen independent cells, demonstrates the use of phage re-wrapped with PEGylated ligands for future development of analytical devices and translation to the clinic.

Conclusion (Examples 7-16). In conclusion, these studies demonstrates a systematic approach to engineering the phage surface through chemical tailoring. The reported PEGylated dual ligand combination provides a foundation for applying the phage to cell-based analysis, where highly specific molecular recognition of cells is essential. Optimization of binding affinity required optimization of the PEG length, packing density, point of attachment, linkers and spacers. The versatility of PEG allows such multivariate optimization. This biocompatible polymer is widely available with diverse functionalities for bioconjugation and also has moderately predictable conformations to guide engineering. Furthermore, we demonstrate control over the relative spatial configuration of the ligands using small PEG polymers interdigitated with larger PEG brushes in a general approach applicable to many binding optimization studies. Most importantly, these synthetic phage could readily distinguish PSMA-positive from PSMA-negative cells, and also identify more aggressive PCa tumor cells. In the future, we will apply such phage to the capture and detection of circulating tumor cells.

17. Materials and Methods

All chemicals and reagents were purchased from Sigma-Aldrich, and used as received unless otherwise noted. KO7 helper phage, horseradish peroxidase conjugated to α-M13 monoclonal antibody were purchased from GE Healthcare Life Sciences. PSMA was a generous gift. 4-Azido butanoic acid was a generous gift. 4-Pentynoic acid (GFS Chemicals, Inc.), 0-benzotriazole-N,N,N,N-tetramethyl-uronium-hexafluoro-phosphate, HBTU (GL Biochem Ltd.), Tris-(benzyltriazolylmethyl) amine (Anaspec Inc.), triethyammonium acetate buffer (Fluka Biochemika) and sorbitan monolaurate, TWEEN-20 (EMD Science) were used as received. Milli-Q UV water was used for the preparation of solutions.

M13 Bacteriophage Propagation

The M13 phage display vectors (phagemids) containing the genes encoding P8 fused to either peptide 1 or 2 were used to transform $CaCl_2$) competent *E. coli* XL-1 Blue cells, before plating onto LB agar plates supplemented with 50 µg/mL carbenicilin. See e.g., Mohan, K.; et al., *J. Am. Chem. Soc.* 2013, 135, 7761-7767. The cells were grown at 37° C. in 2 mL 2YT media supplemented with carbenicilin (50 µg/mL) until the culture reached log-phase growth. The culture was then infected with KO7 helper phage ($10^{10}$ phage/mL) and shaken at 250 rpm for 1 h at 37° C. The starting culture was then transferred to 75 mL 2YT/carbenicilin media supplemented with kanamycin (10 µg/mL). The culture was shaken at 250 rpm for 16-18 h at 37° C. To isolate the phage from the cells, the culture was centrifuged for 10 min at 10 krpm at 4° C. The supernatant was decanted into separate tubes, and the phage was precipitated by addition of ⅕th volume of PEG-NaCl (2.5 M NaCl, 20% PEG-8000). The solution was placed on ice for 1 h. Next, the phage were recovered by centrifugation for 20 min at 10 krpm. The supernatant was discarded, and the phage pellet was resuspended in phosphate-buffered saline (PBS, 135 mM NaCl, 2.50 mM KCl, 8.00 mM $Na_2HPO_4$, 30.0 mM $KH_2PO_4$, pH 7.2) with added 0.05% TWEEN-20. After additional centrifugation for 10 min at 15 krpm, the phage precipitation step was repeated as described above. Phage concentration was determined by UV absorbance at 268 nm ($OD_{268}$=8.31 nM).

For incorporation of phage in the virus-PEDOT films, the phage pellet obtained after the above protocol was re-suspended in aqueous $LiClO_4$ (12 mM) solution.

Solid Phase Peptide Synthesis

The peptides were synthesized at 0.40 mmol scale following the standard procedures for solid-phase peptide synthesis with Fmoc-protected amino acids on Rink-amide resin (Novabiochem). The last coupling step was performed with 4-azido butanoic acid or 4-pentynoic acid to yield the azide- or alkyne-functionalized peptides respectively. The synthesized peptides with a carboxamide C-terminus were cleaved from the resin by treatment with 9.5 mL trifluoro-acetic acid, 250 µL triisopropylsilane and 250 µL, of water in a $N_2$ atmosphere for 3 h. The cleavage mixture was filtered from the resin, and the peptides were precipitated by addition of ice-cold diethyl ether. The peptides were recovered by centrifugation at 3K rpm for 20 min at 4° C., and resuspended in water before lyophilization. The peptides were characterized by MALDI-TOF mass spectrometry, followed by reverse phase HPLC purification with a $C_{18}$ column. Fractions containing the purified peptides were combined and concentrated using rotary evaporation, followed by lyophilization. The purified peptides were further characterized by MALDI-TOF mass spectrometry. The calculated m/z for peptide-1 [M$^+$] 1349.67, found 1349.77. The calculated m/z for peptide-2 [M$^+$] 2040.28, found 2040.23. The calcd m/z for peptide-1 with the PEG4 linker is [M$^+$] 1510.80, found 1511.78. The calcd m/z for peptide-2 with the PEG4 linker is [M$^+$] 2201.02, found 2202.06. The calcd m/z for alkyne-functionalized $K_{14}$-alkyne peptide [M+Na]$^+$ 1914.37, found 1914.18. The calcd m/z for $K_{14}$-Cys peptide [M$^{3+}$] 638.79, found 638.79.

Click Chemistry Reaction for the Synthesis of $K_{CS}$-2

The protocol for the synthesis of PEGylated oligolysines was adapted from Lumiprobe Corporation's protocol, as described previously. See e.g., Mohan, K.; et al., *J. Am. Chem. Soc.* 2013, 135, 7761-7767; Lumiprobe: at website www.lumiprobe.com/protocols/click-chemistry-dna-labeling (accessed Sep. 7, 2011). As a representative protocol for the click chemistry reaction, the synthesis of $K_{CS}$-2 was adapted from Lumiprobe Corporation's protocol for application to peptides with the following exceptions. First, the reaction was performed at 200 µM azide-derivatized peptide concentration in 75% acetonitrile and 25% water. Second, water was used as the solvent, in place of DMSO. Third, a final concentration of 1 mM $CuSO_4$ was used, and the acetone precipitation step was skipped. Product formation was confirmed by MALDI-TOF mass spectrometry before purification. For purification, the reaction mixture was first concentrated using 2 kD MW cut-off micro concentrators, and then further concentrated under high vacuum to approximately 100 pt. The concentrated reaction mixture was purified using reverse-phase analytical HPLC. Purified product was then subjected to reverse-phase analytical HPLC and MALDI-TOF, to verify purity and confirm identity, respectively. The calculated m/z for $K_{CS}$-1 [M$^+$] 3240.05, found 3240.08. The calculated m/z for $K_{CS}$-2 [M$^+$] 3930.31, found 3930.35.

Synthesis of PEGylated Ligands—Specific Attachment Mode

The protocol for the synthesis of the PEGylated ligands was adapted from the solid phase peptide synthesis and click chemistry described above. In a glass test tube, 40 µL of 1 mM Mal-PEG100-NH$_2$ (in water), 12 µL of 10 mM pentynoic acid (in water), 12 µL of 10 mM HBTU (in NMP), 40 µL of DIPEA and 296 µL of HPLC grade water were combined and stirred at room temperature for 2 h. For increased scale, multiple reactions at this volume were run in parallel. The reaction mixtures were then diluted with an equal volume HPLC grade water before concentration to 1/10th volume using 2K MWCO concentrators (Sartorius).

For the next step of the synthesis, ~50 µL of the alkyne-functionalized-PEG100-Mal, obtained as described above, was conjugated to azide-functionalized peptide ligands (final concentration of 40 µM) by click chemistry as before[1,2]. The reaction mixture was stirred overnight at room temperature. Four identical reactions were run in parallel. The four reaction mixtures were then combined and concentrated to 1/4th volume using 3K MWCO concentrators. Next, the resultant solution was diluted with an equal volume of HPLC grade water before concentrating to ~1/2 volume using 5K MWCO concentrators. The concentrated reaction mixture was purified using reverse-phase analytical HPLC and characterized by MALDI-TOF mass spectrometry. Data exhibited the characteristic polydispersity of a PEG polymer with the expected mass for the conjugated material.

For the non-specific attachment mode, the PEGylated ligands were synthesized in the reverse order. The azide-functionalized peptides were first conjugated to pentynoic acid using click chemistry. The resultant peptide was then coupled to Mal-PEG100-NH$_2$ using HBTU and DIPEA as described above.

Cell Growth

The cell lines were grown as monolayers in media supplemented with 10% fetal bovine serum (Cellgro), 1 mM sodium pyruvate (Kularatne, S. A.; et al. *Mol. Pharm.* 2009, 6, 780-789.) and 1% penicillin-streptomycin-glutamine in a 5% CO$_2$ and 95% air-humidified atmosphere at 37° C. LNCaP cells were cultured in RPMI 1640 media. For studies with LNCaP cells cultured in charcoal-stripped serum (LNCaP CSS cells), LNCaP cells were washed with PBS and then incubated with phenol free RPMI 1640 media supplemented with 10% charcoal-stripped serum (Cellgro) for five minutes. The cells were again washed with PBS, and provided fresh media.' PC3 cells were grown in Ham's F-12 media.

Cell-Based Phage Enzyme-Linked Immunosorbent Assay (ELISA)

The cell-based ELISA was performed as previously described by Watanabe et. al. with several modifications. See e.g., Watanabe, K.; et al., *Clin. Biochem.* 2001, 34, 291-295. Cells were detached with Trypsin-EDTA, resuspended in PBS, and then collected by centrifuging at 1200 rpm for 5 min. The cells were further washed with PBS and then concentrated as in the previous step. The concentration of the cells was adjusted to 4.5×10$^6$ cells/mL in PBS using a hemocytometer, and 100 µL was aliquoted to specific wells of a 96-well microtiter (Nunc Maxisorp). Next, 50 µL of 0.15% of glutaraldehyde in PBS was added to the wells at 4° C., and the solution was gently mixed by pipetting. The ELISA plate was then centrifuged at 1200 rpm for 10 min at 4° C., followed by overnight incubation at 4° C. The cell solution was gently removed, and the wells were blocked with 200 µL/well of blocking buffer containing 100 mM glycine, 1% gelatin and 0.1% w/v BSA (bovine serum albumin) in PBS. The plate was incubated overnight (~20-22 h) at room temperature.

Separately, phage wrapped with PEG and PEGylated ligands were prepared. Phage (10 nM in 100 µL) and 1 µL of $K_{14}$-alkyne (525 µM in water) were thoroughly mixed by pipetting ~25 times. For phage wrapped with PEGylated ligands, phage were mixed with 0.75 µL of $K_{14}$-Cys (525 µM in water). For mixed wrapping on phage surface, 0.5 µL of $K_{14}$-alkyne was pre-mixed with 0.75 µL of $K_{14}$-Cys, and then mixed with 100 µL of 10 nM phage. The solution was shaken at room temperature for 15 min on an orbital shaker. Next, 2 µL of PEGylated ligand (625 µM in water) was added to the appropriate wells. For the dual ligand combinations, the PEGylated ligands were pre-mixed in the desired ratio (2:1 for example), and then 2 µL of the mixture was added to the appropriate wells. The solutions were gently mixed by pipetting, and incubated overnight at 4° C.

Next, the click reaction was performed, as previously described, but with the following modifications.[1,2] Triethylammonium acetate was added to a final concentration of 50 mM, followed by the addition of 1.5 µL of 1 mM azide-functionalized PEG. The solutions were mixed by pipetting. Next, ascorbic acid was added to a final concentration of 1 mM and the solutions were mixed by gently pipetting. Next, copper sulfate was added to a final concentration of 1.5 mM, followed by pipetting to mix the solutions. Water was added to the other wells to maintain a consistent phage concentration. The plate was incubated at room temperature for 30 min.

The wells on the ELISA plate were then incubated with the phage samples. The blocking buffer was removed and the wells were gently washed two times with PBS. Next, the phage solution was added to the respective wells and incubated for 45 min. The phage solution was removed, and the wells were washed three times with 300 µL/well of wash buffer PT (0.05% TWEEN-20 in PBS), once with PBS, and then incubated with horseradish-peroxidase-conjugated anti-M13 antibody (100 µL/well, 1:5000 dilution in PBS) for 40 min. The wells were washed three times with PT and once with PBS. The plate was then developed by incubating with HRP substrate solution (100 µL/well; 1 mg/mL o-phenylenediamine dihydrochloride and 0.02% w/v $H_2O_2$) in citric acid buffer (50 mM citric acid, 50 mM $Na_2HPO_4$, pH 5.0). The HRP activity was measured spectrophotometrically at 450 nm using a microtiter plate reader (Bio-Tek). The absorbance at 630 nm was subtracted from the absorbance at 450 nm to eliminate background.

Phage-Based Sandwich ELISA for Cell Capture:

In this phage capture ELISA, specific wells of a 96-well microtiter plate were coated with 100 µL/well of a solution of 10 nM phage pre-wrapped with oligolysine wrappers, as described above. The plate was incubated for 1 h on a shaker at room temperature. The coating solution was removed, and the wells were blocked with 200 µL/well of 0.2% w/v solution of BSA in PBS for 30 min, and washed two times with PT. Next, 98 µL PBS was added per well, followed by PEGylated ligands and incubated overnight at 4° C. Azide-functionalized PEG were then conjugated as described above. Separately, the cells were collected and the concentration adjusted as described above; the ELISA plate was then incubated with 100 µL/well of the cell solution or media for 1 h. The wells were washed with PBS and incubated with 100 µL/well of the anti-PSMA antibody, YPSMA antibody (Abcam) at 1:1000 dilution. The wells were then washed with PBS, followed by incubation with horseradish-peroxidase-conjugated anti-mouse antibody (Sigma) at 1:1000 dilution. The levels of phage binding were quantified as described above.

PSMA Targeting Enzyme-Linked Immunosorbent Assay (ELISA)

In a phage-based ELISA, specific wells of a 96-well microtiter plate (Nunc Maxisorp) were coated with 100 µL/well of a solution of PSMA (5.56 or 11.1 nM) monomer or dimer protein diluted in PBS. The plate was incubated for 1 h on a shaker at room temperature. The coating solution was removed, and the wells were blocked with 320 µL/well of 0.2% w/v solution of BSA in PBS for 30 min, and washed three times with 300 µL/well of wash buffer PT (0.05% TWEEN-20 in PBS). Separately, phage-displayed PSMA-binding peptides were serially diluted along with a negative control (KO7) in phage dilution buffer, PBT (0.1% w/v BSA, 0.1% TWEEN-20 in PBS). The wells on the ELISA plate were then incubated with the phage samples (100 µL/well) for 1 h. The wells were washed five times with PT and then incubated with horseradish-peroxidase-conjugated anti-M13 antibody (100 µL/well, 1:5000 dilution in PBT) for 30 min. The wells were washed three times with PT, and two times with PBS. The plate was then developed by incubating with HRP substrate solution (100 µL/well; 1 mg/mL o-phenylenediamine dihydrochloride and 0.02% w/v $H_2O_2$) in citric acid buffer (50 mM citric acid, 50 mM $Na_2HPO_4$, pH 5.0). Following an appropriate incubation time, HRP activity was measured spectrophotometrically at 450 nm using a microtiter plate reader (Bio-Tek).

Phage-based wrapping ELISA: Phage (5 nM in 225 µL) and 2 µL of the purified cycloaddition reaction product, $K_{CS}$-1/2 (308.7 µM) in water: acetonitrile (60:40), were mixed and serially diluted in PBT. The solution were shaken at room temperature for 15 min on an orbital shaker. After blocking the ELISA plate, the wells were washed three times with PT and once with 300 µL/well of PBS-NaCl (PBS supplemented with 0.2 M NaCl). The wrapped-phage solutions (100 µL/well) were then transferred to the appropriate wells of an ELISA plate, prepared as described above. The wells were washed four times with PT and two times with PBS, followed by incubation with horseradish-peroxidase-conjugated anti-M13 antibody (1:15000 dilution). The wells were then washed six times with wash buffer PT, and two times with PBS. Levels of phage binding were quantified as described above.

Synthesis of Phage-PEDOT Films

A circular gold electrode (CH instruments) was manually polished with three diamond polishing pastes (Ted Pella) having particle sizes of 1, 0.5 and 0.25 µm on a polishing microcloth (Buehler), and sonicated in nanopure water for 10 min. A flame-cleaned platinum film electrode was used as the counter electrode. The electrode was placed in the virus-PEDOT plating solution (12.5 mM $LiClO_4$, 2 mM EDOT and 3 nM phage). Electropolymerization occurred by cycling between 0.2 and 1.15 V vs Ag/AgCl reference electrode for 10 cycles using a PARSTAT 2273 controlled with POWERCV software (Princeton Applied Research, Oak Ridge, Tenn.), at a scan rate of 20 mV/s. Synthesized films were rinsed with Milli-Q water and transferred to the run buffer, 0.1% TWEEN 20 in phosphate buffered fluoride (PBF, 4.2 mM $Na_2HPO_4$, 1.5 mM $KH_2PO_4$ and 140 mM NaF, pH 7.2).

SEM Analysis

Scanning electron microscopy was performed using a Philips XL30 FEG SEM at a 10 kV operating voltage. The samples were coated with a thin layer of Ir by sputter coating prior to SEM analysis.

Impedance Measurements

Freshly synthesized virus-PEDOT films were rinsed with Milli-Q water and then equilibrated in PBF-TWEEN buffer for 10 min. Then five consecutive EIS scans were acquired using a PARSTAT 2273 potentiostat controlled by POWERSine software (Princeton Applied Research, Oak Ridge, Tenn.), at 50 frequency data points spanning 0.1 Hz to 1 MHz with a 10 mV voltage modulation amplitude. The electrode was then rinsed with water, and incubated with PSMA for 30 min followed by rinsing with water and PBF-TWEEN. The electrode was returned to the run buffer and equilibrated for 10 min before acquisition of five consecutive EIS scans. The data was fit to the Hill equation using GraphPad Prism.[2]

For biosensing with wrapped-viruses, the synthesized virus-PEDOT films were rinsed with Milli-Q water, and then incubated with $K_{CS}$-1 (308.7 µM) for 15 min. The electrode was then rinsed with Water and PBF-TWEEN, followed by incubation with PSMA. EIS scans were acquired as described above. For synthetic urine runs, the electrode with the bio-affinity matrix was incubated with PSMA in synthetic urine to achieve the desired concentration. The EIS scans were acquired as described above.

References (Example 1-6)

(1) Siegel, R.; Naishadham, D.; Jemal, A. CA-Cancer J. Clin. 2013, 63, 11-30. (2) Moyer, V. A. Ann. Int. Med. 2012, 157, 120-134. (3) Madu, C. O.; Lu, Y. L. J. Cancer 2010, 1, 150-177. (4) Murphy, G. P.; Kenny, G. M.; Ragde, H.; Wolfert, R. L.; Boynton, A. L.; Holmes, E. H.; Misrock, S. L.; Bartsch, G.; Klocker, H.; Pointner, J.; Reissigl, A.; McLeod, D. G.; Douglas, T.; Morgan, T.; Gilbaugh, J. Urology 1998, 51, 89-97. (5) Sokoloff, R. L.; Norton, K. C.; Gasior, C. L.; Marker, K. M.; Grauer, L. S. Prostate 2000, 43, 150-157. (6) Xiao, Z.; Adam, B.-L.; Cazares, L. H.; Clements, M. A.; Davis, J. W.; Schellhammer, P. F.; Dalmasso, E. A.; Wright, G. L. Cancer Res. 2001, 61, 6029-6033. (7) Schülke, N.; Varlamova, O. A.; Donovan, G. P.; Ma, D.; Gardner, J. P.; Morrissey, D. M.; Arrigale, R. R.; Zhan, C.; Chodera, A. J.; Surowitz, K. G.; Maddon, P. J.; Heston, W. D. W.; Olson, W. C. Proc. Natl. Acad. Sci. U.S.A. 2003, 100, 12590-12595. (8) Chuang, A.-Y.; DeMarzo, A. M.; Veltri, R. W.; Sharma, R. B.; Bieberich, C. J.; Epstein, J. I. Am. J. Surg. Pathol. 2007, 31, 1246-1255. (9) Su, S. L.; Huang, I. P.; Fair, W. R.; Powell, C. T.; Heston, W. D. Cancer Res. 1995, 55, 1441-1443. (10) Petrenko, V. A.; Vodyanoy, V. J. J. Microbiol. Methods 2003, 53, 253-262. (11) Nanduri, V.; Sorokulova, I. B.; Samoylov, A. M.; Simonian, A. L.; Petrenko, V. A.; Vodyanoy, V. Biosens. Bioelectron. 2007, 22, 986-992. (12) Ionescu, R. E.; Cosnier, S.; Herrmann, S.; Marks, R. S. Anal. Chem. 2007, 79, 8662-8668. (13) Smith, G. P. Science 1985, 228, 1315-1317. (14) Kehoe, J. W.; Kay, B. K. Chem. Rev. 2005, 105, 4056-4072. (15) Levin, A. M.; Weiss, G. A. Mol. Biosyst. 2006, 2, 49-57. (16) Weiss, G. A.; Penner, R. M. Anal. Chem. 2008, 80, 3082-3089. (17) Diaz, J. E.; Yang, L.-M. C.; Lamboy, J. A.; Penner, R. M.; Weiss, G. A. Methods Mol. Biol. 2008, 504, 255-274. (18) Yang, L.-M. C.; Diaz, J. E.; McIntire, T. M.; Weiss, G. A.; Penner, R. M. Anal. Chem. 2008, 80, 5695-5705. (19) Yang, L.-M. C.; Tam, P. Y.; Murray, B. J.; McIntire, T. M.; Overstreet, C. M.; Weiss, G. A.; Penner, R. M. Anal. Chem. 2006, 78, 3265-3270. (20) Arter, J. A.; Taggart, D. K.; McIntire, T. M.;

Penner, R. M.; Weiss, G. A. Nano Lett. 2010, 10, 4858-4862. (21) Donavan, K. C.; Arter, J. A.; Pilolli, R.; Cioffi, N.; Weiss, G. A.; Penner, R. M. Anal. Chem. 2011, 83, 2420-2424. (22) Arter, J. A.; Diaz, J. E.; Donavan, K. C.; Yuan, T.; Penner, R. M.; Weiss, G. A. Anal. Chem. 2012, 84, 2776-2783. (23) Lamboy, J. A.; Arter, J. A.; Knopp, K. A.; Der, D.; Overstreet, C. M.; Palermo, E. F.; Urakami, H.; Yu, T.-B.; Tezgel, O.; Tew, G. N.; Guan, Z.; Kuroda, K.; Weiss, G. A. J. Am. Chem. Soc. 2009, 131, 16454-16460. (24) Lamboy, J. A.; Tam, P. Y.; Lee, L. S.; Jackson, P. J.; Avrantinis, S. K.; Lee, H. J.; Corn, R. M.; Weiss, G. A. ChemBioChem 2008, 9, 2846-2852. (25) Welsh, L. C.; Symmons, M. F.; Sturtevant, J. M.; Marvin, D. A.; Perham, R. N. J. Mol. Biol. 1998, 283, 155-177. (26) Fundamental Immunology, 6th ed.; Paul, W., Ed.; Lippincott Williams & Wilkins: New York, 2008; p 164. (27) Murase, K.; Morrison, K. L.; Tam, P. Y.; Stafford, R. L.; Jurnak, F.; Weiss, G. A. Chem. Biol. 2003, 10, 161-168. (28) Rostovtsev, V. V.; Green, L. G.; Fokin, V. V.; Sharpless, K. B. Angew. Chem., Int. Ed. 2002, 41, 2596-2599. (29) Erlanson, D. A. Top. Curr. Chem. 2012, 317, 1-32. (30) Sharma, P. S.; Pietrzyk-Le, A.; D'Souza, F.; Kutner, W. Anal. Bioanal. Chem. 2012, 402, 3177-3204. (31) Hill, A. V. J. Physiol. (London) 1910, 40, 4-7. (32) Mccurdy, D.; Lin, Z.; Inn, K. G. W.; Iii, R. B.; Wagner, S.; Efurd, D. W.; Steiner, R.; Duffy, C.; Hamilton, T. F.; Brown, T. A.; Marchetti, A. A. J. Radioanal. Nucl. Chem. 2005, 263, 447-455. (33) Clinical Laboratory Medicine, 2nd ed.; McClatchey, K. D., Ed.; Lippincott Williams & Wilkins: Maryland, 2002; p 381. (34) Donavan, K. C.; Arter, J. A.; Weiss, G. A.; Penner, R. M. Langmuir 2012, 28, 12581-12587. J. A. Lamboy, P. Y. Tam, L. S. Lee, P. J. Jackson, S. K. Avrantinis, H. J. Lee, et al. ChemBioChem. 9 (2008) 2846-2852. J. A. Lamboy, J. A. Arter, K. A. Knopp, D. Der, C. M. Overstreet, E. F. Palermo, et al., J. Am. Chem. Soc. 131 (2009) 16454-16460. K. Mohan, K. C. Donavan, J. A. Arter, R. M. Penner, G. A. Weiss, J. Am. Chem. Soc. 135 (2013) 7761-7767.

References (Example 7-16).

(1) Joosse, S. A.; Gorges, T. M.; Pantel, K. EMBO Mol. Med. 2014, doi: 10.15252/emmm.201303698; (2) Mehlen, P.; Puisieux, A. Nat. Rev. Cancer 2006, 6, 449-458; (3) Siegel, R.; Ma, J.; Zou, Z.; Jemal, A. CA. Cancer J. Clin. 2014, 64, 9-29; (4) Mohan, K.; Donavan, K. C.; Arter, J. A.; Penner, R. M.; Weiss, G. A. J. Am. Chem. Soc. 2013, 135, 7761-7767; (5) Schülke, N.; Varlamova, O. A.; Donovan, G. P.; Ma, D.; Gardner, J. P.; Morrissey, D. M.; Arrigale, R. R.; Zhan, C.; Chodera, A. J.; Surowitz, K. G.; Maddon, P. J.; Heston, W. D. W.; Olson, W. C. Proc. Natl. Acad. Sci. USA 2003, 100, 12590-12595; (6) Chuang, A.-Y.; DeMarzo, A. M.; Veltri, R. W.; Sharma, R. B.; Bieberich, C. J.; Epstein, J. I. Am. J. Surg. Pathol. 2007, 31, 1246-1255; (7) Kawakami, M.; Nakayama, J. Cancer Res. 1997, 57, 2321-2324; (8) Sokoloff, R. L.; Norton, K. C.; Gasior, C. L.; Marker, K. M.; Grauer, L. S. Prostate 2000, 43, 150-157; (9) Mohan, K.; Weiss, G. A. Anal. Biochem. 2014, 453, 1-3; (10) Arter, J. A.; Diaz, J. E.; Donavan, K. C.; Yuan, T.; Penner, R. M.; Weiss, G. A. Anal. Chem. 2012, 84, 2776-2783; (11) Smith, G. P. Science 1985, 228, 1315-1317; (12) Sidhu, S. S.; Weiss, G. A. In Phage Display: A Practical Approach; Lowman, H. B.; Clackson, T., Eds.; Oxford University Press: New York, 2004; pp. 27-42; (13) Scott, J. K.; Smith, G. P. Science 1990, 249, 386-90; (14) Welsh, L. C.; Symmons, M. F.; Sturtevant, J. M.; Marvin, D. A.; Perham, R. N. J. Mol. Biol. 1998, 283, 155-177; (15) Carrico, Z. M.; Farkas, M. E.; Zhou, Y.; Hsiao, S. C.; Marks, J. D.; Chokhawala, H.; Clark, D. S.; Francis, M. B. ACS Nano 2012, 6, 6675-6680; (16) Trepel, M.; Arap, W.; Pasqualini, R. Curr. Opin. Chem. Biol. 2002, 6, 399-404; (17) Abbineni, G.; Modali, S.; Safiejko-Mroczka, B.; Petrenko, V. A.; Mao, C. Mol. Pharm. 2010, 7, 1629-1642; (18) Petrenko, V. A.; Jayanna, P. K. FEBS Lett. 2014, 588, 341-349; (19) Jayanna, P. K.; Torchilin, V. P.; Petrenko, V. A. Nanomedicine. 2009, 5, 83-89; (20) Wang, T.; Yang, S.; Petrenko, V. A.; Torchilin, V. P. Mol. Pharm. 2010, 7, 1149-1158; (21) Lamboy, J. A.; Tam, P. Y.; Lee, L. S.; Jackson, P. J.; Avrantinis, S. K.; Lee, H. J.; Corn, R. M.; Weiss, G. A. ChemBioChem 2008, 9, 2846-2852; (22) Lamboy, J. A.; Arter, J. A.; Knopp, K. A.; Der, D.; Overstreet, C. M.; Palermo, E. F.; Urakami, H.; Yu, T.-B.; Tezgel, O.; Tew, G. N.; Guan, Z.; Kuroda, K.; Weiss, G. A. J. Am. Chem. Soc. 2009, 131, 16454-16460; (23) Dozmorov, M. G.; Hurst, R. E.; Culkin, D. J.; Kropp, B. P.; Frank, M. B.; Osban, J.; Penning, T. M.; Lin, H.-K. Prostate 2009, 69, 1077-1079; (24) Horoszewicz, J. S.; Leong, S. S.; Chu, T. M.; Wajsman, Z. L.; Friedman, M.; Papsidero, L.; Kim, U.; Chai, L. S.; Kakati, S.; Arya, S. K.; Sandberg, A. A. Prog. Clin. Biol. Res. 1980, 37, 115-132; (25) Sobel, R. E.; Sadar, M. D. J. Urol. 2005, 173, 342-359; (26) Marsh, D.; Bartucci, R.; Sportelli, L. Biochim. Biophys. Acta—Biomembr. 2003, 1615, 33-59; (27) Crawford, J. Cancer Treat. Rev. 2002, 28, 7-11; (28) Knop, K.; Hoogenboom, R.; Fischer, D.; Schubert, U. S. Angew. Chem. Int. Ed. Engl. 2010, 49, 6288-6308; (29) Pai, S. S.; Przybycien, T. M.; Tilton, R. D. Langmuir 2010, 26, 18231-18238; (30) Fishburn, C. S. J. Pharm. Sci. 2008, 97, 4167-4183; (31) Loo, C.; Lin, A.; Hirsch, L.; Lee, M.-H.; Barton, J.; Halas, N.; West, J.; Drezek, R. Technol. Cancer Res. Treat. 2004, 3, 33-40; (32) Loo, C.; Lowery, A.; Halas, N.; West, J.; Drezek, R. Nano Lett. 2005, 5, 709-711; (33) Levin, C. S.; Bishnoi, S. W.; Grady, N. K.; Halas, N. J. Anal. Chem. 2006, 78, 3277-3281; (34) Sarma, M.; Chatterjee, T.; Das, S. K. RSC Adv. 2012, 2, 3920-3926; (35) Greenwald, R. B.; Choe, Y. H.; McGuire, J.; Conover, C. D. Adv. Drug Deliv. Rev. 2003, 55, 217-250; (36) Montesano, G.; Bartucci, R.; Belsito, S.; Marsh, D.; Sportelli, L. Biophys. J. 2001, 80, 1372-13783; (37) Harris, J. M.; Martin, N. E.; Modi, M. Clin. Pharmacokinet. 2001, 40, 539-551; (38) Tovar, C.; Higgins, B.; Kolinsky, K.; Xia, M.; Packman, K.; Heimbrook, D. C.; Vassilev, L. T. Mol. Cancer 2011, 10, 49-59; (39) Denmeade, S. R.; Sokoll, L. J.; Dalrymple, S.; Rosen, D. M.; Gady, A. M.; Bruzek, D.; Ricklis, R. M.; Isaacs, J. T. Prostate 2003, 54, 249-257; (40) Culig, Z.; Hoffmann, J.; Erdel, M.; Eder, I. E.; Hobisch, A.; Hittmair, A.; Bartsch, G.; Utermann, G.; Schneider, M. R.; Parczyk, K.; Klocker, H. Br. J. Cancer 1999, 81, 242-251; (41) Iwasa, Y.; Mizokami, A.; Miwa, S.; Koshida, K.; Namiki, M. Int. J. Urol. 2007, 14, 233-239; (42) Ghosh, A.; Wang, X.; Klein, E.; Heston, W. D. W. Cancer Res. 2005, 65, 727-731; (43) Su, S. L.; Huang, I. P.; Fair, W. R.; Powell, C. T.; Heston, W. D. Cancer Res. 1995, 55, 1441-1443.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Embodiments

Embodiment 1. A whole viral particle comprising a charged protein coat, said charged protein coat comprising a charged coat protein electrostatically bound to a functionalized charged polymer, wherein said functionalized charged polymer comprises a charged polymer covalently bound to a chemically reactive functional group.

Embodiment 2. A whole viral particle comprising a charged protein coat, said charged protein coat comprising a charged coat protein electrostatically bound to a charged polymer conjugate, wherein said charged polymer conjugate comprises a charged polymer covalently bound to a hydrophilic organic polymer.

Embodiment 3. The whole virus particle of embodiment 1 or embodiment 2, wherein said charged coat protein is a negatively charged coat protein.

Embodiment 4. The whole virus particle of embodiment 1 or embodiment 2, wherein said charged coat protein is a positively charged coat protein.

Embodiment 5. The whole virus particle of one of embodiments 1 to 4, wherein said charged polymer is a cationic polymer.

Embodiment 6. The whole virus particle of one of embodiments 1 to 4, wherein said charged polymer is an anionic polymer.

Embodiment 7. The whole virus particle of one of embodiments 2 to 6, wherein said hydrophilic organic polymer is a polyethylene glycol.

Embodiment 8. The whole virus particle of one of embodiments 1 to 7, wherein said chemically reactive functional group is a click chemistry reactive functional group.

Embodiment 9. The whole virus particle of embodiment 8, wherein said click chemistry reactive functional group is an alkyne, an azide, a maleimide or a thiol.

Embodiment 10. The whole virus particle of one of embodiments 1 to 9, wherein the chemically reactive functional group is a bioorthoganol chemically reactive functional group.

Embodiment 11. The whole virus particle of one of embodiments 1 to 10, wherein the whole viral particle is a whole bacteriophage viral particle.

Embodiment 12. The whole virus particle of one of embodiments 1 to 11, wherein the whole viral particle is an M13 virus particle.

Embodiment 13. The whole virus particle of one of embodiments 1 to 12, wherein said charged coat protein comprises a genetically encoded ligand.

Embodiment 14. The whole virus particle of one of embodiments 1 to 12, wherein said charged polymer is oligolysine.

Embodiment 15. The whole virus particle of one of embodiments 1 to 12, wherein said charged polymer is an oligolysine covalently bound to a chemically reactive cysteine.

Embodiment 16. A cationic electronically conductive polymer electrostatically bound to a first whole viral particle, said first whole viral particle comprising a negatively charged protein coat wherein said negatively charged protein coat comprises a coat protein electrostatically bound to a cationic polymer or a cationic polymer conjugate.

Embodiment 17. The cationic electronically conductive polymer of embodiment 16, wherein said negatively charged coat protein comprises a mixture of wild-type coat protein and coat protein fused to a genetically encoded ligand.

Embodiment 18. The cationic electronically conductive polymer of one of embodiments 16 to 17, wherein said cationic polymer is electrostatically bound to a second whole viral particle.

Embodiment 19. The cationic electronically conductive polymer of one of embodiments 16 to 18, wherein said cationic polymer is polyethylene imine.

Embodiment 20. The cationic electronically conductive polymer of one of embodiments 16 to 19, wherein said second whole viral particle comprises a second genetically encoded ligand.

Embodiment 21. The cationic electronically conductive polymer of one of embodiments 16 to 20, wherein said second genetically encoded ligand is different from said first genetically encoded ligand.

Embodiment 22. The cationic electronically conductive polymer of one of embodiments 16 to 20, wherein said second genetically encoded ligand is identical to said first genetically encoded ligand.

Embodiment 23. The cationic electronically conductive polymer of one of embodiments 16 to 22, wherein said cationic electronically conductive polymer is poly-ethylene dioxythiophene.

Embodiment 24. The cationic electronically conductive polymer of one of embodiments 16 to 23, wherein said cationic electronically conductive polymer is bound to a solid support.

Embodiment 25. The cationic electronically conductive polymer of embodiment 24, wherein said solid support is gold.

Embodiment 26. The cationic electronically conductive polymer of one of embodiments 16 to 25, wherein said cationic electronically conductive polymer is part of a biosensor device.

Embodiment 27. A method of reducing non-specific binding of whole viral particles to cells comprising the step of electrostatically binding a functionalized charged polymer or a charged polymer conjugate to said whole virus particle; wherein said functionalized charged polymer comprises a charged polymer covalently bound to a chemically reactive functional group, and wherein said charged polymer conjugate comprises a charged polymer covalently bound to a hydrophilic organic polymer.

Embodiment 28. A method of improving the sensitivity of a bacterial biosensor, wherein said bacterial biosensor comprises a cationic electronically conductive polymer electrostatically bound to a first whole viral particle, and said method comprises electrostatically binding a negatively charged coat protein of the whole viral particle to a cationic polymer.

Embodiment 29. The method of embodiment 28, wherein said cationic polymer is polyethylene imine.

Embodiment 30. A method of detecting a biological molecule, said method comprising: (i) combining the whole viral particle of one of embodiments 1 to 15 or the cationic electronically conductive polymer of one of embodiments 16 to 26 and a biological molecule to a reaction vessel; (ii) allowing the whole viral particle or the cationic electronically conductive polymer to specifically bind to said biological molecule; and (iii) detecting said bound biological molecule.

Embodiment 31. The method of embodiment 30, wherein said biological molecule is a cell surface protein, soluble protein, or a proteolytically released ectodomain of a protein.

Embodiment 32. The method of embodiment 31, wherein said cell surface protein forms part of a cell.

Embodiment 33. The method of embodiment 32, wherein the cell is a bacterial cell.

Embodiment 34. The method of embodiment 33, wherein the bacterial cell is an *E. coli* cell.

Embodiment 35. The method of one of embodiments 30 to 34, wherein said whole viral particle and said cationic electronically conductive polymer are capable of binding to said cell surface protein at least 50% more specifically than a whole viral particle without a functionalized cationic or anionic polymer, charged polymer conjugate, or cationic electronically conductive polymer, respectively.

Embodiment 36. The method of one of embodiments 30 to 35, wherein said reaction vessel forms part of a biosensing device.

Embodiment 37. The method of one of embodiments 30 to 36, wherein said combining is performed in aqueous media.

Embodiment 38. The method of one of embodiments 30 to 37, wherein said detecting is accomplished by measuring electrochemical impedance.

Embodiment 39. The method of one of embodiments 30 to 38, wherein said biological molecule is obtained from a patient sample.

Embodiment 40. The method of embodiment 39, wherein said patient sample is obtained from a patient suspected of having a urinary tract infection.

Embodiment 41. The method of embodiment 39, wherein said patient sample is obtained from a patient suspected of having a urinary tract infection.

Embodiment 42. The method of embodiment 40, wherein said detecting indicates the presence or absence of a urinary tract infection in said patient.

Embodiment 43. The method of embodiment 39, wherein said patient sample is obtained from a patient suspected of having cancer.

Embodiment 44. The method of embodiment 42, wherein said detecting indicates the presence or absence of cancer in said patient.

Embodiment 45. The method of embodiment 39, wherein said patient sample is obtained from a patient suspected of having prostate cancer.

Embodiment 48. A method of forming a virus particle polymer ligand conjugate: (i) contacting a first functionalized charged polymer with a charged virus coat protein, wherein said first functionalized charged polymer is covalently bound to a first chemically reactive functional group, thereby forming a virus particle polymer conjugate; (ii) contacting said first chemically reactive functional group of said virus particle polymer conjugate with a second chemically reactive functional group covalently bound to a second polymer, wherein said second polymer is covalently linked to a ligand domain, thereby forming a virus particle polymer ligand conjugate.

Embodiment 49. The method of embodiment 47, wherein said contacting of step (i) comprises electrostatically binding said first functionalized charged polymer to said charged virus coat protein.

Embodiment 50. The method of one of embodiments 47-48, wherein said first functionalized charged polymer is positively charged and wherein said charged virus coat protein is negatively charged.

Embodiment 51. The method of one of embodiments 47-48, wherein said first functionalized charged polymer is negatively charged and wherein said charged virus coat protein is positively charged.

Embodiment 52. The method of one of embodiments 47-50, wherein said first chemically reactive functional group is a click chemistry functional group.

Embodiment 53. The method of one of embodiments 47-51, wherein said click chemistry functional group is an alkyne, an azide, a thiol or a maleimide.

Embodiment 54. The method of one of embodiments 47-52, wherein said second polymer is covalently bound to said ligand domain through a linker.

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Synthetic construct

<400> SEQUENCE: 1

Cys Ala Leu Cys Glu Phe Leu Gly
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic construct

<400> SEQUENCE: 2

Ser Glu Cys Val Glu Val Phe Gln Asn Ser Cys Asp Trp
1               5                   10
```

Embodiment 46. The method of embodiment 44, wherein said detecting indicates the presence or absence of prostate cancer in said patient.

Embodiment 47. The method of embodiment 44, wherein said biological molecule is PSMA.

What is claimed is:

1. A whole viral particle comprising a charged protein coat, said charged protein coat comprising a charged coat protein electrostatically bound to a functionalized charged polymer, wherein (i) said functionalized charged polymer comprises a charged polymer covalently bound to a first chemically reactive functional group, wherein the first chemically reactive function group is an alkyne group, and (ii) said first chemically reactive functional group is reactive to form a cycloaddition product with a second chemically reactive functional group under conditions that do not disrupt the viral particle.

2. A whole viral particle comprising a charged protein coat, said charged protein coat comprising a charged coat protein electrostatically bound to a charged polymer conjugate, wherein (i) said charged polymer conjugate comprises a product of a cycloaddition reaction comprising a charged polymer covalently bound to a hydrophilic organic polymer, and (ii) said hydrophilic organic polymer is water soluble.

3. The whole viral particle of claim 1 or claim 2, wherein said charged coat protein is a negatively charged coat protein.

4. The whole viral particle of claim 1 or claim 2, wherein said charged polymer is a cationic polymer.

5. The whole viral particle of claim 2, wherein said hydrophilic organic polymer is a polyethylene glycol.

6. The whole viral particle of claim 1, wherein said first chemically reactive functional group is a click chemistry reactive functional group.

7. The whole viral particle of claim 1 or claim 2, wherein said charged polymer is oligolysine.

8. A method of detecting a biological molecule, said method comprising:

(i) combining the whole viral particle of claim 1 and a biological molecule to a reaction vessel;

(ii) allowing the whole viral particle to specifically bind to said biological molecule; and (iii) detecting said bound biological molecule.

9. The method of claim 8, wherein said reaction vessel forms part of a biosensing device.

10. The method of claim 8, wherein said biological molecule is PSMA.

* * * * *